US010976827B2

(12) United States Patent
Battlogg

(10) Patent No.: US 10,976,827 B2
(45) Date of Patent: Apr. 13, 2021

(54) INPUT DEVICE AND METHOD OF OPERATING AN INPUT DEVICE

(71) Applicant: INVENTUS ENGINEERING GMBH, St. Anton I.M. (AT)

(72) Inventor: Stefan Battlogg, St. Anton I.M. (AT)

(73) Assignee: INVENTUS Engineering GmbH, St. Anton i.M. (AT)

(*) Notice: Subject to any disclaimer, the term of this patent is extended or adjusted under 35 U.S.C. 154(b) by 0 days.

(21) Appl. No.: 16/861,433

(22) Filed: Apr. 29, 2020

(65) Prior Publication Data

US 2020/0257369 A1    Aug. 13, 2020

Related U.S. Application Data

(60) Continuation-in-part of application No. 16/409,348, filed on May 10, 2019, now Pat. No. 10,671,171.
(Continued)

(30) Foreign Application Priority Data

Sep. 15, 2010   (DE) .............................. 102010045436
Dec. 23, 2010   (DE) .............................. 102010055833

(51) Int. Cl.
G09G 5/08       (2006.01)
G06F 3/01       (2006.01)
(Continued)

(52) U.S. Cl.
CPC ............... *G06F 3/016* (2013.01); *A61F 2/38* (2013.01); *A61F 2/60* (2013.01); *A61F 2/64* (2013.01);
(Continued)

(58) Field of Classification Search
CPC ...... G06F 1/169; G06F 1/3259; G06F 3/0205; G06F 3/0213; G06F 3/033; G06F 3/0338; G06F 2033/015; G06F 3/016; G06F 3/0482; G02B 26/005; G02B 26/026; G09G 3/344; G05G 1/08; G05G 5/03; A61F 2/38; A61F 2/60; A61F 2/64
(Continued)

(56) References Cited

U.S. PATENT DOCUMENTS 3,977,739 A     8/1976  Howe et al.
4,043,616 A     8/1977  Zimmer
(Continued)

FOREIGN PATENT DOCUMENTS

DE              1 927 328 A1    10/1970
DE       10 2004 009 906 B3     7/2005
(Continued)

*Primary Examiner* — Jennifer T Nguyen
(74) *Attorney, Agent, or Firm* — Laurence A. Greenberg; Werner H. Stemer; Ralph E. Locher

(57) ABSTRACT

An input device, in particular joystick, with an operating device and a magnetorheological brake device and a controller for activating the brake device. The operating device includes a supporting structure and an operating lever, which is accommodated on the supporting structure for pivoting around at least one pivot axis. The brake device is coupled with the pivot axis for controlled damping of a pivoting motion of the operating lever by way of the controller.

19 Claims, 19 Drawing Sheets

Related U.S. Application Data which is a division of application No. 14/747,025, filed on Jun. 23, 2015, now Pat. No. 10,318,002, which is a continuation-in-part of application No. 13/823,781, filed as application No. PCT/EP2011/004623 on Sep. 15, 2011, now Pat. No. 9,091,309.

(51) Int. Cl.

| | | |
|---|---|---|
| *A61F 2/66* | (2006.01) | |
| *A61F 2/64* | (2006.01) | |
| *A61F 2/60* | (2006.01) | |
| *A61F 2/38* | (2006.01) | |
| *G05G 5/03* | (2008.04) | |
| *F16D 57/00* | (2006.01) | |
| *F16D 37/02* | (2006.01) | |
| *G06F 3/0362* | (2013.01) | |
| *G05G 1/08* | (2006.01) | |
| *G06F 3/0482* | (2013.01) | |
| *A61F 2/68* | (2006.01) | |
| *A61F 2/50* | (2006.01) | |
| *F16D 37/00* | (2006.01) | |

(52) U.S. Cl.
CPC ............ *A61F 2/6607* (2013.01); *F16D 37/02* (2013.01); *F16D 57/002* (2013.01); *G05G 5/03* (2013.01); *G06F 3/0362* (2013.01); *A61F 2002/5004* (2013.01); *A61F 2002/6836* (2013.01); *A61F 2002/6845* (2013.01); *A61F 2002/6863* (2013.01); *F16D 2037/002* (2013.01); *F16D 2300/0214* (2013.01); *F16D 2300/18* (2013.01); *G05G 1/08* (2013.01); *G06F 3/0482* (2013.01)

(58) Field of Classification Search
USPC .................................................. 345/156, 161
See application file for complete search history.

(56) References Cited

U.S. PATENT DOCUMENTS

| | | | |
|---|---|---|---|
| 4,898,480 A | 2/1990 | Raj et al. | |
| 6,186,290 B1* | 2/2001 | Carlson | ................ F16D 57/002 |
| | | | 188/161 |
| 6,729,996 B2 | 5/2004 | Green et al. | |
| 9,091,309 B2* | 7/2015 | Battlogg | ................. F16D 37/02 |
| 2002/0113771 A1* | 8/2002 | Rosenberg | ............... G09B 9/28 |
| | | | 345/156 |
| 2005/0112375 A1* | 5/2005 | Schade | ................ B22F 1/0088 |
| | | | 428/403 |
| 2006/0033068 A1* | 2/2006 | Cheng | ...................... H01F 1/44 |
| | | | 252/62.52 |
| 2008/0053776 A1 | 3/2008 | Moser et al. | |
| 2010/0096233 A1* | 4/2010 | Smith | .................... F16D 37/02 |
| | | | 192/21.5 |
| 2011/0045932 A1* | 2/2011 | Fauteux | ................... B25J 9/102 |
| | | | 475/221 |

FOREIGN PATENT DOCUMENTS

| | | |
|---|---|---|
| DE | 10 2004 062 320 B4 | 7/2006 |
| DE | 10 2005 006 232 B3 | 11/2006 |
| DE | 10 2006 034 966 A1 | 1/2008 |
| DE | 10 2007 006 015 A1 | 8/2008 |
| DE | 10 2007 006 061 A1 | 8/2008 |
| DE | 10 2007 028 990 A1 | 12/2008 |
| DE | 10 2007 061 633 A1 | 6/2009 |
| EP | 1075979 B1 | 10/2005 |
| JP | 10176719 A | 6/1998 |
| WO | 2008/095460 A1 | 8/2008 |

* cited by examiner

INPUT DEVICE AND METHOD OF OPERATING AN INPUT DEVICE

CROSS-REFERENCE TO RELATED APPLICATION

This application is a continuation-in-part of patent application Ser. No. 16/409,348, filed May 10, 2019; which was a divisional of patent application Ser. No. 14/747,025, filed Jun. 23, 2015, now U.S. Pat. No. 10,318,002 B2, which was a continuation-in-part of patent application Ser. No. 13/823,781, filed Mar. 15, 2013, now U.S. Pat. No. 9,091,309 B2, which was a § 371 national stage of international application PCT/EP2011/004623, filed Sep. 15, 2011; the application further claims the priority of German patent applications DE 10 2010 045 436, filed Sep. 15, 2010, and DE 10 2010 055 833, filed Dec. 23, 2010; the prior applications are herewith incorporated herein in their entirety.

BACKGROUND OF THE INVENTION

Field of the Invention

The present invention relates to an input device, in particular a joystick, including at least one operating device and at least one magnetorheological brake device, and with at least one control device for activating the brake device. The operating device comprises at least one supporting structure and at least one operating lever, which is accommodated on the supporting structure for pivoting around at least one pivot axis. In particular at least one sensor means for detecting the pivot angle of the operating lever is comprised.

In the prior art, joysticks tend to include a mechanical slide gate, or mechanical spring or detent systems to represent a variety of functions. In particular the joysticks of utility vehicles or off-highway vehicles such as construction machines and the like tend to include mechanical solutions with slide gates and return springs and friction brakes for the pertaining detent positions and for returning to the neutral position. A complex gear transmission and/or a Cardan shaft or the like tend to be provided for transmission of movement. Potentiometers, Hall effect sensors or encoders are employed for signal generation or position detection. In the case of desktop applications, desk joysticks have become known for indoor applications, e.g. in laboratories for controlling laboratory apparatuses, medical devices, machines or industrial robots, etc.

Joysticks with force feedback are known for use in gaming (computer games) and in other applications. These force feedback joysticks capture situations such as bumpy flooring, which are reported back to the gamer (feedback) as mechanical feedback, in the shape of jolting or light or heavy joystick handling. The prior art has often employed vibration motors, which cannot generate any torque or force increases in the operating member. Electric motors or hydraulic or pneumatic cylinders, which in the case of professional joysticks/simulators can generate operating forces exceeding 100 N (Newton) on the operating surface, for providing a highly realistic feel, are expensive, large, and complex. Given a lever distance (distance from the joystick pivot point to the user's hand) of 10 to 15 cm, this corresponds to a rotational force of 10 to 15 Nm. Generating such a high torque at high quality (little interplay, fairly silent, fast response, stepless control) requires particularly large, often very expensive actuators, which moreover require much mounting space. The mounting space is very tight in many applications.

SUMMARY OF THE INVENTION

It is accordingly an object of the invention to provide an input device, which overcomes the above-mentioned and other disadvantages of the heretofore-known devices and methods of this general type and which provides for improved operating quality and the scope of function of such an input device (user oriented design of the haptic feedback). The input device is preferably also intended for particularly flexible use in various fields of application. At the same time the input device should be compact in structure or require little mounting space, and should be uncomplicated and inexpensive in manufacture.

With the above and other objects in view there is provided, in accordance with the invention, an input device, comprising:

an operating device, said operating device including a supporting structure and an operating lever supported on said supporting structure for pivoting around at least one pivot axis;

a magnetorheological brake device; and a controller for activating the brake device a sensor unit for detecting a pivot angle of said operating lever;

wherein said brake device is coupled with said pivot axis, for controlled damping of a pivoting motion of said operating lever by way of said controller.

The input device according to the invention is in particular configured as a joystick. The input device comprises at least one operating device, and at least one magnetorheological brake device, and at least one control device for activating the brake device. The operating device comprises at least one supporting structure and at least one operating lever. The operating lever is in particular configured as a joystick lever. The operating lever is accommodated on the supporting structure for pivoting around at least one pivot axis. In particular at least one sensor means for detecting the pivot angle of the operating lever is comprised. The brake device is coupled with the at least one pivot axis, so that the control device can control and dampen at least one pivoting motion of the operating lever.

The control device is in particular configured to activate the brake device, at least depending on at least one control command. The control device is in particular suitable and configured to convert the control command into at least one haptic signal, which is perceptible on the operating lever, preferably as a defined sequence of deceleration torques. In particular can the user thus receive, at least as a consequence of an input made and/or while making an input, a haptic feedback (so-called force feedback).

The input device according to the invention offers many advantages. The target-controlled damping of the operating lever offers a considerable advantage. Another particular advantage is the haptic feedback (so-called force feedback). This considerably improves the operating quality and at the same time, the safety of the operating processes. At the same time it enables a particularly compact damping, which saves mounting space and can be readily implemented.

In particular the pivoting motion of the operating lever is damped at least depending on the pivoting angle of the operating lever captured by sensors. The pivoting motion of the operating lever can in particular be damped by means of the brake device. For this purpose, the brake device and the control device are in particular in functional connection. The control device can in particular control the brake device. The pivoting motion of the operating lever can in particular be controlled for damping by means of the brake device and by means of the control device. The brake device can in particular be controlled by the control device, such that the pivoting motion of the operating lever is selectively, and preferably (dynamically) adjustably, damped. The control device obtains, in particular depending on at least one of the parameters described below, a target deceleration torque, and then activates the brake device such that the brake device applies a target deceleration torque for damping the pivoting motion of the operating lever.

Following an actuation, the operating lever can pivot back to an intended neutral position, preferably automatically, by means of at least one resetting unit. The control device is preferably suitable and configured to selectively damp at least one resetting motion carried out by the resetting unit, by means of the brake device. Damping the resetting motion can preferably be carried out separately for all the pivot axes provided. The resetting motion is damped in particular by adapting the deceleration torque of the brake device.

Damping the resetting motion effectively prevents the operating lever from unwanted overshooting around the neutral position. This is to ensure that the operating lever is precisely braked and retracted toward the neutral position after being released, due to the spring restoring force. In the case of conventional joysticks, the lever tends to overshoot past the neutral position, and to return after being released from a spring-biased position (e.g. end position), so that the lever needs some time to level out. This can cause problems when operating vehicles and machines and is very undesirable in gaming, since these settling motions also cause input, or control commands issued by the input device, i.e. the tool operated by the joystick performs the same settling motion. The invention or one of its configurations solves this problem while also considerably enhancing the control comfort and also ensuring reliability of operation.

The input device can particularly advantageously be employed e.g. for controlling vehicles and/or aircraft and in particular for controlling utility vehicles and preferably for controlling off-highway vehicles (these machines may also be referred to as self-moving machines) such as snow groomers, tractors, excavators, cranes, etc. The input device can be employed for controlling vehicle operation and/or other functions such as work functions.

The input device can particularly preferably also be employed in computer games or for gaming. These situations, or situations simulated by means of software, can be for example:

A stairway in a game, over which the virtual gamer must walk, may be represented by the joystick as a rippling feedback. When the virtual gamer, moved by the joystick, is standing in front of a door or wall, then the operating force increases up to the end stop (high operating force or high pivoting torque of the operating lever). When the gamer in a soccer game (e.g. FIFA) possesses the ball, actuating the joystick offers increased resistance.

In target and shooting games: Different feedbacks can be selected according to the weapon's weight or firepower. The torque characteristic of the trigger on the game controller (joystick in Y-direction) for actuating firearms changes during the game, according to the weapon selected. Jamming: blocks. Ammunition running short: operation stiffer, or rippling.

Simulator games (car races . . . ): In motor racing game or agricultural simulator: controlling the operating force (e.g. movements of the vehicle) according to the ground such as asphalt, sand, soil, etc. Peak Valley—In settings, or for acceleration, i.e. resistance. Full stop—Accident in a racing game, so as to feel the collision. Fine Ripple—For scrolling, or on asphalt. Medium Ripple—For traveling on softer ground. Hard Ripple—Traveling over meadows, hills, etc.

Help (learning mode): Preferred joystick movements (e.g. if the gamer is to move in the Y-direction only) appear easier than joystick movements/commands which are disadvantageous for a positive game progression.

Networked gaming: The haptic (force feedback) changes, depending on the other gamers respectively their input/cooperation. This allows faster and more precise controlling.

The input device may be employed in other applications. The input device can for example be employed for operating flying machines (e.g. drones), electronic devices/smart devices, televisions (e.g. as a joystick on the remote control, for navigating through the apps or transmitters and making selections), machines such as in particular machine tools and production machines, and devices and preferably medical devices or industrial robots.

Navigating a cursor in a display/indicating device is also advantageously possible. When the cursor moved by the joystick virtually rides over or past e.g. a significant location or a significant input target e.g. in a navigation application, then the joystick can briefly output a higher torque or a higher operating force (force feedback), whereby the user recognizes the situation quicker and can select more easily. Select (choose)=confirm by pressing a knob on the joystick or displace the joystick in the Z-direction (push). The haptic feedback (force feedback) can adapt, depending on the significance and also on the situation. If the vehicle requires electric energy or fuel, and the vehicle user e.g. virtually overruns with the cursor a filling station in the navigation app, which is closed at the calculated arrival time, this information is haptically passed to the user's hand by no feedback, or slight feedback (no or weak ripple). Preferred filling stations are represented with more intensive haptic. In the case of electric vehicles the feasible operational range is calculated in real time and weighted according to the operational range (safely reachable targets: hold/stop (high torque at the joystick), critical targets due to the battery operational range: no feedback or (followed by) strong vibrations as a warning . . . ). This is also true for selecting tools on a machine tool, for "catching" a significant drawing line or a dimensioning starting point in a CAD system, or the focusing point in a camera, or flight targets for a drone, or in a game (gaming).

For controlled damping of the resetting motion it is in particular provided for a deceleration torque to be adapted to the progression of a characteristic curve of the resetting unit. The characteristic curve in particular describes a resetting torque as a function of the pivoting angle of the operating lever. The deceleration torque is in particular set in relation to the pivoting angle of the operating lever, so that the deceleration torque at the pivoting angle is the same or higher than the resetting torque at the same pivoting angle. The deceleration torque is in particular adapted to the spring characteristic of a resetting spring. For this purpose the pivoting angle of the operating lever is in particular detected by the sensor means.

The sensor means comprises in particular at least one sensor (e.g., encoder, rotary encoder, Hall sensor . . . ). The sensor is e.g. an angle sensor and in particular a rotation angle sensor. An absolute position (e.g. absolute value encoder) or a relative position can be readable. The sensor means can detect the pivoting angle of the operating lever immediately or also indirectly by way of the position of another component and in particular the brake device. For this purpose, an angular position and/or a rotation angle of the brake device is for example detected. The detected pivoting angle is preferably provided to the control device for activating the brake device.

The control device is preferably suitable and configured to automatically fix the operating lever after actuation in the current actuating position. For this purpose the control device is preferably suitable and configured for controlled setting of at least one deceleration torque, by means of the brake device, which corresponds to, or is higher than, a resetting torque of the resetting unit in the current actuating position. The advantage thereof is that after being released, the operating lever remains in any desired position and does not return to the neutral position. This function, also referred to as a smart stop, is highly advantageous for multiple operating scenarios.

The stop/deceleration torque can be set high enough so as to enable, using increased force, moving the operating lever further (overpressing). The deceleration torque may also be set high enough so that given the manual operating forces, the operating lever blocks. Shifting the operating lever further, using increased force, and/or blocking the operating lever, may take place in at least one, or in multiple, pivoting direction(s).

In all the configurations it is particularly preferred for the operating lever to be accommodated on the supporting structure about at least two pivot axes. Alternately, the operating lever may be accommodated on the supporting structure pivotable about at least three or four or more pivot axes. The operating device comprises in particular at least two or three or more pivot axes. The operating lever is in particular accommodated on the supporting structure for pivoting at least biaxially and preferably multiaxially.

At least one brake device is preferably coupled with at least one pivot axis each. The control device is preferably suitable and configured to separately damp at least part of the provided pivot axes and preferably all of the provided pivot axes, and in particular also independently of one another, in a pivoting motion of the operating lever. All the pivoting motions of the operating lever can be damped in particular separately, and preferably independently of one another. Alternately, two or more pivot axes can be equipped with one shared brake device. Then, one transmission device is in particular provided for coupling the pivot axes with the shared brake device.

It is advantageous and preferred for the control device to be suitable and configured to actuate and preferably adapt, and in particular to change and/or intentionally maintain the brake device, depending on a pivoting angle of the operating lever obtained by sensors. The control device is preferably suitable and configured to adapt the damping of the pivoting motion of the operating lever, at least depending on the pivoting angle of the operating lever detected by the sensor means. The input device comprises in particular at least one sensor means for detecting the pivoting angle of the operating lever (in particular the sensor means described above). The pivoting angle of the operating lever can in particular be detected separately for each of the pivot axes provided. For example at least one angle sensor or the like is provided for each of the pivot axes. The control device is in particular suitable and configured to set by means of the brake device, a deceleration torque for the operating lever, depending on the pivoting angle and/or the time. The control device adapts the deceleration torque, in particular taking into account the pivoting angle and/or the time, and preferably dynamically. Damping curves, which describe the deceleration torque as a function of the pivoting angle and/or the time, can in particular be set and dynamically adjusted.

It is likewise advantageous and preferable for the control device to be suitable and configured to actuate the brake device depending on at least one control command of an input receiving unit. The input receiving unit can in particular be, or is, coupled with the input device so as to establish a functional connection. The input device according to the invention can comprise at least one input receiving unit. It is also possible for the input receiving unit and the input device to be provided by an input system. Such a control command can be entered in the input receiving unit independently of an input and/or as a response (feedback) to an input performed by the input device. The deceleration torque is in particular adapted, depending on the control command. The control command can relate to at least one real operational situation (in particular an operational situation of the input receiving unit and/or the input device) and/or at least one situation simulated by means of a software.

The control device is in particular suitable and configured to receive the control command and then to modify the deceleration torque, taking into account at least the control command. The control device is in particular suitable and configured to carry out the actuations of the brake device described above and/or below, also at least partially depending on the control command. This allows to adapt the damping of the operating lever to the actual requirements of an input receiving unit, so as to always ensure optimal and particularly safe operation.

It is also preferred and advantageous that the at least one control command is provided by the input device itself. A control command provided by the input device itself is, for example, the pivoting angle captured by sensors, and/or the moving speed of the operating lever and/or a time and/or an operating mode of the input device and/or a user input lodged in the input device (e.g. selected user profile, key strokes, etc.) and/or at least one (other) parameter captured by sensors (e.g. acceleration or location of the input device). The control command may be lodged in the control device and/or be generated therein by means of lodged algorithms. The control command can be generated and/or modified by at least one user input. At least one control command from another source may also be provided. The control device may in particular receive and process several different control commands.

The control device is preferably suitable and configured to convert the control command to at least one haptic signal perceptible on the operating lever (force/moment variation), in particular so that the user can receive, due to an input, a haptic feedback (e.g. increased force to the man-machine interface). The input receiving unit can in particular selectively influence the movability or damping of the operating lever. This enables a particularly advantageous realization of haptic feedbacks (such as force feedback). The haptic signal preferably comprises at least the defined sequence of deceleration torques described in the scope of the present invention. Particularly preferably the haptic signal comprises at least the defined sequence described in the scope of the present invention, of (rapidly) changing deceleration torques or forces in the man-machine interface (also referred to as ripple/ticks/pattern). In this way, a state of the vehicle or the machine can for example be communicated.

The control device is in particular suitable and configured to block at least one pivoting motion of the operating lever in at least one pivoting direction and to enable it in at least one opposite pivoting direction. This allows to move the operating lever as required in one direction only, along the pivot axis. This unidirectional movability of the operating lever is advantageous in many situations and it may be activated and deactivated as desired with the invention. The control device is in particular suitable and configured to block the pivoting motion from the neutral position and/or from a current actuating position, unidirectionally and/or bidirectionally and/or multidirectionally. The pivoting motion of the operating lever can also be provided for directional damping.

The control device is in particular suitable and configured to change the direction in which the operating lever is blocked, and the direction in which the operating lever is enabled. The direction is in particular changed at least in relation to a situation and/or the pivoting angle and/or the time and/or the control command. The control device may preferably also block both directions, and/or enable both directions, and/or apply a continuous and/or variable deceleration torque on both directions.

The control device is preferably suitable and configured, when at least one defined pivoting angle is reached, to increase the deceleration torque by means of the brake device over at least one specific pivoting angle range, and in particular to fix the operating lever in at least one target position outside of the neutral position, after the pivoting angle range has been overcome. For this purpose the control device can set at least one selected deceleration torque, which corresponds to, or is higher than, a resetting torque of the resetting unit in the target position.

Thus, after overcoming the torque spike, the operating lever automatically remains in place when it is released (kick and hold). The target position is in particular defined by the pivoting angle of the operating lever along at least one pivot axis. The control device is preferably suitable and configured to shift the operating lever back to the neutral position beneath the defined pivoting angle.

The control device is preferably suitable and configured to dynamically determine the defined pivoting angle and/or the deceleration torque and/or the pivoting angle range and/or the target position. Determining may be dependent on the pivoting angle of the operating lever and/or the time and/or the control command. The control device is in particular suitable and configured to set, and/or cancel, and in particular to dynamically determine, the pivoting angle range and/or the target position in any desired position in the operational pivoting range of the operating lever.

The control device is preferably suitable and configured to provide the increased deceleration torque for overcoming the pivoting angle range in one pivoting direction only, so that, after overcoming the pivoting angle range, the operating lever can be returned, absent such increased deceleration torque. A brief resistance is for example generated in one direction, while the return movement to the neutral position is performed without an additional resistance (kick down). The control device in particular adapts, and in particular dynamically adapts, the increased deceleration torque and/or the direction for the increased deceleration torque, depending on the pivoting angle and/or the time and/or the control command.

In a preferred and advantageous configuration the control device is suitable and configured to fix the operating lever in at least one adjustable detent position, and preferably in multiple detent positions, which can be dynamically specified. The control device is preferably suitable and configured, by means of the brake device, to perform a controlled increase of a given deceleration torque (increase by a defined factor), so as to prohibit any further movement or resetting (by hand and/or by means of the resetting unit), without applying additional force and/or without any additional user action. The control device is in particular suitable and configured to dynamically set, and preferably to specify, the detent position, depending on the pivoting angle and/or the time and/or the control command.

This configuration offers many advantages and allows, for example, the simulation of a selector lever of an automatic motor vehicle transmission (P R N D). Moreover the input device can be employed in a very large number of different devices and machines respectively vehicles, without requiring any structural modifications. The user receives an individual, adapted feedback, corresponding to the application purpose. This increases the operating comfort and reduces operating errors. The detent positions allow particularly intuitive and precise input.

An arbitrary quantity of detent positions, which the brake device can displace, is in particular adjustable in arbitrary positions in the operational pivoting range of the pivoting lever. The detent positions are adjustable in particular depending on the pivoting angle and/or the time and/or the control command. The detent positions are in particular defined at least by a pivoting angle and a deceleration torque. The user action comprises in particular at least one actuation of at least one switching element. Pressing a key on the operating lever is provided, for example.

The control device is in particular suitable and configured to increase the deceleration torque, already starting at a defined pivoting angle prior to reaching a detent position, and/or to decrease it, starting at a defined pivoting angle after leaving the detent position. Increasing and/or decreasing may be carried out continuously or variably.

In a particularly advantageous configuration the control device is suitable and configured to block the operating lever as it reaches at least one specified pivoting angle and/or in the neutral position and/or in a currently held position, such that a manual force to be applied operationally cannot cause any further movement in at least one pivoting direction and/or in all the operational pivoting directions. For such blocking, the control device increases in particular the given deceleration torque by a defined factor. This enables a particular good simulation of mechanical stops. One advantage over conventional, mechanical damping is, that no stick slip effect will occur, and no initial stick friction must be overcome. Such blocking may also be provided in at least one of the detent positions described above.

It is possible to provide, prior to reaching the defined pivoting angle, a free and/or weaker damped movement of the operating lever, so as to enable automatic return to the zero position from there.

It is possible for the control device to block the pivoting motion of the operating lever for all the pivot axes and for all the pivoting directions such that the manual force applied operationally does not allow any further movement. This operating mode (axis locked) allows reliable and safe locking of the input device as required, or depending on the situation (situation dependent feedback). Blocking is also possible in one pivoting direction only and/or for selected pivot axes only. The pivoting direction and/or the pivot axis is/are selected, for example, due to a control command or a user action or the near field recognition. For example when a container in a container aisle of a container port (there are further containers to the left and right of the container aisle) is moved forwards or rearwards (X-axis) by means of the joystick, then the lateral axis of motion (Y) may be blocked or be made hard-going, which prevents or prohibits collision. Near field recognition systems (motion sensors, camera systems, GPS, radar systems . . . ) sense the situation, a computer analyzes the data, which it lets flow into conceivable or useful motion patterns of the joystick in real time.

The control device can preferably modify the deceleration torque, taking into account the motion speed of the operating lever, in particular the angular velocity of a gear transmission and/or the brake device. The control device is in particular suitable and configured to compensate, at least approximately, a structural, speed-dependent deceleration torque of the brake device, to enable a uniform deceleration torque across various speeds.

It is preferred for the control device to be suitable and configured to simulate at least one slide gate mechanism, by a combination of a plurality of detent positions, and at least one zero position, and/or at least one target position, and/or a plurality of blockings of the operating lever dependent on the pivoting angle. For example, a slide gate mechanism of a mechanical gear transmission of a motor vehicle and for example an H-shifting can be simulated. For this purpose the input device comprises in particular at least two pivot axes (X- and Y-axes). Multiple brake devices are in particular coupled with a pertaining pivot axis each, to generate a slide gate-like movement of the operating lever, controlled by the control device.

In particular at least one control algorithm for simulating at least one slide gate mechanism is lodged in the control device. The control device in particular selects a specific slide gate mechanism, dependent on a user input and/or on the control command of the input receiving unit, which it simulates. When the input device is installed in a utility vehicle, different slide gate mechanisms can for example be simulated, for a gear transmission, or for operating a work function. Thus, a joystick can perform multiple functions.

In a particularly advantageous configuration, the control device is suitable and configured, to decelerate and to enable the pivoting motion of the operating lever in a controlled sequence, by means of the brake device. In order to realize such a sequence, the control device is in particular suitable and configured to set various levels of deceleration torques for the deceleration and enabling. Such a sequence offers a reliably perceptible, haptic feedback, including in difficult operating conditions, and it can be particularly readily employed with the invention.

The sequence is in particular composed of a sequence of relative maxima with a higher deceleration torque, and relative minima with a lower deceleration torque. The angular distance of a period of adjacent, relative maxima is in particular settable, and it is set. The progression of the deceleration torque is in particular set over a period, depending on the operating mode set. Such a sequence showing particularly short intervals may also be referred to as ripples/ticks. Such a sequence is in particular configured from a defined combination of deceleration torques as functions of the time and/or of the angle. The deceleration torques for deceleration and/or enabling are preferably set as a function of the time and/or as a function of the pivoting angle and/or depending on a control command. Such a sequence can in particular be set in dependence on the pivoting direction, and for example in one pivoting direction only, or alternately in both pivoting directions.

Such a sequence may also be provided for damping the resetting motion. Then the resetting motion after releasing the operating lever is damped, for example, so that the operating lever is returned to the neutral position with a ripple.

The deceleration torques of the sequence are started and/or maintained and/or terminated, in particular dependent on the angle and/or dependent on the time. Preferably, these dependencies may be provided for changing within a sequence. For example the sequence is started dependent on the angle or dependent on the time, and the length of the sequence is then set dependent on the time or dependent on the angle respectively.

The control device is preferably suitable and configured to start the deceleration torques of the sequence dependent on the time, and to maintain them, dependent on the angle. The control device is in particular suitable and configured to omit setting a deceleration torque provided in the sequence, if an angular position provided for the start (specific pivoting angle of the operating lever) is overrun, while a deceleration torque is being maintained.

The control device is particularly preferably suitable and configured to set the different deceleration torques of the sequence to a controlled frequency and preferably set to such a frequency that the pivoting motion of the operating lever is damped by way of controlled vibrations. The frequency is in particular at least 20 Hz and preferably at least 50 Hz.

The control device is in particular suitable and configured for dynamic adjustment of the different deceleration torques of the sequence over the time and/or the pivoting angle and/or the motion speed (angular velocity) of the operating lever and/or the quantity of previously performed settings of deceleration torques. These parameters may also be provided by way of control commands. For example, this allows haptic signals of an approach to an end position or detent position. The user can thus be warned e.g. if he pivots the operating lever so as to set the vehicle to an operating state which requires particular attention (movement of the tool or the load in spatially restricted areas; risk of collision . . . ).

The control device can dynamically adjust the different deceleration torques of the sequence, including depending on the control command of the input receiving unit and/or of the input device. The control command allows, for example, to indicate to the input device that a maximum speed is reached, or a crane boom is overstressed, so that the user then perceives a vibration of the operating lever.

The maximum bearing load of a crane boom is, for example, dependent on the traversing position. Loads moved further outwardly on the boom must be lower than they can be in the vicinity of the center of the crane. Near field recognition-measuring systems can sense and analyze the situation and can thus inform the operator, by haptics about force variations in the operating member, that he moves in the "green" range (permissible, uncritical), "amber" range (it might turn critical) or red range (overload—the load is too far outwardly on the boom). The operator can then decide, on the basis of haptic feedback in the operating member, how to proceed further. He receives this significant feedback without having to move his eyes away from the process, thus he does not need to watch a display on the control desk, which is highly advantageous.

The control device is in particular suitable and configured to set a sequence including controlled variations of deceleration torques. For this purpose a sinusoidal or cosinusoidal path is in particular provided. For this purpose the path shows in particular a (slight) offset in the negative range. The offset is in particular less than 30% and in particular less than 20% and preferably less than 10%. At least two zero crossings per period are in particular provided for the progression. The brake device is in particular controlled by way of a sine signal or cosine signal, in particular showing a predetermined and in particular adjustable (slight) offset from the zero point. Particularly preferably such a sequence shows a progression which corresponds to the spring characteristics of a mechanical spring. Thus, a mechanical joystick can be simulated particularly realistically.

It is possible and preferred that the control device is suitable and configured, when the operating lever is actuated after a defined time of the operating lever not being actuated, to emit at least one haptic warning signal, and for this purpose to preferably set a defined sequence of deceleration torques. The sequence is configured in particular as described above. It is also possible and preferred that, after a defined time when the operating lever is not operated, the operating lever is damped and/or blocked at an increased level, in at least one pivoting direction and/or in relation to at least one pivot axis, as described above. This allows to effectively counteract an inadvertent actuation.

It is preferred that the control device is suitable and configured to actuate the brake device at a regulating frequency of at least 5 kHz and preferably at least 10 kHz and particularly preferably at least 50 kHz. The brake device is in particular suitable and configured to implement such a regulating frequency.

The control device is in particular suitable and configured to damp the brake device in real time. The brake device is in particular suitable and configured to implement the deceleration torque in real time. The damping is in particular adjustable in dependence by means of the control device of the brake device in real time, to the pivoting angle and/or the time and/or to a control command and/or to a motion speed respectively angular velocity of the operating lever. The brake device is in particular suitable and configured to change the deceleration torque, within less than 100 milliseconds, by at least 30%. The deceleration torque is in particular variable within less than 10 milliseconds by at least 10%, preferably by at least 30% and particularly preferably by at least 50%. The deceleration torque may also be variable within less than 100 milliseconds by at least 100% or 500% or by ten times or a thousand times the amount.

The magnetorheological brake device is preferably suitable and configured to provide, in particular by means of a sensor, rotary encoder, or incremental encoder, at least 30,000 increments, in particular 30,000 increments/revolution, for one pivot axis of the operating lever. Incremental encoders provide, for example, a specific quantity of impulses per revolution, or a so-called zero pulse per revolution. These may be incremental encoders using UV/VIS signals or absolute shaft encoders). This provides particularly effective implementation of haptic signals. The increments can in particular be employed to provide the detent positions and/or the sequences described above. In particular at least 30,000 increments per revolution of the brake device and/or the transmission stage can be provided. The sensor means can in particular comprise at least 30,000 increments per revolution of the brake device.

The brake device is preferably coupled with the at least one pivot axis via at least one transmission stage. The transmission stage preferably has a gear ratio between 2:1 and 5:1. Other gear ratios are likewise conceivable.

The transmission stage comprises in particular at least one belt drive. The belt drive in particular couples the pivot axis with a rotation axis of the brake device. The belt drive comprises in particular at least two belt pulleys and at least one belt. Other types of transmission stages are likewise conceivable. For example, the transmission stage may include a gear transmission and/or lever mechanism or the like. The pivot axes are in particular coupled with one rotation axis of the brake device each.

The applicant reserves the right to claim an input system, which comprises at least one input device according to the invention, and at least one input receiving unit in functional connection with the input device. The input receiving unit is preferably configured as a utility vehicle, so that the input device can at least partially operate the functions of the utility vehicle. It is also preferred that the input receiving unit is configured as a computer, and that the computer is in particular equipped with a simulation program and/or a gaming program. A computer is for example understood to include: computer, control device, processor, which processes data by means of programmable rules for computing, etc. The functions of the simulation program and/or the gaming program can in particular be operated by the input device, at least partially.

The utility vehicle is preferably configured as an off-highway vehicle. Such a utility vehicle can also be referred to as a self-propelled work machine. The utility vehicle is in particular an agricultural or forestry utility vehicle. Other types of utility vehicles are conceivable. The utility vehicle can, for example, be an agricultural tractor, a harvester, excavator, crane, or the like. The utility vehicle may also be a drone or other aircraft.

The input system also offers a particularly advantageous solution to the object introduced above. The input device and the input receiving unit are preferably configured as has been described above for the input system according to the invention.

The method according to the invention serves to operate an input device and in particular a joystick. At least one operating lever of the input device is pivoted, at least partially manually, about at least one pivot axis, to perform an input into an input receiving unit, which is in functional connection with the input device. At least one pivoting motion of the operating lever can be selectively damped (and enabled) by means of at least one magnetorheological brake device coupled with the pivot axis. The brake device is selected by means of at least one control device, at least depending on the pivoting angle and/or the motion speed of the operating lever (in particular sensed by means of at least one sensor means), and/or on the time and/or at least one operating state of the input receiving unit, to perform controlled modification of the damping.

The method according to the invention also offers many advantages. The method is preferably designed so that the input device and/or input system described above can be operated using the same. The input device and/or the input system according to the invention are in particular suitable and configured to be operated using the method according to the invention.

The operating state of the input receiving unit preferably relates to at least one of the following parameters: power status, speed, acceleration, position in space, ambience, ground traveled, work performed, selected user profile, selected operating mode, activities of an assistance system and in particular operating assistance system, software-simulated situation, input conditions for operating a program (menu items, choice options, fields, etc.).

The damping or blocking of the operating lever pivotability is preferably selectively increased in case of an operating state showing disturbances above a threshold value (for example, due to rough ground or vibrations caused by the work) and/or endangerment (for example, high speed), and/or if an assistance system actively intervenes in using the input receiving unit. In order to detect these operating states, the input receiving unit preferably includes at least one suitable sensor means and for example an acceleration sensor or the like.

The operating lever is in particular provided with at least one actuating member. The actuating member is in particular configured as an automatically resetting operating knob or operating key. At least one operating switch may be provided additionally or alternately. It may be employed for user input, which is effective on the damping of the pivoting motion of the operating lever. It may for example be used for cancelling controlled blocking of the pivoting motion.

An operating state showing a parameter above a threshold value and/or a danger above a threshold value and/or involving intervention by an assistance system, is preferably signaled by haptics by means of a controlled sequence of different deceleration torques during a pivoting motion of the operating lever. Such a sequence is preferably configured as described above for the input device according to the invention. This enables effective and secure counteraction to maloperation of the input receiving unit. It is also possible to provide for weaker damping, or enabling, of the pivoting motion of the operating lever when the parameter and/or the endangerment fall back below the threshold value.

It is advantageous and particularly preferable for the pivotability (pivoting motion) of the operating lever to be damped and/or blocked more intensely, variably but controlled, depending on at least one situation. It is preferably provided for the pivoting motion of the operating lever to be variably modified, depending on at least one real operational situation (in particular an operational situation of the input receiving unit and/or of the input device) and/or at least one software-simulated situation, so as to result in a controlled increase or decrease, or even blocking, of the damping.

In configurations including a damping depending on the pivoting angle and/or the motion speed of the operating lever, the pivoting angle respectively the motion speed of the operating lever is in particular detected by means of at least one sensor means.

In the scope of this invention the described designs for controlled damping of the pivoting motion can preferably be performed separately for all, or at least part, of the provided pivot axes and/or pivoting directions. The pivoting motion of the operating lever around a pivot axis can in particular be damped independently of the pivoting motion of the operating lever around at least one other pivot axis. The directions of the pivoting motions of the operating lever can in particular be damped separately, and preferably also independently of one another. The forward movement can in particular be damped separately, and preferably independently of a reverse movement.

In the scope of this invention the terms damp and decelerate are preferably used as synonyms. The control device is in particular suitable and configured for controlled deceleration and enabling of the at least one pivoting motion and the resetting motion, and to block, given the operationally expected manual forces at the operating lever. The pivoting motion may also comprise, or be configured as, a rotary motion. Manual forces of at least 100 N can in particular be generated on the operating lever. In the scope of this invention all the suitable deceleration torques can preferably also be employed as holding torques for holding the operating lever in place, and be adapted according to the invention.

Damping the pivoting motion takes place in particular by adapting the deceleration torque of the brake device. The control device is in particular suitable and configured to adapt the deceleration torque of the brake device, for controlled damping of the pivoting motion. The control device is in particular suitable and configured to dynamically set the deceleration torque.

The control device can preferably set an arbitrary deceleration torque, which the brake device can generate, for an arbitrary pivoting angle, which the operating lever can reach and/or for an adjustable duration. The control device comprises in particular a multitude of adjustable operating modes, and it is preferably suitable and configured to carry out assignment of deceleration torque and pivoting angle and/or duration, depending on the operating mode.

The control device is in particular an electronic control device. The control device comprises in particular at least one control algorithm. The deceleration torque is in particular set by activating an electric coil device of the brake device, at a specific current and/or a specific voltage or a suitable signal.

The deceleration torque is in particular adapted as a function of the pivoting angle and/or the time and/or the motion speed (in particular angular velocity) of the operating lever and/or the control command of the input receiving unit. The pivoting motion is in particular damped, dependent on the angle and/or dependent on the time and/or dynamically. The control device is in particular suitable and configured to damp the pivoting motion at a deceleration torque that is continuous or variable, and in particular dynamically adapted over the time and/or the pivoting angle.

In the scope of this invention, enabling the pivoting motion is in particular understood to mean that only an operational base momentum of the brake device is given, without any additionally imposed magnetorheological deceleration, such as by energizing a coil device of the brake device. When the pivoting motion is enabled, the magnetorheological brake device is in particular inactive, so that no field is generated for actively influencing the magnetorheological medium of the brake device.

The embodiments described in the scope of this invention can in particular be employed for damping the resetting motion, in analogy to damping the pivoting motion. In all the configurations it is preferred for the control device to set the neutral position. The neutral position may be fixedly specified.

The brake device is in particular configured as, or comprises at least one, magnetorheological transmission device. Preferably at least one magnetorheological transmission device is assigned to each of the pivot axes. A brake device so designed allows particularly advantageous implementation of the previously described configurations for controlled damping of the pivoting motions. This transmission device can reliably produce the required deceleration torques, and can set them promptly and in real time if required, while it is also particularly compact and also very robust.

The magnetorheological transmission device presently described can be used in manifold technical fields, thus, e.g., on vehicles or industrial plants as a clutch or brake or for producing variable stops of a vehicle door. However, the presently described magnetorheological transmission device can also be used, e.g., as a steering wheel lock on the steering column of automobiles or other two-wheeled vehicles or also as an anti-slip control, torque distributor, fan clutch, etc., in vehicles. Use as a joint on prostheses, artificial limbs, or in other technical fields is also possible.

Greatly varying clutches and the like are known in the prior art, in which, for example, a second component is brought into synchronous rotational movement with a first component via the activation of the clutch. For this purpose, for example, clutch plates, which are provided with a friction lining or the like, can contact one another in order to bring the second component to the speed of the first component through the initially grinding contact.

In addition to typical clutches and brakes with conventional friction linings, clutches are also known in which, for example, a magnetorheological fluid is provided between two components, which are used as clutch plates. Magnetorheological fluids have ultrafine ferromagnetic particles, for example, carbonyl iron powder distributed in an oil, for example. In magnetorheological fluids, spherical particles having a production-related diameter of 1 to 10 µm are used, wherein the particle size is not uniform. If a magnetic field is applied to such a magnetorheological fluid, the carbonyl iron particles of the magnetorheological fluid chain together along the magnetic field lines, so that the rheological properties of the magnetorheological fluid (MRF) are substantially influenced as a function of the shape and strength of the magnetic field.

A roller bearing, using which a steering column is mounted so it is rotatable, is known from DE 10 2004 009 906 B3. The legally prescribed minimum torque of greater than 100 Nm, by at least which a steering column must be blocked in the locked state, is to be achieved solely by the increase of the viscosity. Such a bearing is constructed as in the known prior art and has a bearing outer ring and a bearing inner ring and roller balls therebetween, which support the steering column and mount it so it is rotatable. A rheologically active substance is intercalated in the bearing intermediate space. A magnetic field is applied to increase the viscosity, whereby the traction between the bearing rings changes.

Experiments of the applicant in using such a bearing as a clutch have not resulted in a usable product. Roller bearings must have a slight play to allow the required load-bearing capacity and smooth running and to prevent deflection and therefore high wear. In the case of a routine roller bearing, which is typical for steering systems, having an internal diameter of 30 mm and an external diameter of 42 mm and roller bearings of approximately 4 mm diameter, the roller bearings have a total manufacturing-related scattered play of 6 to 20 µm (radial bearing clearance, tolerance class "normal" or P5, respectively). The radial running profile on each radial side of the roller ball is then half thereof, i.e., it moves between 3 µm and 10 µm. A greater running profile impairs the load-bearing capacity, increases the running noise, and results in substantially increased wear.

Since magnetorheological fluids have magnetically polarizable particles usually having a maximum diameter of 10 µm, it has been shown that such a roller bearing immediately blocks upon the addition of a drop of a magnetorheological fluid, even without application of a magnetic field and without bearing load. This is because a particle having 10 µm diameter cannot be pressed/rolled through a gap of 3 µm in magnetorheological fluids even without the application of an external magnetic field. In addition, agglomerations or chains of two or more particles also form or form because of this, so that a blockade of the roller bearing can occur even without an external field. In the normal state, a bearing load always acts on the bearing (radial or axial force), whereby the running profile of the roller bodies under load is decreased almost to zero and high surface pressures occur, whereby the roller bearing must be mechanically blocked, since then even the smallest particles having 1 µm diameter can no longer pass through between the roller bodies and the runway. The bearing becomes unusable and/or defective and the particles mechanically jam in the running gap. It also does not matter in this case if roller bearings having oversized base running profile, e.g., SKF production series C5 are used, except for the fact that increased bearing play decreases the load-bearing capacity and greatly shortens the service life.

Due to the continuous rolling of the roller bodies on the running surface in normal operation, i.e., with radial or axial load, very high surface pressures on the running surface sometimes result, which grind flat the interposed metal particles (>99% pure iron) of the magnetorheological fluid. In addition, the coating of the particles to protect against abrasion, sedimentation, and agglomeration can be damaged. Furthermore, the running surfaces can also be damaged. In practice, it has been shown that the particles thus changed mechanically stick together or cluster even without a magnetic field, whereby the magnetorheological fluid becomes unusable. This already occurs in the event of small mechanical compressions of the particles. In addition, the particle clusters thus formed can no longer be pressed through between the roller body and the runway, even in the case of large running profiles, and block the bearing.

In addition, conventional roller bearings are finally sealed, to prevent the entry of dust and hard particles and therefore decrease wear.

This also applies to DE 10 2006 034 966 A1, which discloses a roller bearing or linear bearing according to the prior art having improved localization of the lubricant by MR fluid.

A torque clutch is known from US 2008/0053776, in which magnetorheological fluid is placed between the rolling (meshing) gear wheels and a magnetic field is applied thereto. A transmittable torque of up to 1500 Nm is thus to be modulated. In order that such forces/torques can be transmitted, the tooth flanks must touch or the gear wheel play also goes to zero in this case, respectively, whereby the interposed MRF particles are damaged by the high surface pressure, as previously described in the case of the roller bearing of DE 10 2004 009 906 B3. The tooth flanks can jam and block without a magnetic field because of the particle size and the particle accumulation (cluster formation), respectively. The surface pressure and the flank play change continuously depending on the load (the torque) in the case of US 2008/0053776.

In the case of a known magnetorheological clutch having two clutch plates slightly spaced apart from one another, the two clutch plates, which are arranged at a suitable distance, can initially rotate relatively freely relative to one another without a magnetic field. However, a certain base torque can also be transmitted in the field-free state by shearing of the MRF depending on the slip of the clutch plates. If a magnetic field is activated perpendicularly to the clutch plates, the magnetorheological fluid chains together between the clutch plates and the two clutch plates are coupled to one another. The strength of the transmittable torque is dependent on various parameters, thus, e.g., the operating distance or the torque introduction distance, respectively, the operating surface, the number of the clutch plates, the relative speed, or the slip, and the magnetorheological fluid and in particular also the strength of the magnetic field. If the maximum transmittable torque is exceeded, the transmittable torque does not decrease to zero, but rather remains approximately at its maximum possible value, since chains of the particles of the magnetorheological fluid which are torn apart reform again immediately and thus become active again.

MRF clutches according to the prior art require large clutch plates having a diameter greater than 150 mm to reach high transmittable torques of, for example, greater than 50 Nm or more. Difficulties result therefrom due to the centrifuging out of the ferromagnetic particles because of the density difference in relation to the carrier medium. The fluid and the ferromagnetic particles can unmix.

A substantial advantage of magnetorheological clutches is that the wear is reduced. The load not only occurs on the outer surfaces of the clutch plates, but rather the energy is absorbed in the entire liquid volume.

The known magnetorheological clutches have the disadvantages of the high required magnetic field strength and a certain structural size, which results from the parameters of operating diameter, operating surface, and number of plates. A corresponding structural weight results therefrom, to be able to transmit the corresponding torques, which causes a poor torque/weight ratio. Strong magnetic fields which are generated by an electrical coil continuously require a large amount of electrical power, which is also undesirable.

The preferred magnetorheological transmission device has at least two components which can be coupled, whose coupling intensity can be influenced. At least one channel is in particular provided for influencing the coupling intensity. The channel in particular at least partially contains at least one magnetorheological medium having magnetically polarizable particles, which can be influenced by a magnetic field. At least one magnetic field generating unit is in particular provided for generating at least one magnetic field in the channel, in order to influence the magnetorheological medium in the channel using the magnetic field. In this case, in particular one component as the outer component surrounds in particular the other component as the inner component. Preferably, at least one of the two components is mounted via at least one separate bearing. A distance between the outer component and the inner component is preferably at least 10 times as great as a typical mean diameter of the magnetically polarizable particles in the magnetorheological medium. The magnetic field of the magnetic field generating unit can be applied in particular at least partially to the channel in order to optionally chain together the particles and/or release them.

In particular, a proportion by volume of polarizable particles in the magnetorheological medium is greater than 25%.

Preferably, there is in particular at least one magnetically conducting part that is at least partially flowed through by the magnetic field of the magnetic field generating unit provided in the channel between the outer component and the inner component. There may also be a number of, in particular identical, magnetically conducting parts provided in the channel.

The part in the channel may be embodied as a rotating body and is embodied as a separate part between the first and the second components.

A free distance between the rotating body and the component is at least 10 times as great as a typical mean diameter of the magnetically polarizable particles in the magnetorheological medium. At least one acute-angled region, which contains or forms the magnetorheological medium, respectively, is provided between the rotating body and at least one component. The magnetic field of the magnetic field generating unit can be applied to the channel or at least a part thereof, in order to optionally chain together at least a part of the particles and wedge or release them with the rotating body. In particular, the two components can be coupled to one another optionally and in a controlled manner.

The term coupling intensity is understood in the meaning of this application to mean the coupling force and/or the coupling torque between the two components. For example, if a linear force transmission is desired, the coupling intensity thus corresponds to the coupling force. If a torque is to be transmitted, the coupling intensity means the coupling torque.

The viscosity of the magnetorheological medium is preferably variable by the field, whereby the required displacement work for the relative movement of the components and/or the rotating bodies, which are movable relative to one another, can be influenced.

Displacement work is also understood to mean the displacement force which is necessary for displacing the medium in the case of a relative movement.

It is preferable for the at least one rotating body to be arranged between the two components. However, it is also possible that one of the components is implemented as the rotating body, which is at least partially provided on or in the channel.

These magnetorheological transmission devices have many advantages. A substantial and surprising advantage of the magnetorheological transmission device results from the considerably amplified effect of the magnetic field of the magnetic field generating unit in the channel. The acute-angled region which contains the medium acts as a lever and therefore somewhat like a strong mechanical lever transmission ratio, wherein the lever substantially amplifies the effect of the magnetic field by multiple times. Thus, either the field strength of the magnetic field generating unit can be reduced with the effect remaining the same, or the effect of the magnetic field can be amplified with the field strength remaining the same or the effect can even be increased with reduced field strength. The effect is in particular increased by multiple times by the acute-angled region which contains the medium when the magnetic field acts on the medium. In particular, the magnetic field acts at least sometimes on the acute-angled region, which contains or forms the magnetorheological medium, respectively.

Because the rotating body is arranged with a substantial free distance in relation to the at least one component, a macroscopic wedge can arise, which can be used to transmit strong clutch or brake torques. Substantial structural volume can be saved by the completely surprising multiplication of the effect. The utilized effect is based on the wedge formation (cluster formation) and not only the magnetorheological chaining of individual particles. The typical reaction time for the wedge formation requires several milliseconds, while individual particles are chained together according to the MRF effect already within approximately 1 ms. This time duration, which is multiple times longer, is due to the wedge formation. Such a substantial amplification of the effect was not expected. The longer reaction time of, e.g., 5, 10, or 20 ms is more than sufficient in many applications.

The channel can also be an intermediate space or a space which is open on four sides.

An acute-angled region of the channel is defined as the channel region which appears approximately to have an acute angle in at least one cross section through the shape of rotating bodies and components. The sides of the region do not have to be linear, they can also be curved and/or have another contour. The acute-angled region defines the part of the channel in which rotating body and components have the smallest distance to one another in particular or touch, respectively, and the adjoining region, in which the surfaces of rotating body and components move away from one another.

Under the effect of a magnetic field, the acute-angled region, which contains the magnetorheological medium, is formed, in which a substantially increased viscosity is present.

The presently described magnetorheological transmission device allows a good torque to weight ratio, which can be greater than 100 Nm/kg.

A rotating body is preferably set into a rotational movement by a relative velocity in relation to at least one component. It is possible that the peripheral velocity of the rotating body is equal to the relative velocity in relation to the component. However, it is also possible that the peripheral velocity of the rotating body on its outer surface is greater than or less than the relative velocity. In particular, it is possible that the peripheral velocity of the rotating body on its outer surface is less than the relative velocity of the rotating body to the component.

The rotating body can be embodied to be substantially rotationally-symmetrical around at least one rotational axis. It is also possible that the rotating body is embodied to be rotationally-symmetrical around multiple rotational axes. For example, the rotating body can be embodied as a sphere or ellipsoid. It is also possible that the rotating body is designed as a cylinder, roller, or in general as a rolling body. In particular, an approximately cylindrical design has proven to be advantageous, since in the case of a cylindrical rotating body, for example, the acute-angled region, which contains the medium, forms over the entire width of the rotating body, so that this region is thus designed as substantially wedge-shaped. In these and other designs, the acute-angled region has a wedge shape.

However, it is not necessary for the rotating body to be embodied to be rotationally-symmetrical. Rotating bodies having elliptical or egg-shaped cross sections or rotating bodies having indentations like golf balls or having regular or irregular indentations and/or protrusions can also advantageously be used. The surface of the rotating bodies can be designed to be smooth, but does not have to be. Since the rotating bodies are not used for mounting and supporting the components relative to one another, a symmetrical and/or smooth surface is not necessary. Rotating bodies having rough and/or irregular surfaces can even be advantageous, since the wedge effect is amplified. Increased wear does not occur, because the rotating bodies are not used for mounting and transmitting load-bearing forces.

The amplification of the effect does not occur solely due to amplification or bundling of the magnetic field, but rather above all due to the particles clustered in front of the rotating bodies or rollers and the compaction thereof. Because of the magnetic field, the particles cannot move away and thus compact more rapidly to form a wedge. The wedge is externally controllable easily via switch. The advantage in the case of magnetorheological fluid such as MRF is that the wedge can disengage again by canceling out the magnetic field. The wedge can be influenced using the magnetic field—without mechanical movement or force introduction. It has proven to be advantageous for targeted influencing and reliable control that the free distance between the rotating body and the component is greater than a multiple of the particle diameter.

The diameter of the particles of the magnetorheological medium is in particular between 1 μm and 10 μm. The typical mean diameter of the particles of the magnetorheological medium is the arithmetically averaged diameter of the particles which are larger than the smallest percent and which are smaller than the largest percent. As a rule, this value corresponds to the mean value of the diameters of the largest and the smallest particle, i.e., 5.5 μm in the selected example. However, for example, if a very small number of even smaller particles are present, this does not change the typical mean diameter thus determined. This is also true if for example individual particles having 10.5 μm or 11 μm diameter are to be included.

The free distance between the rotating body and the component is preferably greater than 30 μm and in particular less than 300 μm. The typical mean diameter of the particles is preferably between 3 μm and 7 μm. The free distance between the rotating body and the component is preferably greater than 70 μm and in particular less than 250 μm.

The applicant reserves the right to claim protection for those magnetorheological transmission devices in which a free distance between the rotating body and the component is greater than the diameter of the typical largest magnetically polarizable particle. In particular, the free distance is greater than twice the diameter of the typical largest magnetically polarizable particle and can therefore be less than in the case of the otherwise identical above-described magnetorheological transmission devices.

The acute-angled region advantageously wedges the components, which are freely movable relative to one another without a magnetic field, upon application of a magnetic field. A mechanical wedge in the form of a separate fixed part is not required for this purpose.

The acute-angled region is preferably provided between the body and one component in such a manner that the acute-angled region tapers relative to the rotating body in the direction of the relative movement of the component. If a cylindrical rotating body rolls on a flat surface of one component, the acute-angled region forms in a wedge shape in front of the rotating body. A wedge which is chained together as a whole, and which inhibits the relative movement of the rotating body to the component, arises due to the chaining together of the particles in the medium.

The rotating body and in particular each rotating body is particularly preferably embodied as a separate part between the first and the second components. It is then preferable for one component as the outer component to enclose the other component as the inner component. For example, a (drive) shaft can be provided as the inner component. The other or outer component can be used for braking, for example, and can radially enclose the shaft. The rotating bodies can be provided between the shaft and the outer component. It has been shown that rotating bodies which rotate around their own axis are substantially better for achieving the wedge effect. Finished bearing shells are not necessary. The transmission of a clutch or brake torque functions independently of the quality of the rolling surfaces.

At least one separate roller bearing is preferably provided for mounting the two components. In particular, the two components are mounted so they are rotatable, and preferably so they are rotatable relative to one another, via at least two additional roller bearings. The rotating bodies ensure, with the wedge effect, the transmission of the desired torques, while the roller bearing or bearings ensure the defined guiding and support of the two components, and the uniform running gap. Because of the substantial free distance or because of the play of the rotating bodies relative to the components, tilting of the components relative to one another can occur without the use of roller bearings.

In all designs, the free distance is preferably at least 10 times as great as the largest typical particle diameter. In specific embodiments, a free distance between approximately 5 times and in particular 10 times and 20 times the largest typical particle diameter has proven to be advantageous. In the case of larger free distances, the maximum transmittable torque is reduced again, since the wedge effect subsides. In the event of excessively small free distances, a blockade can occur even without a magnetic field. In addition, disengagement of the wedge after the shutdown of the magnetic field then cannot always be ensured.

The mean particle diameter is understood as the arithmetic mean of minimum and maximum particle diameters. Most MRF have magnetically polarizable particles which have a size distribution between approximately 1 μm and 10 μm. The mean particle diameter is 5.5 μm in this example. In the case of variable size distributions, the largest typical particle diameter is understood as a particle diameter, which only fewer than 1% of the particles exceed. The largest typical particle diameter is somewhat less than 10 μm in the mentioned example, so that 10 μm can be presumed to be the largest typical particle diameter here.

The free distance is preferably greater than $1/500$ and more preferably greater than $1/250$ and in particular greater than $1/100$ and particularly preferably greater than $1/50$ of a diameter of at least one rotating body, and in particular the free distance is less than $1/10$ and in particular less than $1/20$ of the diameter of the rotating body.

The free distance is preferably greater than $1/500$ of the external diameter of the inner component and/or greater than $1/500$ of the internal diameter of the outer component. The free distance is preferably greater than 30 μm and in particular less than 200 μm.

Variations by ±20% are possible in the case of all numeric specifications. The term "particle" is understood hereafter as a magnetically polarizable particle.

If oversize rotating bodies and/or shaft diameters are used, other distances can be advantageous. An advantage of this magnetorheological transmission device having at least two components, which can be coupled, is that the wedge formation is manufacturing tolerant, i.e., for example, manufacturing-related and installation-related differences in gap heights, surfaces, and dimensions and also thermal expansions or load-related shifts of components have a subordinate influence thereon and cause negligible torque or force differences.

For example, a structurally related change of the gap within certain system limits can also be recognized by sensors and worked out by field adaptation, for example.

In preferred designs, the rotating body is part of the first or the second component. This means that the rotating body, which is embodied as a rotating body, for example, is part of the first component and rolls on the second component, for example. The rotating body can also be without mechanical connection to both components, however.

In the acute-angled region, which is wedge-shaped, for example, the ferromagnetic particles chain together in the medium upon application of an external magnetic field and result in a locally more solid formation, which opposes the further relative movement between the rotating body and the adjacent component. The particles in the wedge-shaped part can be additionally compacted in the movement direction in front of the rotating body by the rolling movement of the rotating body. However, depending on the design of the rotating body, this compaction can also be performed by pitching, tilting, or other movements relative to a component.

For example, if the rotating body rolls on the surface of one component and such an acute-angled region forms in front of the rotating body, particles in the medium are thus entrained and set into rotational movement by the outer surface due to the rotational movement of the rotating body, wherein the hardening acute-angled region strongly opposes such a rotational movement, however. The acute-angled region in wedge shape results in a force on the rotating body away from the component. Such a force and a movement resulting therefrom can optionally also be used for fine alignment purposes. A rotational movement can preferably be converted into an axial displacement of the rotating body by the acute-angled region in wedge shape when the magnetic field is activated. The rotating body is thus more or less caused to float by the particles. It is also possible to provide the rotating body or a component with thread-shaped notches, for example, or to mount them at an incline relative to one another, in order to change the action direction of the resulting force or to further increase the achievable force transmission. A linear movement can thus be converted into a rotational movement using a type of threaded rod. The relative movement is inhibited by application of a field.

It is also preferable for the rotating body to be embodied as a separate part between the first component and the second component. Such a design can be particularly advantageous, since two acute-angled regions or wedge-shaped regions can occur between the rotating body and the two components. If the rotating body practically presses against the first component on one side and practically presses against the second component on the other side, acute-angled regions, which are subjected to the magnetic field of the magnetic field generating unit, form on both sides. The action is thus increased. It is not necessary for this purpose for the rotating body to press completely against the first component or the second component. A small gap remains between the rotating body and the respective component. The size of the gap is dependent, inter alia, on the properties of the medium. In particular, the size of the gap can be at least 5 times, and preferably at least 10 times or 20 times a typical or mean particle diameter.

The ferromagnetic particles consist in particular of carbonyl iron powder. The fluid can be an oil, for example.

It is also possible that magnetorheological and electrorheological media are used jointly. The use of other media which are influenced and chained together, for example, by corresponding fields is also conceivable. The use of media which change their rheological properties depending on other physical variables such as temperature or shear velocity is also possible.

The channel can be completely or also only partially filled with the medium. At least the acute-angled region of the channel is preferably filled with the medium.

In all embodiments, the first and/or second component can be embodied to be rotationally symmetric. For example, the components can each be embodied as plates or cylindrical bodies, between which rotating bodies are provided, in order to increase the effect of the magnetic field of the magnetic field generating unit accordingly through the wedge effect.

In all embodiments, it is preferable for the magnetic field to run through the rotating body and in particular substantially transversely to the relative movement of the components relative to one another and from one component to the other component at least partially through the rotating body. Such a design has proven to be particularly effective, since the action of the magnetic field at the transition points from the rotating body to the walls of the channel is particularly strong. Depending on the acting magnetic field, it is therefore advantageous if the rotating body is at least partially magnetically conductive. In particular at least one component and in particular both components and/or the at least one rotating body are made at least partially of a ferromagnetic material. The permeability coefficient is preferably greater than 500. The permeability coefficient of the material, which is also referred to as the relative permeability, can also be 1000, 2000, or more. Rotating bodies made of ferromagnetic steel, such as ST37, are possible, for example.

Demagnetization of the material can be performed by a damped magnetic alternating field, so that a lower base torque is achieved without residual field.

In all embodiments, it is preferable for the magnetic field generating unit to comprise at least one permanent magnet and/or at least one coil. The use of one or more permanent magnets and one or more electrical coils is also possible.

It is possible and preferred to permanently change the magnetization of the permanent magnet by at least one magnetic pulse of an electrical coil. In such a design, the permanent magnet is influenced by magnetic pulses of the coil such that the field strength of the permanent magnet is permanently changed. The permanent magnetization of the permanent magnet can be set by the magnetic pulse of the magnetic field generating unit to an arbitrary value between zero and the remanence of the permanent magnet. The polarity of the magnetization is also variable. A magnetic pulse for setting a magnetization of the permanent magnet is particularly shorter than 1 min. and preferably shorter than 1 second and the length of the pulse is particularly preferably less than 10 ms.

As an effect of a pulse, the shape and strength of the magnetic field are permanently maintained in the permanent magnet. The strength and shape of the magnetic field can be changed by at least one magnetic pulse of the magnetic field generating unit. The permanent magnet can be demagnetized by a damped magnetic alternating field.

For example, AlNiCo is suitable as a material for such a permanent magnet with variable magnetization, however, other materials having comparable magnetic properties may also be used. In addition, it is possible to produce the entire magnetic circuit or parts thereof from a steel alloy with strong residual magnetism (high remanence) instead of a permanent magnet.

It is possible to generate a permanent static magnetic field using the permanent magnet, which can be overlaid by a dynamic magnetic field of the coil in order to set the desired field strength. The current value of the field strength can be varied arbitrarily by the magnetic field of the coil. The use of two separately activatable coils is also possible.

In all the configurations it is preferable to provide at least one control device for the magnetorheological transmission device. The control device for the transmission device is preferably provided by the control device of the input device. Alternately, the transmission device may comprise its own control device, which is in functional connection with the control device of the input device.

The use of an energy store, for example, a capacitor for storing at least a fraction of the required energy is also possible. At least one sensor or multiple sensors can be used for detecting relevant data, for example, the relative velocity of the components in relation to one another or the prevailing field strength and the like. It is also possible to use a temperature sensor as the sensor, which triggers an alarm if predetermined temperature conditions are exceeded, for example. A rotational angle encoder can advantageously be used to have data about the angular position of the components in relation to one another at any time. Such a sensor for the transmission device is preferably provided by the sensor means of the input device. Alternately, the transmission device may comprise its own sensor, which is in functional connection in particular with the sensor means and/or with the control device of the input device.

In all designs, it is preferable for the permanent magnet to at least partially consist of a hard magnetic material, whose coercive field strength is greater than 1 kA/m and in particular greater than 5 kA/m and preferably greater than 10 kA/m.

The permanent magnet can at least partially consist of a material which has a coercive field strength less than 1000 kA/m and preferably less than 500 kA/m and particularly preferably less than 100 kA/m.

The presently described magnetorheological transmission device can preferably be embodied as part of a bearing, a brake, a clutch of an operating knob or control knob, or a shock absorber, or the like. The use as a steering wheel lock is also possible, wherein continuous generation of the required field strength is ensured by a permanent magnet.

The rotating body and at least one component can touch on at least one point or at least one line. It is possible and preferable for the rotating body to be at rest relative to at least one component.

The rotating body can preferably move relative to at least one component, for example, in the form of a rotational or tilting movement.

The field strength can have a strong gradient depending on the respective distance between rotating body and components.

The field strength preferably increases in the acute-angled region between rotating body and components toward the region having the least distance.

An antitheft device in the form of a steering wheel lock to protect from vehicle theft is also possible, for example. The steering column is blocked by a strong increase of the torque, for example. For this purpose, a permanent magnet can generate a permanent magnetic field, whereby a relative movement of the steering rod in relation to the steering column is made much more difficult. In conventional steering wheel locks, the locking bolts are sheared off in the event of an overload, after which free movement of the steering rod is possible. In contrast thereto, the provided force is maintained in the case of this solution, even if it has been exceeded once.

The presently described magnetorheological transmission device in the form of a clutch or brake or the like, for example, has a considerably greater effect with a considerably smaller space requirement. The ratio of the installation space requirement to the prior art can reach or exceed a factor of 10. The use of a magnetorheological fluid as the medium in a magnetorheological transmission device as presently described allows the cost-effective production of a clutch or a brake or the like. The need for maintenance can be substantially reduced, since few and simple parts are used. If necessary, the maintenance can be carried out by simple replacement of the magnetorheological fluid. The construction is simple and robust and power feedthroughs are not required. In addition, the power demand is less than in the prior art, because the wedge effect substantially contributes to influencing the relative movement of the components. MRF brakes or MRF clutches with a torque/weight ratio of >100 Nm/kg are thus possible.

In magnetorheological clutches or brakes according to the prior art, the magnetic field poles move relative to one another and generate shear forces (direct shear mode) in the interposed MR fluid. The shear forces vary depending on the magnetic field. No magnetic field means no or low shear forces (no chain formation in the MRF), maximum magnetic field means maximum shear forces and therefore maximum braking force or braking torque. In simplified form, magnetic field and shear forces are proportional.

In the presently described transmission apparatus, through appropriate design of the individual components, dimensioning, and field introduction, very advantageous behavior which deviates therefrom can be provided. This advantageous behavior is expressed in that a substantially lower magnetic field, and therefore a lower current strength are required for maintaining the acute-angled embodiment or the MR fluid wedge than is required for the initial generation of the wedge. This is because the particle cluster no longer falls apart so easily once it has first been accumulated and has been quasi-mechanically compacted by the special movements fundamental to the presently described transmission device under the influence of a correctly introduced magnetic field. As a result, for example, after a corresponding time for achieving this state, a braking torque can be maintained using the fraction of the magnetic field or electrical power (coil current), respectively, which is energetically advantageous.

If clutches having magnetorheological fluids according to the prior art are loaded beyond the maximum transmittable clutch torque, individual particle chains begin to break apart, whereby slip or slipping through results. The maximum clutch torque is maintained, however, or sometimes even slightly increases, and the clutch does not disengage. Depending on the application, this can be undesirable, for example, if a drillbit of a drill jams during drilling.

In the presently described magnetorheological transmission device, appropriate design of the individual components, dimensioning, and field introduction, can provide very advantageous behavior which deviates therefrom. This advantageous behavior is expressed in that in the event a maximum force is exceeded between the moving parts, the wedge (material accumulation) generated by the magnetic field is suddenly pressed through the gap (material displaced) and the force therefore decreases suddenly at the same time. Because of the relative movement resulting therefrom and the high applied force, a new wedge does not form, whereby the relative force remains low. In the case of overload clutches, this behavior is very advantageous. The maximum force (triggering force) or the maximum torque (triggering torque) can be preset via the magnetic field.

Furthermore, unmixing, sedimentation, and centrifugal force problems are reliably prevented, since continuous mixing of the particles in the medium is achieved by the rotating rotating bodies.

Because of the substantially higher transmittable torques and forces, clutches, brakes, or the like having substantially smaller diameters can be implemented. Because of the small MRF channel height and the rotational movement of the rotating bodies, unmixing is practically not relevant in the case of the presently described magnetorheological transmission device.

The presently described magnetorheological transmission device can be used in manifold ways, thus, for example, in prostheses as a joint for rotating components and as a damper in the case of a linear movement. The use on a vehicle door is also possible, in order to allow variable stops or defined standing open of the door. The use as a turn signal lever on vehicles or as an overload function on machine tools is also possible, in order to allow precise disengagement of the clutch if a limiting torque is exceeded.

Such a clutch can be used to keep the torque or speed at the output independent of the drive, for example, in order to keep the speed constant or to not exceed a specific torque. It can also be used for intended purposes, in which a high torque is to be transmitted, thus, for example, in the torque allocation on a drivetrain.

Further possible uses are clutches in electrical drives in order to connect a load in a controlled manner, NC milling machines, wood processing machines, automation facilities, and use in industrial robots, sheet-metal processing machines, printing presses, textile machines, power looms, winding devices, hay balers, car loaders, electric window regulators, garage doors, roller blinds, etc., and in rapid milling cutters, food processors, mills, and the like.

For example, if a medium such as paper, thread, or the like is to be wound with uniform tension onto a roll, this can be achieved with the presently described transmission device by varying the drive or braking torque in accordance with the diameter change of the winding roll. Further fields of use are adaptive brakes in fitness devices (e.g., rotation: bicycle trainer; treadmill; levers in weightlifting, rowing machines; linear movement: lifting weights, clamping the linear vertical adjustment of a saddle or office chair or the longitudinal adjustment of a steering column or a seat in a vehicle).

The presently described transmission device can also be used in the case of a three-dimensional movement. The rotation and pendulum movement can thus be restricted or blocked by the MRF wedge. The acting torque is continuously adjustable and switching times in the range of a few milliseconds can be achieved. The construction is simple and no mechanically moving parts are required for varying the torque. A further advantage is that almost noiseless operation is possible. The additional costs are low and a magnetorheological transmission device can be designed to be operationally reliable, for example, if a permanent magnet with remanence is used for setting a magnetic field. The wedge effect enormously amplifies the action, so that a smaller installation space is achievable.

In all designs, the rotating bodies do not have to be smooth, but rather can have rough or uneven surfaces.

Use of the presently described transmission device as a haptic rotary knob is also possible. A rotary knob or a type of potentiometer can thus be practically implemented. The field of use is manifold and comprises, for example, controllers for crane operation or the like. The rotation can be controlled so it is stiffer depending on load. It can also be controlled as a function of the load height.

The use in "force feedback" applications or in "steer by wire" applications is also of interest. The use in operating elements in vehicles, car radios, stereo systems, etc., is also possible.

In all embodiments, it is also possible to use magnetic seals for sealing the presently described transmission device, in addition to a seal with a sealing lip. The seal can be produced via a permanent magnet. Advantages of such a design are smaller base forces, freedom from wear, and the permissibility of greater manufacturing tolerances. In addition, defined overload behavior exists, since a defined breakthrough occurs if the overload is exceeded. It is possible to use such a seal in front of or behind such a device or to use it in front and behind.

A significant advantage of the magnetic seal is the very low friction; however, it can be necessary to use still a further seal, since such a seal possibly only holds back MRF particles and permits oil as the base liquid to pass through the gap over time, for example. Therefore, such a magnetic seal can be used as an outer seal, in order to hold back MRF particles. A further classic seal only seals off the carrier medium, for example.

A movement of the magnet can be used to achieve lubrication in the MRF, as well as material transport and cooling, for example, via hydrodynamic effects. In addition, a flow away from the seal can be achieved and pressure differences can be dissipated.

In order for example to set the play between two parts or to remove play from a design and to compensate for manufacturing tolerances, for example, a force or an axial force and/or a radial force can be used, which is induced by an MRF wedge effect.

The running profile of ball bearings or roller bearings or needle bearings can be reduced down to zero by the wedge or the buildup of a wedge or an MRF layer. This functions very well in particular with inclined contact ball bearings or tapered roller bearings, since the play is preset or settable by the design here. If there is a large amount of play, axial travel can be forced during the buildup of the wedge. In this application, the MRF wedge effect is not used as a clutch or as a brake, but rather to set the bearing play.

In refinements, it is possible for a radial or axial force, for example of an inclined contact ball bearing, to act against a spring or a yielding element, such as for example rubber. It is not only possible to work between two fixed delimitation surfaces, but rather also for one fixed stop and one spring-loaded stop to be used. A greater adjustment range and lower spring stiffness can thus be achieved.

The MRF wedge or an MRF wedge can be generated by a magnetic field of a magnet. A permanent magnet can be adjustable by hand or it is also possible to displace or rotate the permanent magnet or a shield by hand or using actuators, in order to increase or decrease the field strength in the relevant region. An arbitrary part of the magnetic circuit can be moved relative thereto in order to influence the magnetic field acting in the MRF wedge.

A mechanical fine or coarse alignment and therefore also setting of the braking effect can be possible. Such a setting can be provided, for example, to compensate for physical variables such as temperature, pressure, speed, or the like. It is also possible to compensate for tolerances or installation inaccuracies.

In all embodiments, it is preferable to provide a settable permanent magnetic field strength via remanence. In preferred embodiments, a bearing having the presently described transmission device has no or only minimal residual magnetism (remanence) itself. Otherwise, a position-dependent counterforce of different strengths can occur, since the parts move in relation to one another.

In advantageous designs, the remanence material is to be arranged in a general region of the bearing, which is permeated by the magnetic field in a particularly position-independent manner, thus, for example, the inner shaft or the outer envelope, etc.

However, it is also preferable to use the effect of the position-dependent magnetization, in that, e.g., the inner running surface having remanence is used in order to generate specific detent torques, for example. This can be performed, for example, for haptic feedback about variable detent torques with respect to their strength, the rotational angle, or the end stop or the like. Not all bearing balls have to be ferromagnetic, depending on the desired setting capability.

It is also possible to provide a magnetorheological transmission device with a design deviating from the classic bearing construction. For example, the direction of the magnetic field can also be aligned at least partially or completely approximately parallel to the axis. At least partial alignment parallel to the rotational direction or movement direction or in the tangential direction is also possible. It is also possible that the entire magnetic circuit is arranged nearly or completely in the interior.

The material of the magnetorheological transmission device does not have to be completely ferromagnetic, depending on the desired application or magnetization, respectively, it can be advantageous if individual parts of the magnetorheological transmission device are not ferromagnetic or are only partially ferromagnetic, respectively.

Depending on the application, it is also conceivable to manufacture at least one part from different materials, to obtain locally differing magnetic properties.

One possible embodiment is a rotary knob with an integrated rotary encoder and a magnetorheological transmission device with wedge effect. The position or the rotational angle of the rotary knob can be determined via the rotary encoder and the rotational resistance can be varied in a wide range. Thus, for example, a haptic interface with variable detent torques and arbitrarily settable end stop can be constructed, which changes its properties depending on the currently selected menu. A low or high torque and/or small or large pattern/ripple and also a variable pattern—depending on the menu to be operated—can be set. The curve of the torque increase and decrease can be set or varied depending on the situation, for example, as a square-wave, sinusoidal, sawtooth, or arbitrary curve. A stop can also be simulated. The stop can be hard or can have a predefined or situation-dependent torque curve.

The rotary knob as one component is preferably fixedly connected to the shaft as the other component, which is in turn mounted so it is rotatable in the housing. The relative movement or relative position is detected via a rotary encoder, for example, via a magnetic, optical, or (via buttons) mechanical incremental encoder. A potentiometer with slip contacts can also be used, but only specific rotational angles are typically permissible using such a potentiometer.

A sealing ring is advantageous, so that the magnetorheological fluid remains in the housing. The seal can also only consist of permanent magnets or a combination of permanent magnet and typical seal.

The inner region, i.e., the volume enclosed by seal and housing, is at least partially filled with a magnetorheological fluid.

The housing is preferably designed as a pot, i.e., it is closed on one side. Only one sealing ring is thus required. A continuous shaft (two-sided shaft) is also conceivable.

The coil can generate a magnetic field, wherein the magnetic circuit is closed via the housing, the shaft, and the magnetorheological transmission device. The magnetic field required for the wedge effect can thus build up in the magnetorheological transmission device. The coil is advantageously fixedly connected to the housing, which makes the cable guiding easier.

The construction is robust and can be designed so that almost no magnetic scattered fields are generated outside the housing. However, many other construction variants are conceivable, which can have specific advantages depending on the application.

For example, the coil can also be arranged outside the housing, wherein the magnetic field then acts through the housing on the magnetorheological transmission device. No mechanical connection is necessary between coil and housing, the coupling of the magnetic circuits is sufficient to influence the magnetorheological transmission device in the housing. In particular, the coil does not have to be permanently located on or in proximity to the housing and can be designed such that it can be removed from the housing as a separate unit. Permanent magnets can also be provided in the magnetic circuit.

In a preferred embodiment, the rotary knob can be electromagnetically driven, for example, and can also actively exert a force (force feedback) to be able to statically generate a specific counter torque. In this design, a better torque to installation space ratio is achieved than in many designs according to the prior art. In addition, the production costs are low because of the simple construction, since, for example, the rolling surfaces of the components do not have to be high-precision in haptic applications and also typically do not have to withstand high speeds and a large number of revolutions. In general, the magnetorheological transmission device described here has a very low base friction (OFF state). A battery and a control command transmission unit (radio, WLAN, Bluetooth, antenna) are preferably also integrated in the actuator or rotary knob, respectively. The haptic knob can be placed anywhere and does not require a wired control connection or power connection. The MRF wedge principle requires very little current (power) in relation to the torque. It is therefore also well suitable for battery operation or for wireless power supply. Both the required power and also control commands and, for example, measured values from sensors such as rotational angle can also be transmitted wirelessly.

A preferred embodiment manages without a battery and receives the power required for the function by means of inductive coupling. Embodiments are also particularly preferred which acquire the power required for operation directly from the environment and buffer it locally (energy harvesting). Thermoelectric generators, solar cells, elements which convert vibrational energy into electrical power, and others, as well as corresponding local energy stores are possible for the energy conversion. It is also conceivable to use the movement of the magnetorheological transmission device itself for the power generation.

If a magnetic field is applied to the presently described magnetorheological transmission device at least partially via a permanent magnet, and the magnetization of the magnetic field is permanently changed by at least one magnetic pulse of at least one electrical coil, several advantages result. In specific cases, for example, through the utilization of the remanence and the pulsed operation of a coil, which does not always have to be energized, weight and space advantages can be achieved. The wires of the coil can be dimensioned thinner and lighter, because they must respectively only be energized for a short operating time. Advantages can thus result in the case of weight, power demand, space requirement, and costs.

Therefore, it can be advantageous in specific applications that due to the pulsed operation of the electrical coil, it can be implemented significantly smaller than if it must be designed for 100% activation time. The heating of the coil typically does not play a role in pulsed operation, since short-term power loss peaks are buffered by the intrinsic heat capacity of the coil and the parts surrounding the coil. Very high current densities in the windings can thus be tolerated or thinner lines can be used, as long as the mean power loss remains acceptable over longer periods of time.

In the case of a smaller coil, the resulting magnetic circuit surrounding the coil can also typically be smaller, because of which a comparatively large amount of installation space, material, weight, and costs can be saved. Only the power expenditure for a single pulse increases, which can be very well tolerated depending on the application, however. Overall, a large amount of power can nonetheless be saved in comparison to a continuously energized coil.

In all designs, it can be possible to implement the power supply in a wireless manner. The power can be supplied, for example, from the power source to the power electronics or from the power electronics to the coil, respectively, via an electrical, magnetic, or electromagnetic coupling, for example, a radio link. In the application in a bicycle, the power can be supplied externally via a docking station, for example. The power supply via a power source on a bicycle, for example, to all consumers (forks, rear shock absorbers, display) is also possible. The power can also be supplied similarly in the case of a ski boot, ski, mobile telephone, or to the sensors.

A power supply via radio can possibly have worse efficiency than typical wiring. In addition, the power transmission and its range can be limited. However, such advantages do not interfere depending on the application. It is advantageous that no wear of the contacts occurs. The power transmission is typically secure from incorrect polarity and short-circuit-proof, because only limited power is present on the secondary side. Furthermore, wire breaks are not possible and the device is more movable as a whole.

In such designs, however, it is advantageous to buffer the power for at least one pulse in a capacitor or energy store. The power supply of the system can thus have a smaller power, since short-term power peaks of a pulse can be absorbed by the capacitor. In addition, a discontinuous or pulsed power supply can also be used.

One possible construction step of the presently described transmission device is a fully autonomous system, which is wirelessly supplied with power. For example, application in a bicycle is conceivable, wherein the system is supplied with power by at least one small magnet on a tire.

In general, arbitrary "energy harvesting" units can thus be used for the power supply, for example, solar cells, thermoelectric generators, or piezocrystals. Elements which convert vibrations into energy can thus also be used very advantageously for the supply.

An embodiment is also conceivable similar to an electric toothbrush, in which the power supply is performed by inductive coupling. For example, the battery can be inductively charged, without damaged cables or corroded or soiled contacts obstructing the charging procedure. Power can be transmitted via a magnetic resonance over longer distances.

The power supply of the remanence pulse can be performed via induction, as in the case of electric toothbrushes. The combination of the MRF wedge principle with remanence is particularly power saving and advantageous.

A loudspeaker or a noise generating unit can also be integrated or assigned. This is advantageous, because the rotary knob as the MRF wedge knob is mechanically noiseless per se. Both the rotation without and also with pattern and/or the virtual stops are noiseless per se. The generation of the MRF wedge for a torque increase or to generate a pattern is also noiseless per se. By means of the noise source, such as a loudspeaker or a piezo loudspeaker, for example, a click can be associated with the virtual pattern at each detent position. The type, volume, and duration of the noise can be individually assigned, but can also be changed or turned off if the user wishes.

Therefore, the torque, the pattern, the stops, and the noise are programmable or adaptive, respectively. The noises can also be generated via external loudspeakers, for example, standard loudspeakers in the automobile or the loudspeakers of the stereo system in the home.

The haptic knob can therefore practically replace the mouse wheel of a computer mouse. In the case of the pattern, not only the angle interval of the pattern can be settable, but rather also its curve shape, thickness, etc. A pattern characteristic curve can therefore more or less be predefined.

The haptic rotary knob can also be installed on an operating panel or on a display screen. In order that the display screen does not have to be removed for fastening the knob, it can consist of an upper part on the display screen and a lower part below the display screen. Data transmission via induction or the like, for example, is preferably provided. The display screen can thus be produced more cheaply as a surface.

It is also possible that an MRF haptic knob can also be pressed. The pressing can also act through an MRF, whose properties are variable via a magnetic field.

The display screen indicates the information to be set, which changes depending on the application. The function of the haptic knob adapts itself thereto. In one case, adjustment is made by means of a pattern (for example, setting the volume; a volume scale appears on the display screen, which can also have a logarithmic scale).

In another case, an adjustment can be made between two positions without a pattern, but with variable torque, thus, for example, between the clock setting 8:00 and the clock setting 16:00, wherein an increasing torque can be provided in each case before the end position. The pattern can also be used for approaching defined positions, for example, if a name input is requested.

The display screen can also be embodied as a touchscreen. Menu points can thus be rapidly selected and fine settings can be made by means of the rotating actuator. For example, it is not desirable in the case of automobiles to control the volume of the radio via touchscreen, since the driver must otherwise always look down for a long time at what and where he is currently adjusting, which distracts him. He can find the rotating actuator with a brief glance or even without looking at it.

The adjustment using a mechanical actuator is also simpler and safer than via a touch display when bicycling, for example. This is true in particular even if the bicyclist is wearing gloves, for example, whereby the operation of a touch display is more difficult or even impossible.

A combination of a display screen or touch display and a mechanical rotating actuator with variable torque/pattern is also possible. Such input devices can also be advantageous outside the motor vehicle, thus, for example, in the case of controllers for industrial plants, remote controls for televisions or radio vehicles such as toy helicopters, for example, and on PCs and games consoles, and control consoles for military applications (drone aircraft, rockets).

It is also possible that a haptic rotary knob with a display replaces the current computer mouse.

It is possible that the rotary knob or the actuator can be countersunk in the normal state and is only extended if needed.

It is also possible to embody such a structural unit as a slide regulator, in particular in combination with a linear MRF wedge unit.

It is also possible to equip a magnetorheological transmission device with one or more poles and one or more protrusions. In all designs, it is possible that protrusions or the like, which protrude from one component in the direction toward the other component, for example, are provided between the two components of the magnetorheological transmission device.

Such a design is possible and preferred both in the case of rotational mobility and also in the case of linear mobility of the two components to one another.

Only one protrusion can be provided or multiple protrusions can be provided. It is possible that a ball or a roller or another rotating body, which is at least partially accommodated by the protrusion, is arranged on at least one protrusion.

If protrusions are provided on one component, it is preferable for at least one pole or at least one magnetization unit or at least one magnet or one coil to be provided on the other component. The number of the magnetization units or poles can be 1 or can also be greater.

The shape of the protrusions can fundamentally be arbitrary and can be semicircular, tapered, or blunt, for example. The receptacle region of rotating bodies is preferably accordingly embodied as rounded.

One or more magnetization units or poles can be embodied as electric coil plus core or as a permanent magnet or can consist of remanence material or a combination thereof.

The intervals between individual protrusions and/or magnetization units are preferably approximately uniform, but can also be arbitrary.

The depth, i.e., the radial extension or the axial extension of individual protrusions or magnetization units to others can be different.

The field strength which is applied to or acts on the individual magnetization units can in particular also vary at the same time.

The speed of the rotating bodies does not have to be equal to the rolling speed, it can also deviate therefrom, for example, by step-down or step-up transmissions. The inner part which is embodied by the protrusions, for example, as star-shaped, can be mounted off-center to the outer part.

One application of such a magnetorheological transmission device can be, for example, as a haptic knob with pattern or in furniture and drawer guides with positions.

The magnet or each magnetization unit or the inner part and/or the outer part can also consist of remanence material.

If it is used on a steering column, the device can be used for the purpose of braking the steering around the middle location, so that, for example, in the case of power steering which is intrinsically smooth, the steering becomes stiffer, which is advantageous during straight-ahead travel on a freeway, for example. A magnetorheological transmission device can brake such smooth steering and thus increase the driving comfort, through a torque which is adapted to the respective situation or user.

It is also possible to make other steering procedures safer, for example, by implementing end stops using a magnetorheological transmission device. Therefore, functions are also made possible in the case of hydraulic steering systems, which could previously only be implemented via electronic steering systems.

Since magnetorheological fluids chain together very rapidly upon the application of a magnetic field, it can be sufficient in the normal state, for example, during car driving, if the magnetic field is turned off. It is typically entirely sufficient to only turn on the field when a first rotational angle change is initiated. A significant amount of power can thus be saved.

Alternatively thereto, a base torque can be implemented with remanence. When a rotational angle change is registered, a dynamic magnetic field can be built up, which can also pulsate to generate a virtual pattern.

In all designs, it is possible to implement an adaptive door brake, for example. For this purpose, a parking distance can be measured in the case of a motor vehicle during parking, for example. The distance to the adjacent motor vehicle can be calculated from the data. The maximum angle to which the door can be opened can in turn be calculated therefrom and the opening procedure can be braked accordingly upon reaching this angle or even before.

For this purpose, the sensor or the sensors for measuring the distance from the vehicle during parking can be used, so that separate sensors are not necessary. It is also possible to perform the control so that the door initially opens easily and then a pattern occurs, which becomes finer and finer. A haptic display for door openers would thus be practically implemented, which indicates when the stop is approached.

It is also possible to hold open doors, windows, or the like at specific angles. This can be implemented in the case of motor vehicles or also in the case of furniture, for example.

In embodiments in which the remanence is utilized, the magnetic field for the remagnetization can be externally applied. A corresponding coil, which acts through a cylinder, for example, can be used for the remagnetization.

The applicant reserves the right to claim a method wherein the coupling intensity of at least two components, which can be coupled, is influenced, using a magnetorheological transmission device, wherein the coupling intensity is influenced in at least one channel which contains a magnetorheological medium with magnetically polarizable particles, which can be influenced by a magnetic field, and wherein at least one magnetic field is generated in the channel using in particular at least one magnetic field generating unit in order to influence the magnetorheological medium in the channel using the magnetic field. At least one rotating body is in particular provided in the channel and a free distance between the rotating body and the component is in particular greater than 10 times the diameter of the typical mean magnetically polarizable particle. At least one acute-angled region which contains the magnetorheological medium is provided in particular between the rotating body and at least one component. The magnetic field of the magnetic field generating unit is in particular at least temporarily and at least partially applied to the channel, in particular in order to optionally chain together the particles and/or wedge or release them with the rotating body.

Several additional inventive features appear in the claims. Various inventive features are contained in the specification, without being specifically recited in the claims. By way of example, the input device may be designed with a controller that is suitable and configured to actuate the brake device, depending on a pivoting angle of the operating lever obtained by sensors.

In accordance with a further feature of the invention, the controller is configured to provide the increased deceleration torque for overcoming the pivoting angle range in one direction only, so that, after overcoming the pivoting angle range, the operating lever can be returned absent such increased deceleration torque.

In accordance with a further feature of the invention, the controller is configured to fix the operating lever in specified detent positions, and for this purpose to perform controlled increasing of the prevailing deceleration torque by means of the brake device, so as to prohibit any further movement or resetting, without applying additional force and/or without any additional user action.

Also, the controller may be configured to increase the deceleration torque, already starting at a defined pivoting angle prior to reaching a detent position, and/or to decrease it, starting at a defined pivoting angle after leaving the detent position.

In accordance with a further feature of the invention, the controller is configured to block the operating lever, when at least one specific pivoting angle is reached and/or in the neutral position and/or in the current position, so that a manual force to be applied operationally cannot cause any further movement in at least one pivoting direction and/or in all the operational pivoting directions.

In accordance with a further feature of the invention, the controller is configured to decelerate and to enable the pivoting motion of the operating lever by means of the brake device in a controlled sequence, and in order to realize such a sequence, to set different levels of deceleration torques for the deceleration and enabling, and to set the deceleration torques for the deceleration and/or the enabling as a function of the time and/or as a function of the pivoting angle.

In accordance with a further feature of the invention, the controller is configured to start the deceleration torques of the sequence dependent on the angle, and to maintain it dependent on the time, and in particular to skip setting a deceleration torque provided in the sequence, when an angular position provided for the start is overrun while the deceleration torque is being maintained.

In accordance with a further feature of the invention, the controller is configured to set the different deceleration torques of the sequence at such a frequency that the pivoting motion of the operating lever is damped by way of controlled vibrations, and wherein the frequency is preferably at least 50 Hz.

In accordance with a further feature of the invention, the controller may be configured for dynamic adjustment of the different deceleration torques of the sequence over the time, and/or the pivoting angle of the operating lever, and/or the motion speed of the operating lever, and/or the quantity of previously performed settings of deceleration torques.

In accordance with a further feature of the invention, the controller is configured to set a sequence showing continuously changing deceleration torques, and wherein in particular a sinusoidal or cosinusoidal path is provided for this purpose.

In accordance with a concomitant feature of the invention, the controller is configured, when the operating lever is actuated after a defined time of no actuation of the operating lever, to emit at least one haptic warning signal, and for this purpose to preferably set a defined sequence of deceleration torques.

Other features which are considered as characteristic for the invention are set forth in the appended claims.

Although the invention is illustrated and described herein as embodied in an input device and method for operating an input device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
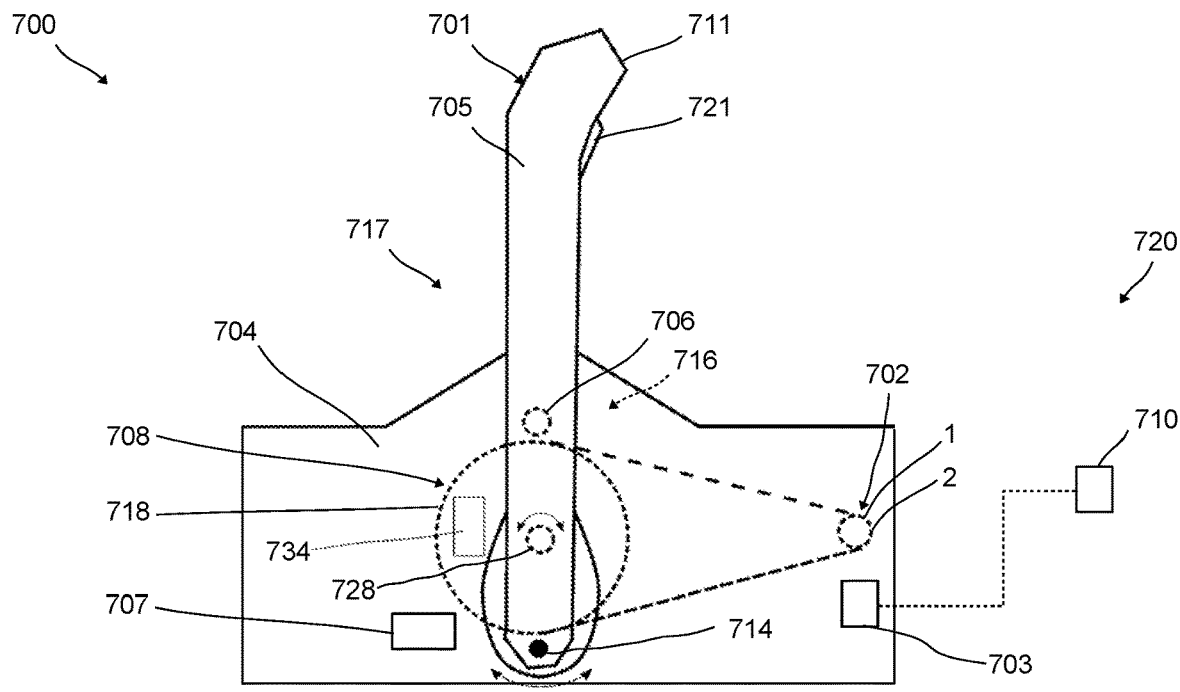
FIG. 1 a partial cutaway side view of a purely schematic illustration of an input systems including an input device according to the invention.

Referring now to the figures of the drawing in detail and first, particularly, to FIG. 1 thereof, there is shown an input device 700 according to the invention, configured as a joystick 711, which is part of an input system 720, and which is operated using the method according to the invention. Moreover the input system 720 comprises an input receiving unit 710 coupled with the input device 700, which is for example configured as a utility vehicle or as a computer. The input device 700 allows to make entries in the input receiving unit 710. The operating lever 705 is equipped with a switch 721.

The input receiving unit 710 does not need to be directly wired with the input device 700, it may be connected through a radio system or signaling system or a network. Also, the input receiving unit 710 can be spatially remote from the input device 700, e.g. for controlling an unmanned aircraft (e.g. drone).

The input device 700 comprises an operating device 701 with an operating lever 705. The operating lever 705 is presently accommodated on a supporting structure 704 for pivoting around two or more pivot axes 706, 728. The pivot axis 706 is shown separate from the pivot axis 728 for better comprehensibility. The two axes 706, 728 are oriented orthogonal to one another and the cross through one another. That is, they form the axes of a x/y two-axis gimbal support, having a single z-axis. Moreover the operating lever 705 is attached to the supporting structure 704 by means of a joint 714. After actuation, a resetting unit 707 can return the operating lever 705 to a neutral position 717.

Damping the pivoting motion of the operating lever 705 is controlled by a magnetorheological brake device 702 (also referred to as MRF-brake). For this purpose the brake device 702 is coupled with the pivot axes 706, 716 via one or more transmission stages 708. The transmission stage 708 is configured as a belt drive 718.

This brake device 702 is for example configured as a rotary damper 1 or as a magnetorheological transmission device 2.

The pivoting motion of the operating lever 705 is transmitted to a rotation axis 728 of the belt drive 718, and via the belts, to the brake device 702. Thus, the brake device 702 is caused to perform a rotational movement as the operating lever 705 pivots.

Figure 2:
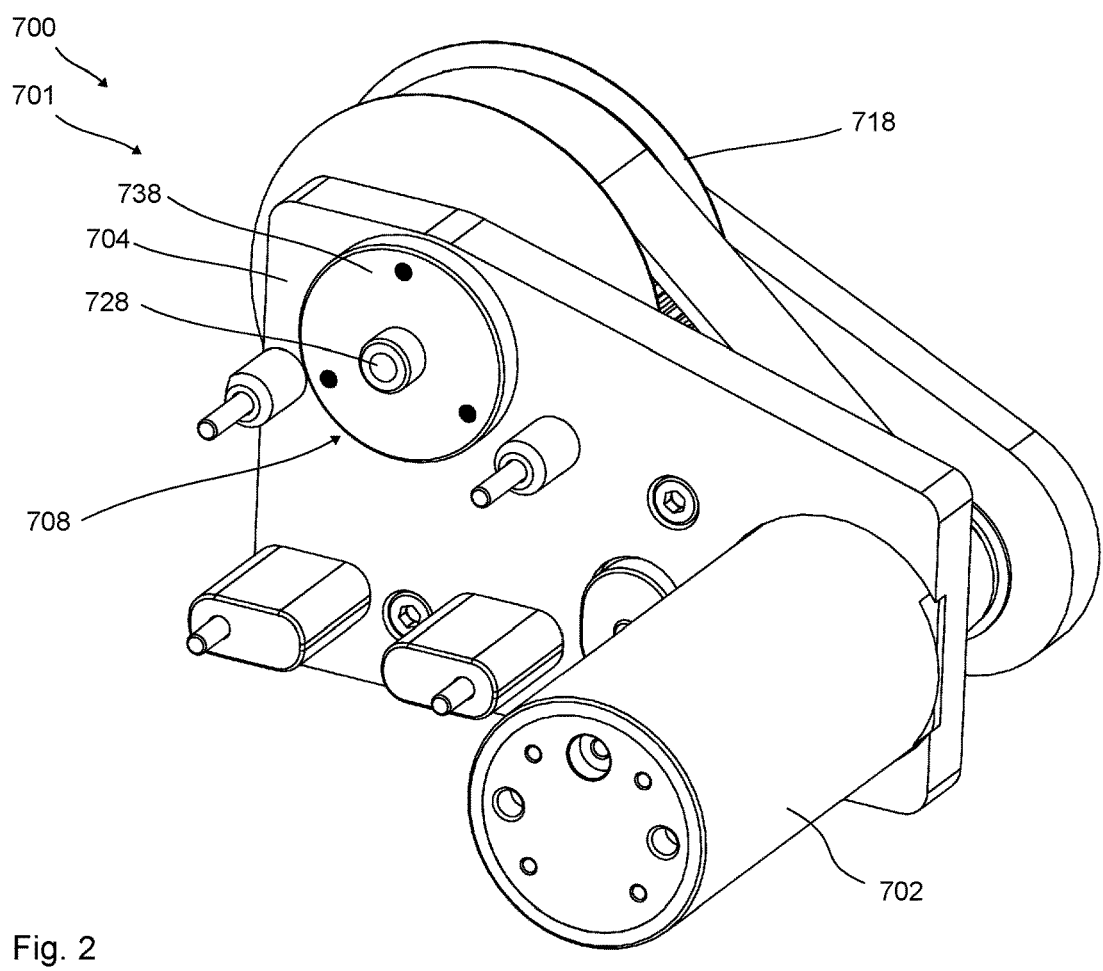
FIG. 2 a perspective view of a detail illustration of the input device of FIG. 1.

It will be understood that, in principle, the device illustrated in FIG. 2 is functionally disposed in two orthogonal directions. Only one directional pivot/brake is shown in FIG. 2, such as pertaining to the X-axis. A corresponding system is provided for the Y-axis, rotated by 90 degrees relative to the X-axis.

The transmission stage 708 and the supporting structure 704 and also the brake device 702 are illustrated in detail in the FIG. 2. Here the force transmission from the operating lever 705 to the shear damper, which is elongated and cylindrical, of the brake device 702 is shown on the bottom right, in the front in the figure. The operating lever 705 is flange-mounted to the wheel 738 on the top left, so that during pivoting, it sets the transmission 708 and the shear damper rotating via the toothed belt.

The brake device 702 is selected by a controller 703, referred to as a control device 703 below, so that the deceleration torque can be adapted to the current operational situation. For this purpose the pivoting angle of the operating lever 705 is detected by means of a sensor means 734. The sensor means 734 comprises e.g. an encoder, rotary encoder, Hall sensor, or other suitable sensor. The sensor e.g. detects an absolute or relative position. The pivoting angle of the operating lever 705 is detected e.g. via the angular position respectively the rotation angle of the brake device 702 or of the transmission stage 708.

This allows to generate a haptic signal, which can be perceived in the operating lever 705, and e.g. a defined sequence 713 of deceleration torques. Thus, the user receives, as a result of an input made and/or while making an input, a haptic feedback (so-called force feedback). The haptic signal is generated by the control device 703 as a result of a control command. The control command is for example lodged in the control device 703, e.g. as an angle dependent function, or is generated therein, based on lodged algorithms. The control device 703 can, for example, also receive the control command from the input receiving unit 710.

Moreover, the operating lever 705 can be automatically returned to the neutral position 717 after an actuation. Damping the resetting motion is presently controlled by the brake device 702.

The invention provides an input device 700 and in particular an advantageous joystick 711, in which the detent positions are not fixedly specified mechanically, and/or wherein the behavior of the joystick 711 during movement is not fixedly specified mechanically, which moreover can be provided with a force feedback, which in particular requires little mounting space, and is moreover inexpensive in manufacture. The low power consumption and the low weight are moreover advantageous, depending on the location of use.

In order to achieve this goal, a shear damper or wedge damper, acting as a controllable brake device 702, can by means of magnetorheological liquid, damp the movement of the joystick 711, respectively generate the torques required therefor, respectively forces on the lever 705, in the pivot point.

A linear (pivoting) motion X-Y (of the joystick) is in particular first converted to a rotational motion and then damped. A transmission may be installed so as to provide sufficiently strong resistance (force on the lever member or torque in the joystick pivot point). The gear ratio may be 2:1 or 3:1 or 4:1 or more. In a concrete variant it is approximately 3:1. High gear ratios show the drawback of (inter) play and require more mounting space. However, they allow to correspondingly increase the braking momentum of a shear damper. In a concrete configuration it is lower than or approximately equals 4 Nm, so that a transmission of 3:1 can provide a controllable braking momentum in the joystick of 12 Nm. Transmission may be performed via a gear transmission including suitable gear wheels, e.g. spur gear-, worm gear drive, or having a toothed belt, V-belt, chain, harmonic drive gear.

The principle of the shear damper is described in our earlier document WO 2016/156544 A1 to the applicant, and it may be used with a joystick. The disclosure of WO 2016/156544 A1 is incorporated herein by reference, pages 1 to 41, including pertaining Figures on pages 1/6 through 6/6, and the disclosure content of the claims 1 through 26 is included in this application by reference. In the concrete case, a shear damper with magnetorheological liquid and a braking momentum of 4 Nm shows the dimensions of 32 mm (diameter)×80 mm length, i.e. a structural volume of ca. 65 000 $mm^3$. In contrast to this, an electric motor having a torque of ca. 4 Nm (stepper motor, servo motor) shows the approximate dimensions of 100×100×200 mm, thus a structural volume of ca. 2 500 000 $mm^3$. This is approximately 38 times the structural volume of the shear damper.

Alternately, the magnetorheological wedge principle may be used for a brake device (brake/damper), as it is described in our WO 2012/034697 A1. The disclosure of WO 2012/034697 A1, pages 1 to 59, including pertaining Figures on pages 1/10 through 10/10, is incorporated herein by reference, and the disclosure content of the claims 1 through 22 is included in this application by reference. The magnetorheological wedged damper is structured still smaller than the magnetorheological shear damper, its dimensions are ca. 40 mm (diameter)×20 mm, thus having a structural volume of ca. 26 000 $mm^3$, which is almost 100× less than in the electric motor.

This results in a considerable improvement to the mounting space in the use of a brake device on the basis of a shear damper or a magnetorheological wedge damper. The component weight is approximately directly proportional to the structural volume, thus it is also considerably less in the invention. The mounting space and the weight are a decisive criterion in many applications.

Hydraulic or pneumatic systems require less space than do electric motors, but lines and auxiliary systems are required instead (pressure accumulator, pumps . . . ). Moreover, the controllability and noise emission are very disadvantageous. None of the two can be employed for computer games respectively in the field of gaming, respectively they do not find the users' acceptance.

Electric motors also show the drawback that, based on their concept, they heat up very much and overheat, if high torques (holding torques) are required in standstill over extended periods (the coil windings heat up, whereby the resistance in the coil wire increases, whereby the heat-up increases still further, etc.). The power requirement and heat-up then increase overproportionately. Magnetorheological brake devices do not show this drawback.

The behavior of the joystick during movement, i.e. the operating force respectively feedback generated thereby (most often by/to the active hand) can be variably controlled with the invention, dependent on the situation. This is achieved in that in controlling the electronics, controlling the magnetic field in the magnetorheological brake device (e.g. in the shear damper), and thus the strength of damping, is regulated respectively varied quickly. The control preferably responds fast to what is the presently applied operating mode respectively use case, and as a result thereof, to the speed and/or speed changes and/or directional changes of the joystick. Use cases are application cases dependent on the situation. An application case bundles a number of scenarios or even all the conceivable scenarios which may occur when a user attempts to achieve a specific goal by means of the system described. A use case may also be referred to as an application situation.

A barrier (increased torque, e.g. up to the maximum value) in one rotational direction is not meant to block in the other rotational direction as well (freewheeling function). If one moves the joystick in the direction to the barrier, the torque should be cancelled immediately, as force ceases to be applied in the direction of the barrier. Otherwise the user feels the joystick adhere to the barrier. The lever virtually remains "stuck", which deteriorates the response (the user's desire) of the vehicle caused thereby. Then, when one moves the joystick back in the direction to the barrier, the torque should be immediately increased, so that the user immediately perceives the barrier again.

A structure including a shear damper allows to convert the linear or pivoting motion of the joystick to a rotational motion of a wheel.

A transmission stage 708 allows to bring the movement to a higher rotation speed, so that the shear damper can transmit higher torque to the joystick. A concretely configured shear damper cannot apply more than 4 Nm braking momentum in the available mounting space. Due to the transmission (e.g. ratio 3:1) the momentum achieved at the joystick may be three times larger. The transmission may consist of gear wheels only, or may be equipped with toothed belt(s), chain(s), friction wheel(s) and the like. Gear wheels show the drawback that their geometry is predetermined by the size of the gear wheels. In contrast to this, using a toothed belt offers more flexibility in the construction and less noise. Use of cross-located gear wheels is also possible, whereby they are without play.

The magnetorheological brake device 702 respectively the shear damper or the MRF brake member may be larger in structure, whereby higher damping-/braking momenta can be generated. In most of the cases, however, a combination of a smaller damping/braking unit with a transmission is a better solution in view of the mounting space, weight, and costs.

Instead of the shear damper, basically any MRF brake device may be used (wedge bearing, swinging vane, etc.). In addition to the advantages indicated above, the gear for transmission is advantageous for saving space, since the brake does not need to be directly flange-mounted, and can thus be positioned as desired.

The fast-response MRF brake (in the range of milliseconds) allows to generate a multitude of haptic feedbacks. The advantages of MRF brakes, such as fast response and an arbitrarily adjustable force/torque in operation, are utilized.

Figure 15:
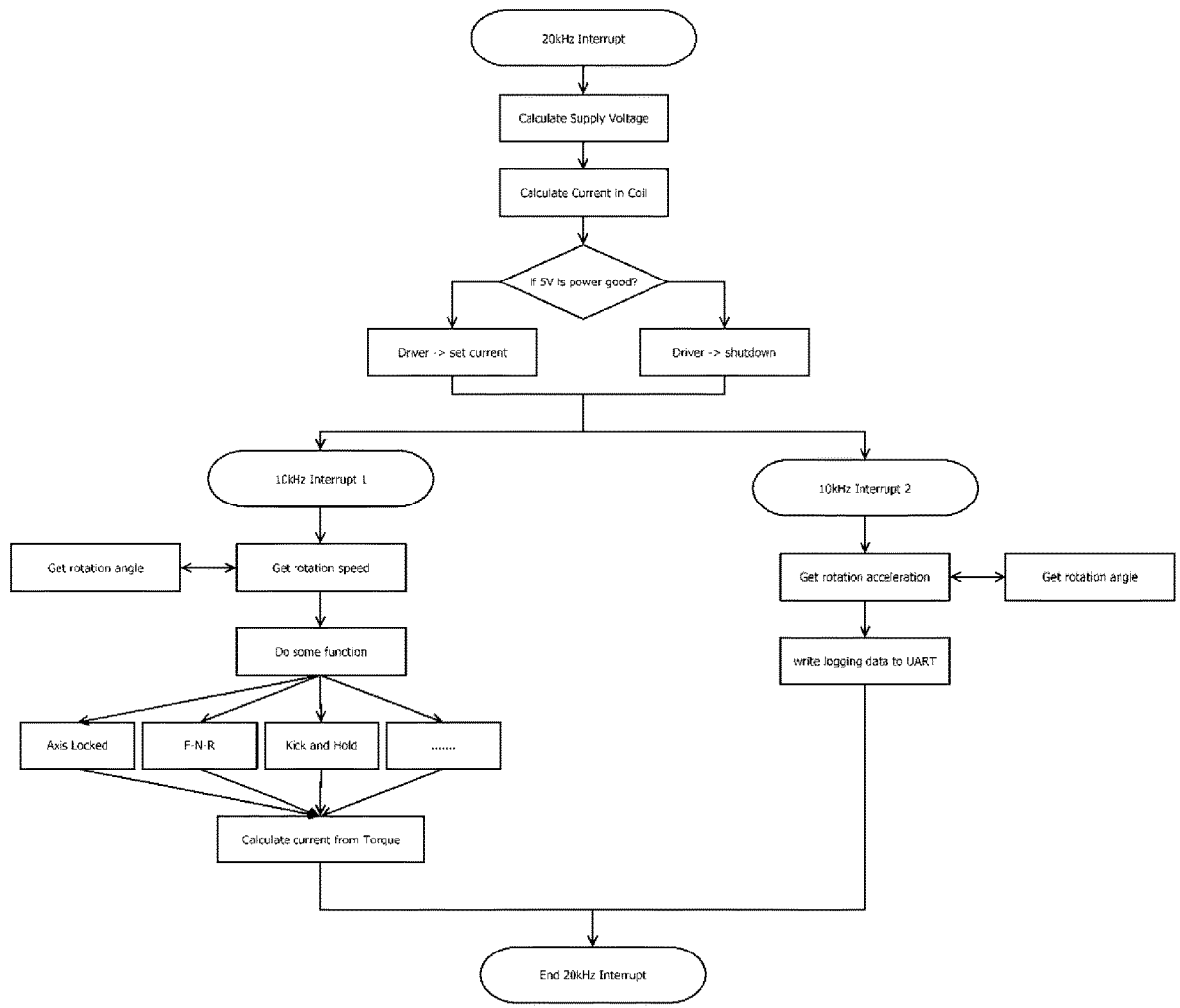
FIG. 15 a sketch on signal processing in the input device according to the invention.

An exemplary signal processing is generally illustrated in the diagram of the FIG. 15.

Exemplary actuations or use cases of the invention will be described below. The FIGS. 3 through 13 show progressions of the deceleration torque over the rotation angle respectively the time.

Spring-biased and non-adaptive joysticks swing/oscillate around the central position (neutral position), when they are released out of their extreme positions and allowed to move freely. This may result in undesirable movements of the mechanism connected with the joystick (e.g. snow shovel of a snow groomer; container load on a harbor crane).

The invention prevents such swinging back in a standard mode. No barriers or ripples are generated. The maximum speed of the joystick motions is controlled (V regulation). The maximum speed is dependent on the position (i.e. the angle) of the joystick. The closer it approaches the zero position (central position), the stronger is the movement braked, and the slower is the possible movement. This prevents the joystick from overshooting around the neutral position. If the joystick is simply let go while it is pushed forward, the resetting spring pulls it back to the neutral position and brakes it precisely toward 0°. Absent active braking it would, particularly if it is first let go from the end travel positions, swing past the central position and then swing back, swinging out over time. The users tend to not desire this, and it is disadvantageous in terms of operation. The swinging (out) movements of joysticks not controlled according to this invention may result in disadvantageous peak loads to the tool/load.

Figure 3:
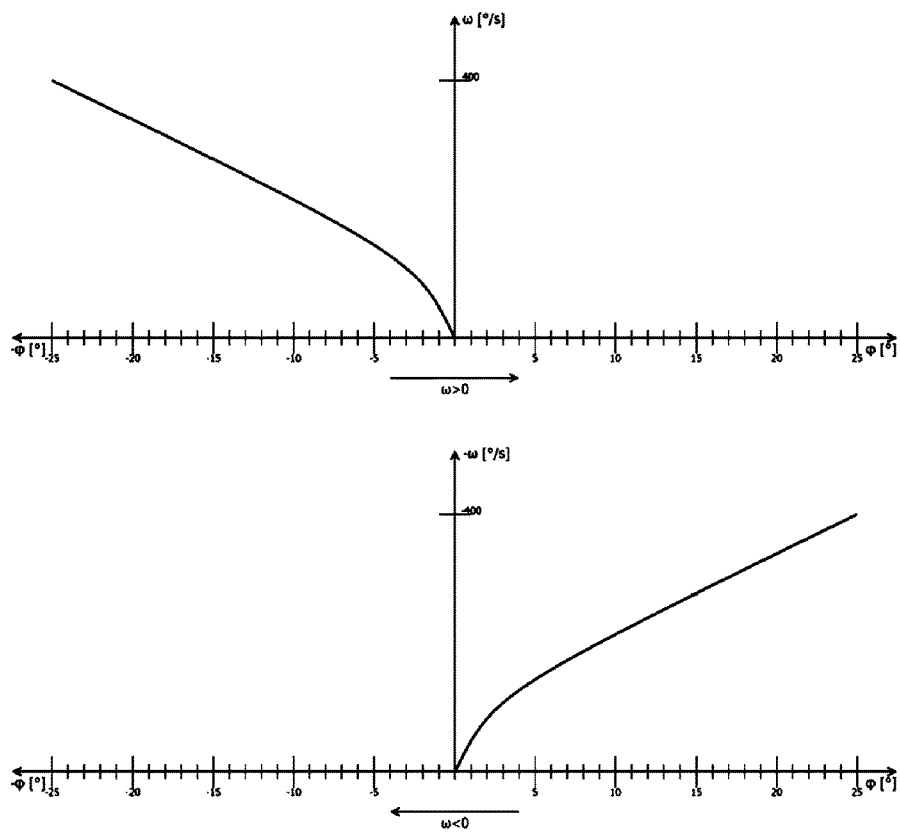
FIGS. 3-13 purely schematic sketches of progressions of deceleration torques.

FIG. 3 shows the maximum angular velocity of the shear damper in the joystick, dependent on the angular position of the joystick.

In the operating mode "unidirectional", movement is possible in one direction only.

The motion axis of the joystick is locked from the 0° position in one direction, the shear damper generates a torque barrier in this direction. Movement is only possible in the other direction.

Figure 4:
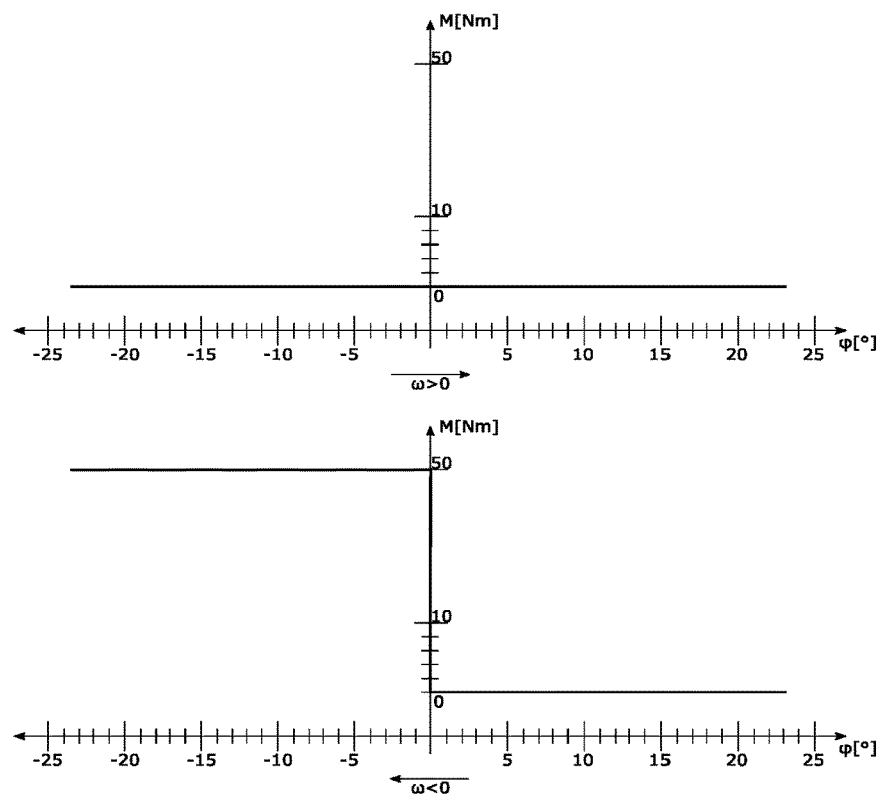

In FIG. 4 the barrier acts (only) in one direction. A torque barrier is generated in one rotational direction. The joystick can only be pushed in the opposite direction.

In the operating mode "smart stop" the joystick can stop in any position. The torque of the magnetorheological brake device, and presently of the shear damper, is adapted to the spring characteristic curve of the resetting spring, i.e. the damper provides the same braking force as the resetting spring applies in the other direction. When a user pushes the joystick to a position and releases it, the joystick remains exactly in this position.

Figure 5:
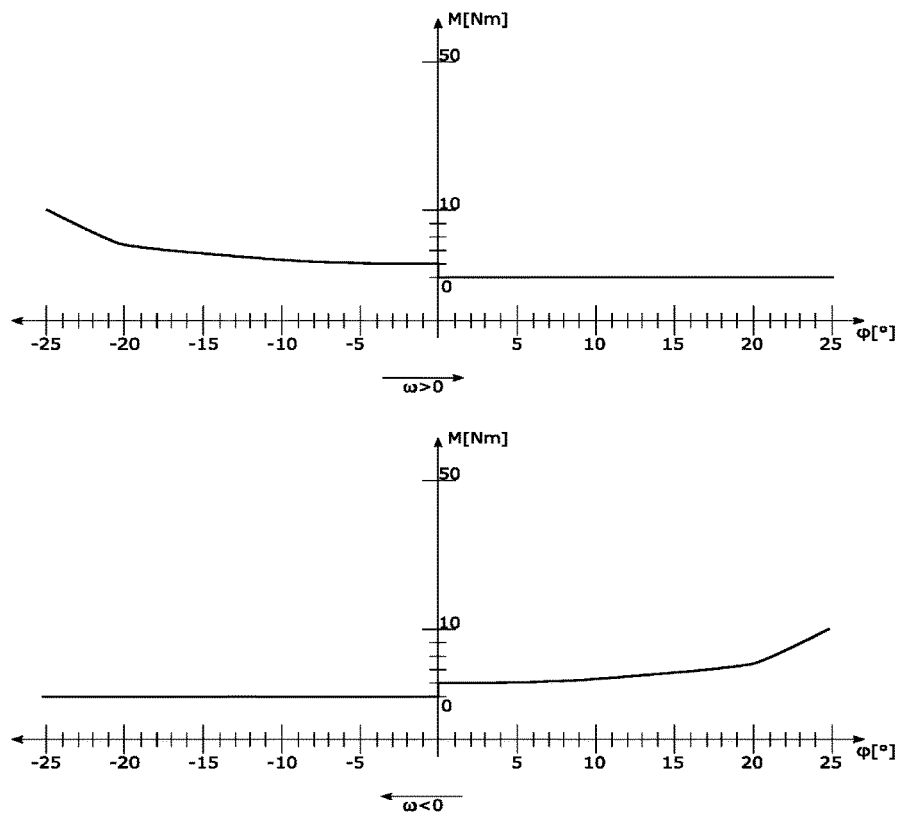

FIG. 5 shows the progression of the torque, depending on the characteristic curve of the resetting spring. The torque is still high enough so that as the joystick is released, it remains in place.

In the operating mode "ripple" the torque on the operating lever and thus the force on the man-machine interface (e.g. hand) is alternated/shifted between low and high values. The user thus feels a pattern of alternating movement and braking. The distances and lengths of each of the torque positions may be controlled, either based on the time, or dependent on the angle, or as combinations thereof. In an angle-controlled ripple, the barriers are started in certain angular positions and retained up to a defined angle (angle-triggered).

Figure 6:
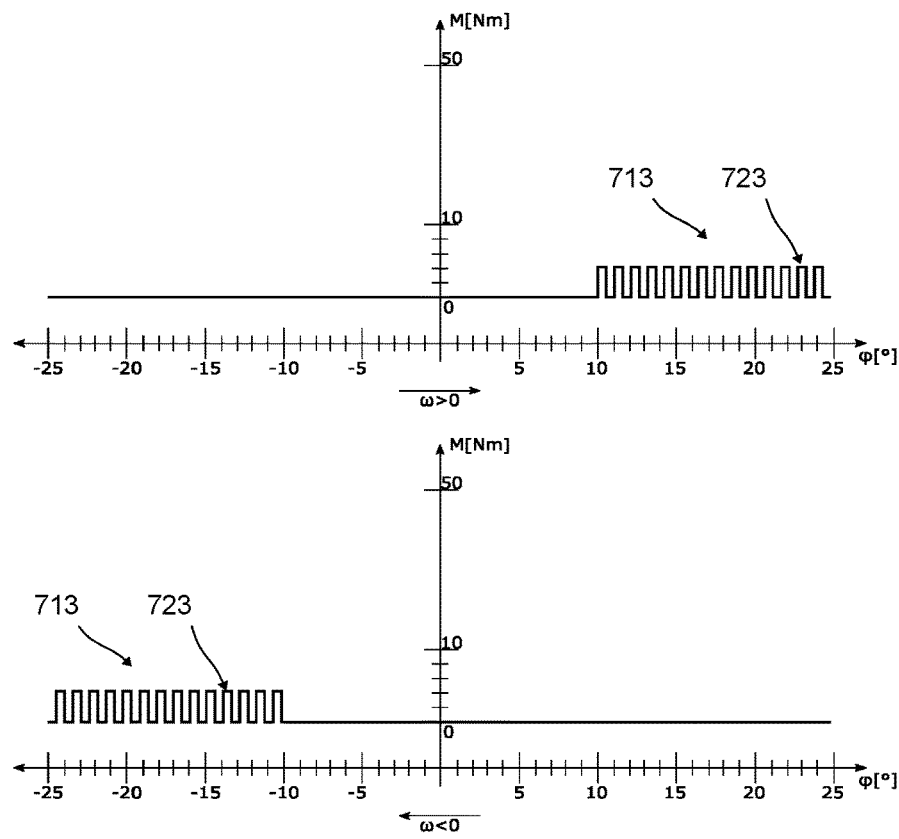

FIG. 6 shows this mode. The ripple begins at 10° and changes the resistance in 1° increments. In this case the ripple is generated in one direction only (no more while returning to the 0 position).

FIG. 6 shows a ripple triggered and controlled by way of the angle. The braking momentum (Y-axis) is alternatingly applied between a high and a low (e.g. basic torque) torque, respectively the force (Y-axis) at the lever is varied between the operating hand and the joystick.

Figure 7:
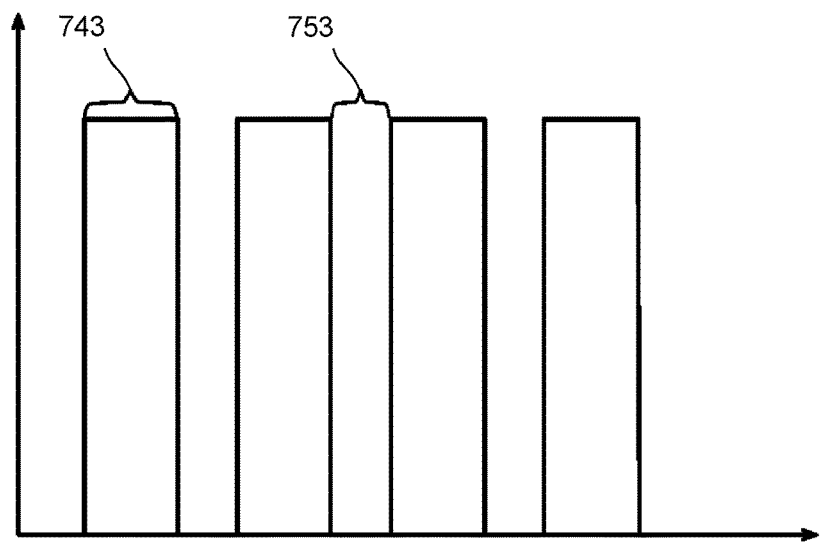

In the time-controlled and time-triggered mode the length 743 of the barriers and also the distance 753 between the barriers is specified regarding the time (FIG. 7).

FIG. 7 shows the time-triggered and controlled ripple. The X-axis shows the time, the Y-axis the force on the operating lever respectively the torque (deceleration torque) in the pivot point. The distance and the length are time-controlled.

Figure 8:
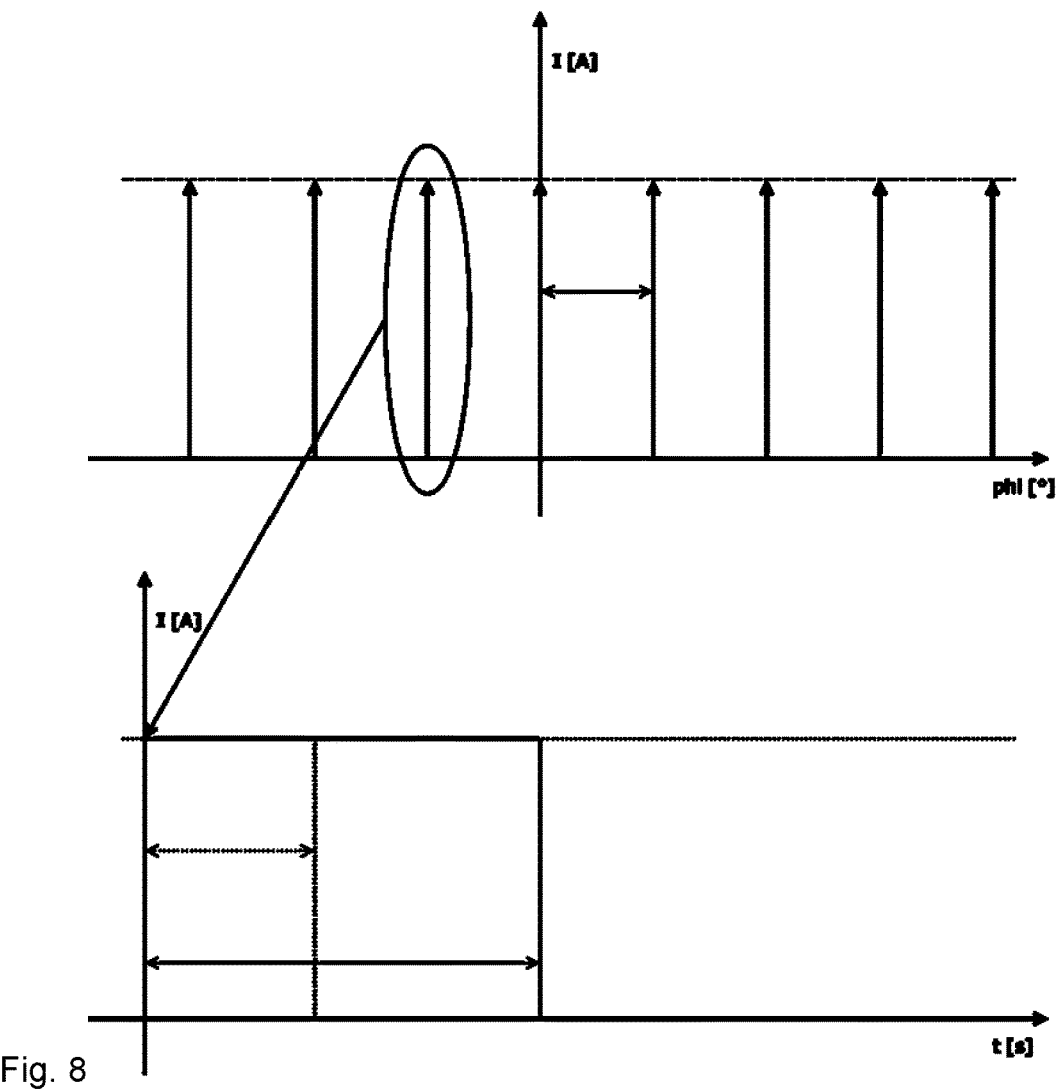

The two modes can be combined by exchanging the triggering. For example, the starting points of the barriers can be determined by the angle, while the length is always given over the same time, as shown in FIG. 8. As the ripples start with a specific angle, the barrier is held over a specific time and then released, no matter what the angle. If an angular position (starting position) is passed over within the duration of one ripple, this ripple point can be omitted or can immediately follow.

This mode allows e.g. to control the motion speed, or a high pass filter for vibrations or fluttering can be realized with a quickly adjustable periodic time. Vibration or fluttering means that the feedback thereby generated provides the feel of vibrations or fluttering to the user's hand.

FIG. 8 shows the time-controlled and angle-triggered ripple. The length is timed, the starting points are defined by the angle.

A ripple mode may certainly be changed by the time or the angular position, e.g. the mode may vary in ripple points after a certain number (turn finer). Thus, the user feels that a certain region has been reached, e.g. approaching the end position, maximum speed etc., in the form of changing ripple lengths (=dynamic adaptation).

The operating mode spring ripple is a modified form of the ripple mode. The ripple barriers are not generated by jumps (low-high; little-much) of the actuator current, and as a result by the magnetic field, but they vary continuously. One can thus feel how the barriers build up and go down. The control signal may be a sine- or cosine signal, at a slight offset from zero. The current varies constantly, without jumps, and briefly turns slightly negative, so that the metal in the damper or the magnetorheological brake device is demagnetized and briefly magnetized again, before the current turns positive again, to thus be again demagnetized and newly magnetized. The user perceives these changes between magnetizing and demagnetizing and the continuous changes to the damping/braking similarly to the braking by means of a detent spring in a slide gate (peak/valley gate).

Figure 9:
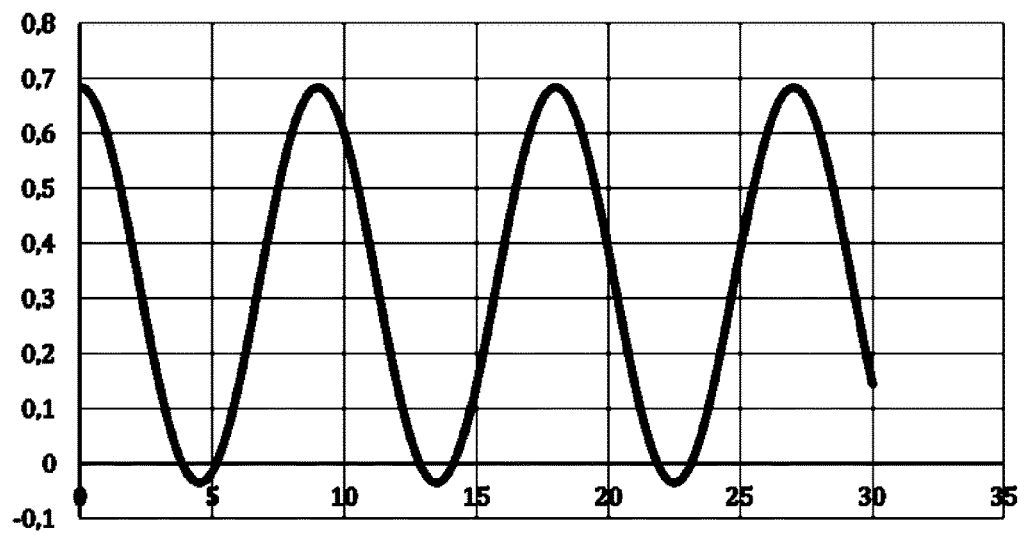

FIG. 9 shows the actuator current in spring-ripple mode. The current changes continuously, having two zero crossings per period.

In addition, the current may be adapted to an, or the, angular velocity. The torque of the damper is dependent on the speed and decreases with higher speeds. In order to obtain the same torque over various speeds, the current must be increased.

Figure 10:
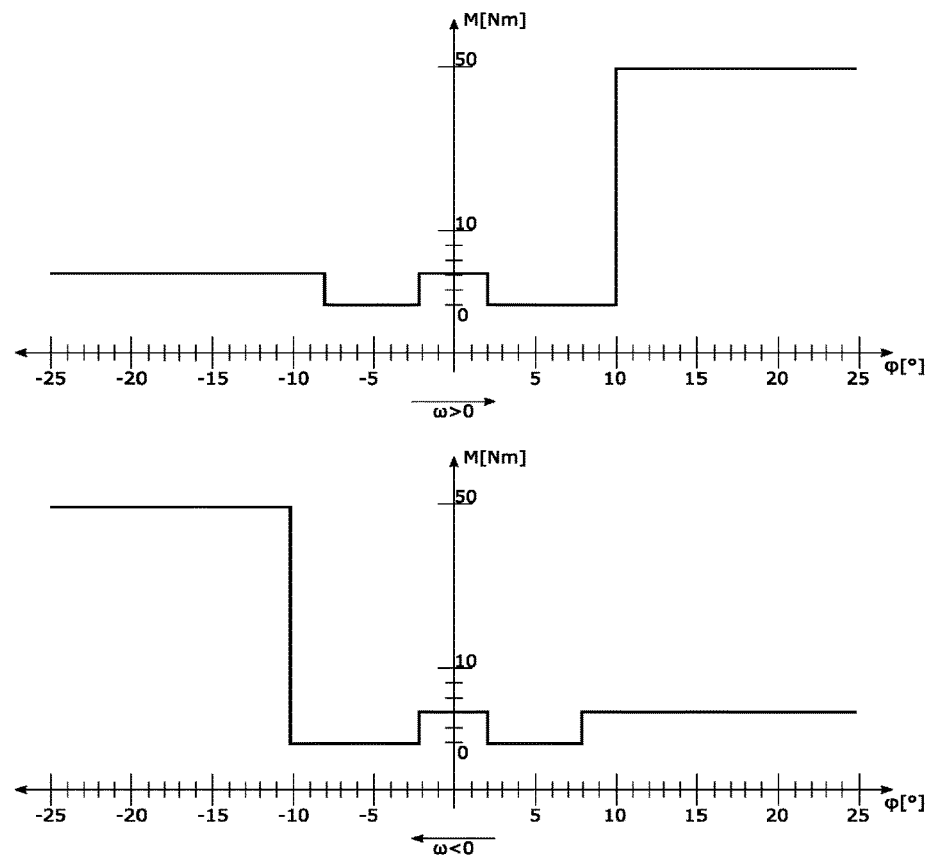

In the operating mode "FNR" (front, neutral, rear) shown in FIG. 10 the joystick can be set between different detent positions (e.g. in an automatic transmission: front, neutral, rear). Between the predetermined detent positions the torque is minimal and as the position is reached, it is raised to a value in which the joystick remains (stays in place), since the spring restoring force is not sufficient for overcoming the braking force. If the user wishes to bring the joystick to another position, the resistance must be overpressed, and it can be moved up to the next position. The detent positions are e.g. at −8°, 0° and 8°. At e.g. −10° and 10°, an end stop in the form of maximum torque is generated.

The advantage of the adaptive MRF technology in this case, over conventional friction/sliding brakes is, that no stick-slip effect (stick effect) will occur. In conventional systems a static friction must first be overcome. Since the dynamic friction is much lower, the brake then slips through, and when it stops once again, it sticks better again; so that jerky movements occur on the joystick and on the operated tools or objects in functional connection with the joystick. Jerky movements may result in high peak loads and overload (increased machine wear). This is not the case with the solution according to the invention, and is a great advantage in use.

In the operating mode "axis locked" a barrier with maximum torque in all the directions is generated (from the zero position). The joystick is thus locked in its movements.

When the joystick is in the zero position, it cannot be moved. If it is deflected at the start, it can be returned to the 0 position and is then locked. If the joystick is deflected in a positive position and is accelerated in a positive direction (as in a negative position with negative acceleration), the joystick will be locked. Otherwise it can move freely, so that it can be returned to the 0 position (base position).

Figure 11:
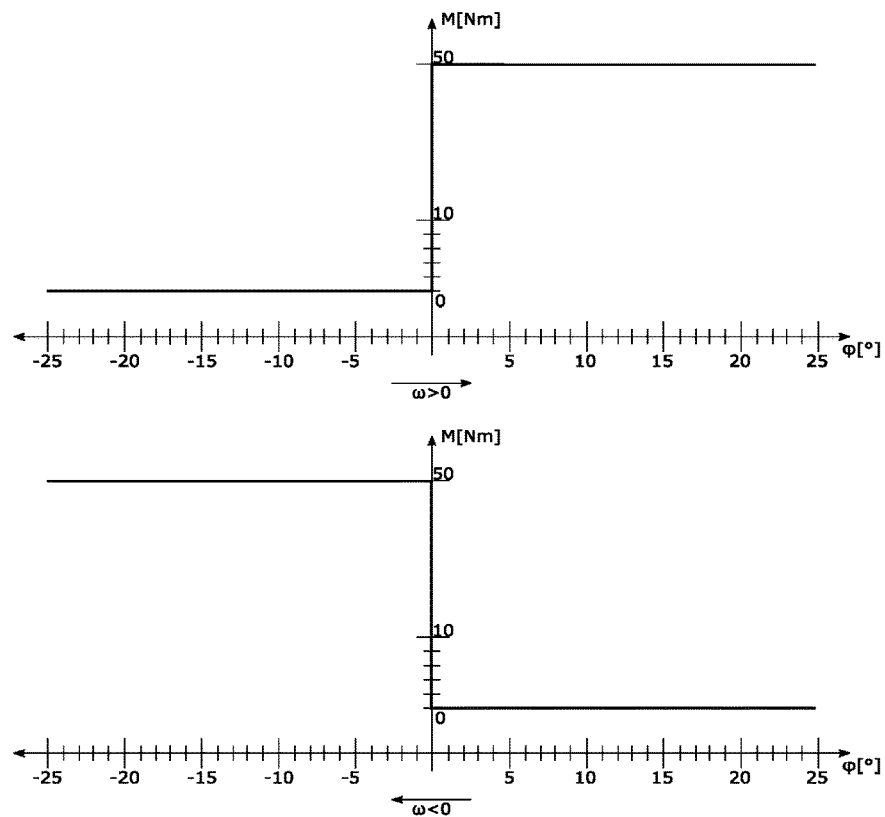

FIG. 11 shows the locking of the movement in both directions.

In the operating mode "kick and hold" the resistance is increased over a short angular range, given a specific angle. The resistance is also preserved as the joystick moves in reverse due to the resetting spring or the user's hand, and it is thus active in both movement directions. Alternately it may be active in one movement direction only. Then the joystick is held in the position. In the figure the torque spike begins at 15° and ends at 18°. This means, if the joystick is pushed beyond this range (here, more than 18°) and let go, it returns to 18° spring-loaded, and then stays at 18°. If is is positioned at less than 18°, it returns spring-loaded to the zero position.

Figure 12:
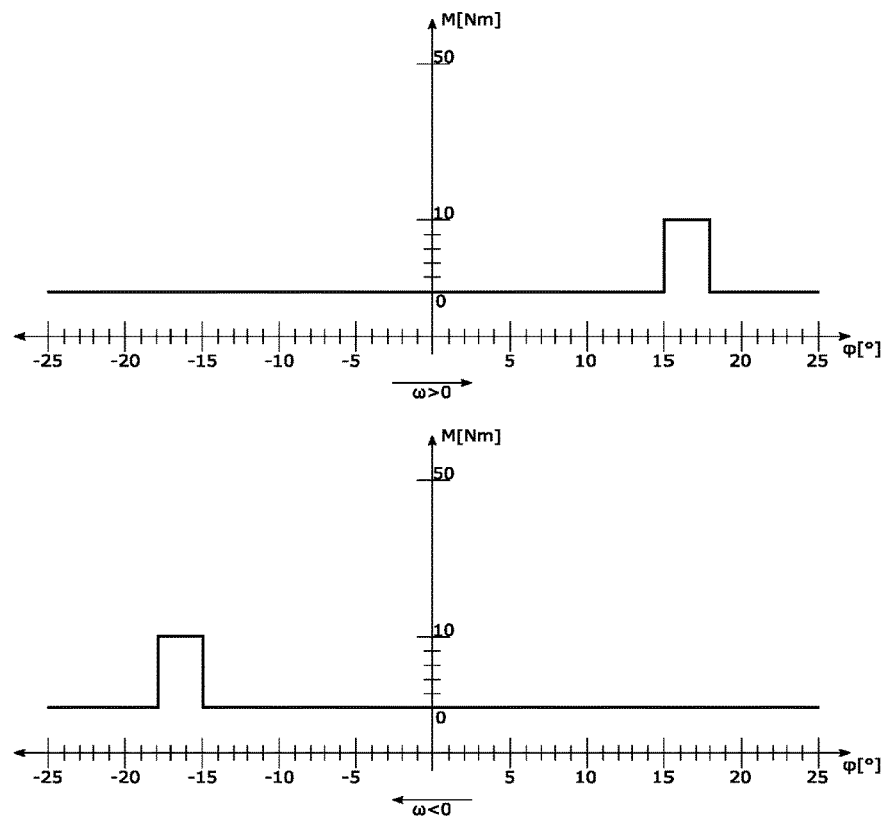

FIG. 12 shows "kick&hold" in the forward direction. The torque spike is provided in both pivoting directions (i.e. forward and back from the neutral position).

Figure 13:
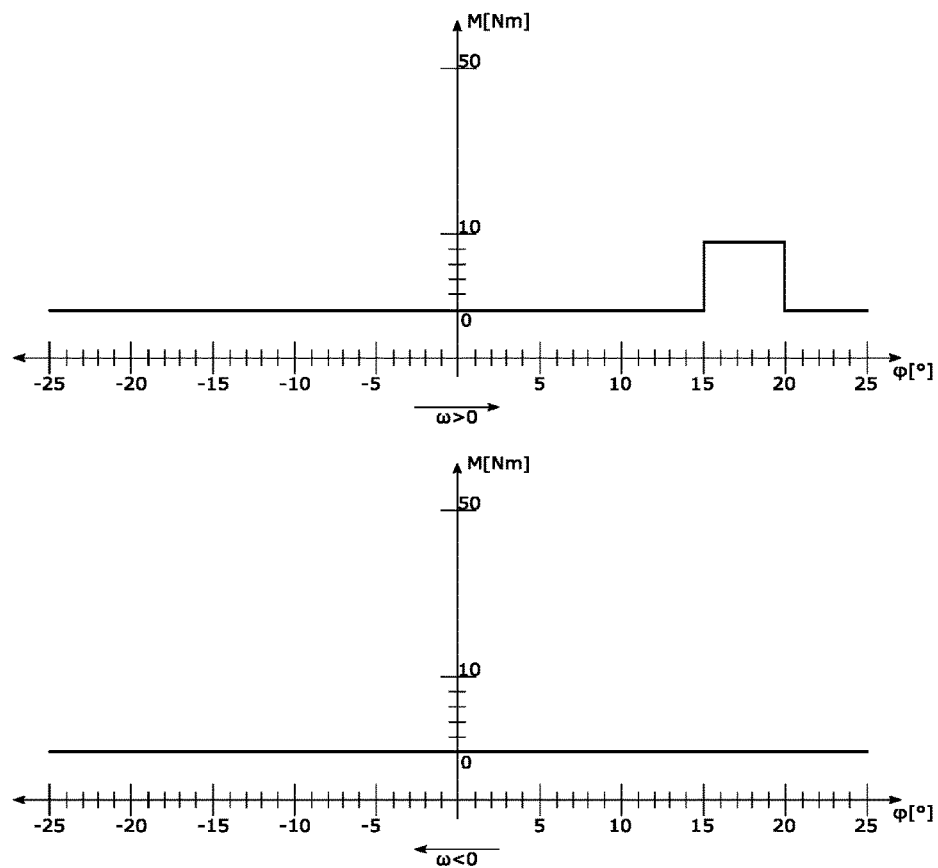

In the operating mode "kick down", a brief resistance is generated in one direction, the return movement goes up to the 0 position. In the example of FIG. 13, the torque spike must be overpressed in the range 15-20° and it can then move back, without braking. As the FIG. 13 shows, a brief resistance is generated in one direction, the return movement takes place without resistance.

Figure 14:
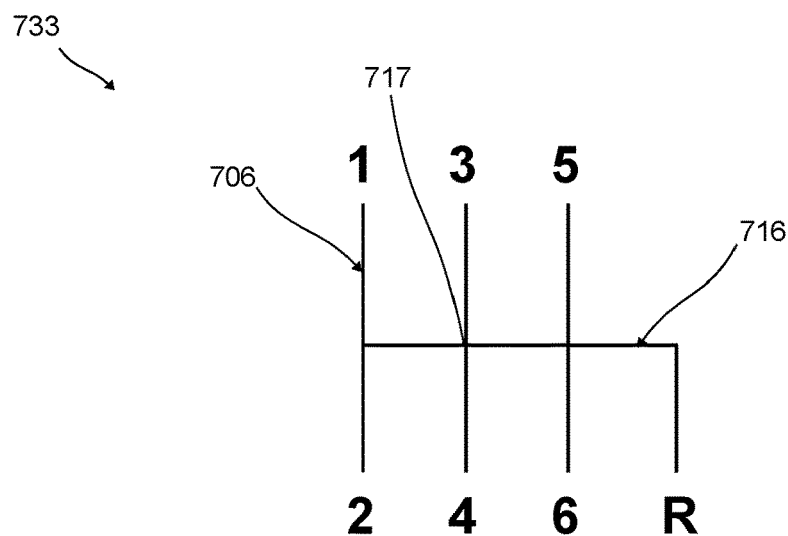
FIG. 14 a purely schematic illustration of a slide gate mechanism simulated with the input device according to the invention.

In the operating mode freely selectable "slide gate", the adaptive joystick according to this invention copies e.g. the classical slide gate of a mechanical gear shift (e.g. H-shifter/slide gate). Such a slide gate mechanism 733 is shown in the FIG. 14.

According to this invention the MRF dampers/brakes are alternatingly actuated so that the joystick can only be moved e.g. in an H-pattern. When the operator/user wishes to move e.g. the joystick, or in this case the shift lever e.g. of a motor vehicle (car), diagonally from the shifting position 2 to the shifting position 3, this is prohibited by energizing the X-axis- and Y-axis MRF dampers (magnetorheological brake device). Firstly only movement of the Y-axis damper is permissible, the X-axis damper is locked. From the Y displacement center onward, only movement of the X-axis damper is permissible, the Y-axis damper is locked. Then, after a certain X distance, only movement of the Y-axis damper is enabled, until the position 3 is reached. The user thus feels as if he shifted the gears manually in a slide gate, as he is used to do in his car with a manual transmission. In fact, however, shifting takes place automatically through the electronics (Shift By Wire) and by simulating a slide gate by intelligent activating of the X- and Y-MRF axes.

What is important is that this be done quickly and harmoniously. In this way, different numbers of gear speeds, automatic shift levers on one, two or three levels, sequential shift patterns and various designs can be generated virtually. Various actuating forces, movement paths, and also classic car shift systems can be simulated. Thus, the user's (customer's) preferred shifting method can always be applied/preset for example in a rental vehicle or leased vehicle, which enhances the operating comfort and reduces operating errors.

In the operating mode "increasing resistance" the resistance increases in particular linearly or polynomially, thus indicating to the user by way of the resistance in which region he is located. The resistance for example increases with faster operation of a machine, or faster movement of the load, thus preventing accidents due to high speeds.

A combination of the modes is also possible. Thus, any desired modes can be combined. For example, one can combine a "ripple" and the "smart stop", so that movement of the joystick generates a ripple, and release makes it remain in place. The sensor technology also allows fast changes between modes when the direction is changed.

Expansion from one motion axis to two motion axes or three motion axes is also possible.

The following statements on the various operating modes will be explained for one motion axis each (forward and back; x-axis). However, they may be extended in analogy to a second or a third axis (left, right; y-axis, z-axis).

For use in gaming, certain requirements are set to the gaming joystick, such as a good stand even with fast movements (stable material, sufficient weight). The joystick should be ergonomic in design, be a good reproduction of real shift joysticks, and optionally show sufficient numbers of keys for special key assignments.

The resistance of the joystick differs depending on the gaming situation. Thus, it may be adapted to real systems (e.g. the flight simulator game joystick of a Boeing 747 behaves differently from that of a Cessna), and/or additional response/feedback of the system by vibrations is possible.

The resistance in the zero point is a significant criterion in particular for gamers (flight simulators): Real cockpit joysticks show very low resistance around the zero point, and good joysticks should imitate the real cockpit joysticks as perfectly as possible. An MRF brake device with a very low base momentum can keep the resistance around the zero point very low.

Vibration may be simulated "passively" by MRF brake, by generating a ripple at very short intervals, whereby the user feels vibration during movement.

Adaptivity is a particular advantage of the invention. One series component may be developed, which can be customized as desired. The production of small batches can be accelerated, and production costs can be saved.

At the same time a number of dummy knobs may be provided, which can be assigned individually. Customer-specific personalization is possible. Layouts for right-handed and left-handed users are possible. Personalized and/or intelligent feedback may be provided. The construction can be flexibly adapted. A small number of parts results in low cost.

The force of the spring or resetting spring can be neutralized. The force of the resetting spring used may in particular be "set" by damping the restoring force. Thus, the same spring strength may be used for different joysticks where different restoring forces are desired (in this case, movement counter to the spring would have to be actively supported). The adaptability also goes for different temperatures, contamination, aging, and wear. Independently of these changing parameters, the user will receive the same (familiar) haptic feedback and behavior.

It is also possible to set the action point and the forces. The adjusting force (action point) etc. can be adapted in relation to the customer or the customer's wishes. This is also dependent on the external state, i.e. on a smooth ground in a vehicle: lower momenta/forces. This reduces the operating force and user's fatigue. On rough roads or in uneven terrain: Higher forces/torques. This reduces wrong shifting respectively permits more precision of movement.

Another considerable advantage is the absence of stick-slip effect. Braking/damping is not performed by way of classical, friction-based brakes. The MRF dampers damp, depending on the electric current/magnetic field. When the magnetic field is switched off, the braking action is immediately cancelled, no matter the speed of movement. The braking force is not, or only slightly, speed-dependent, thus no jerky movements as in stick-slip effects can occur.

Multiple axes mode is also possible (multiaxes- and singleaxes mode). Each single rotary motion around a separate axis can be separately controlled via separate magnetorheological brake devices. Optionally, one single magnetorheological brake device is sufficient for braking rotary motions around different axes.

The same series component may serve to generate either joysticks showing one movement direction only (e.g. forward) or up to 4 directions (forward, back, left, right).

A haptic performance indication is possible. The performance provided by a machine/vehicle may be indicated e.g. by increased resistance.

A haptic feedback can considerably increase safety in operating machines, since the user does not need to shift his eyes to displays to identify problems.

Medical applications can also be advantageously implemented by way of the invention. Thus, robots can be controlled in an operation, e.g. to prevent incorrect cuts with a scalpel, or to play back different cutting forces. Laboratory apparatus in a laboratory can be controlled. Thus, for example sample holders can be automatically shifted under a microscope to prevent collisions.

Inadvertent actuation can be prohibited. Adaptation to external circumstances is possible. Inadvertent actuating can be prevented e.g. by generating a short ripple following extended non-use, as a standard procedure. Thus a user immediately feels it if he moves the joystick unintentionally. An external impact (e.g. going through a pothole) may also result in unwanted shifting. This can be prevented by increasing the force/torque, if such an event occurs which the entire system detects and analyzes, and forwards to the joystick control. For example: When a vehicle acceleration sensor senses amplified build-up movements, then the joystick actuating force/momentum is automatically adapted, so as to reduce maloperations.

The joystick may detect via Bluetooth, WLAN, ZigBee, NFC, Wi-Fi, LiFi, 3G, smart phone, smart watch, chip, key, etc. which user intends to use the joystick, and can thus adapt itself to that user's requirements/preferences, either preconfigured or automatically. The joystick respectively the pertaining control electronics may be provided for learning (Fuzzy Logic. Artificial Intelligence. Machine Learning), and thus continuously optimize the operating comfort and reduce operating errors.

Near field recognition systems (radar, ultrasound, camera-based, lidar . . . ) provide significant information to the control electronics of the joystick, thus influencing the haptic feedback.

A number of systems are networked, and external signals may be supplied (e.g. via Bluetooth, WLAN, ZigBee, NFC, Wi-Fi, LiFi, 3G, 5G . . . ), all the data is analyzed and results in corresponding real time feedback in the joystick. This allows more ease and safety of handling complex situations with the joystick, due to situation dependent feedback.

The angle sensor is preferably provided for more than 30,000 increments per rotation, and the regulation frequency of the control, more than 5 kHz.

The entire system may show a redundant structure, as the purpose requires (e.g. double motion trackers and rotary dampers . . . ).

If the control electronics detects imminent failure of a relevant sensor or damper early, this may be clearly signaled to the user in form of a haptic feedback (e.g. persistent, strong vibrations). This also applies if for example the sensor of the Y-axis fails and the user must, or wants to, actuate the X-axis. The adaptive joystick may adapt to these special or emergency situations and support the user optimally with the remaining operating options (with feedback).

The presently introduced input device 700 is equipped with brake devices 702 on the pivot axes 706, 716 provided, which brake devices are configured as, or at least comprise, a magnetorheological transmission device 1 each. Thus the configurations and functions described above of the input device 700 can be implemented particularly advantageously.

With reference to the FIGS. 16 through 38, exemplary embodiments of the magnetorheological transmission device 1 are explained hereafter, wherein identical or similar parts are provided with the same reference signs.

Figure 16:
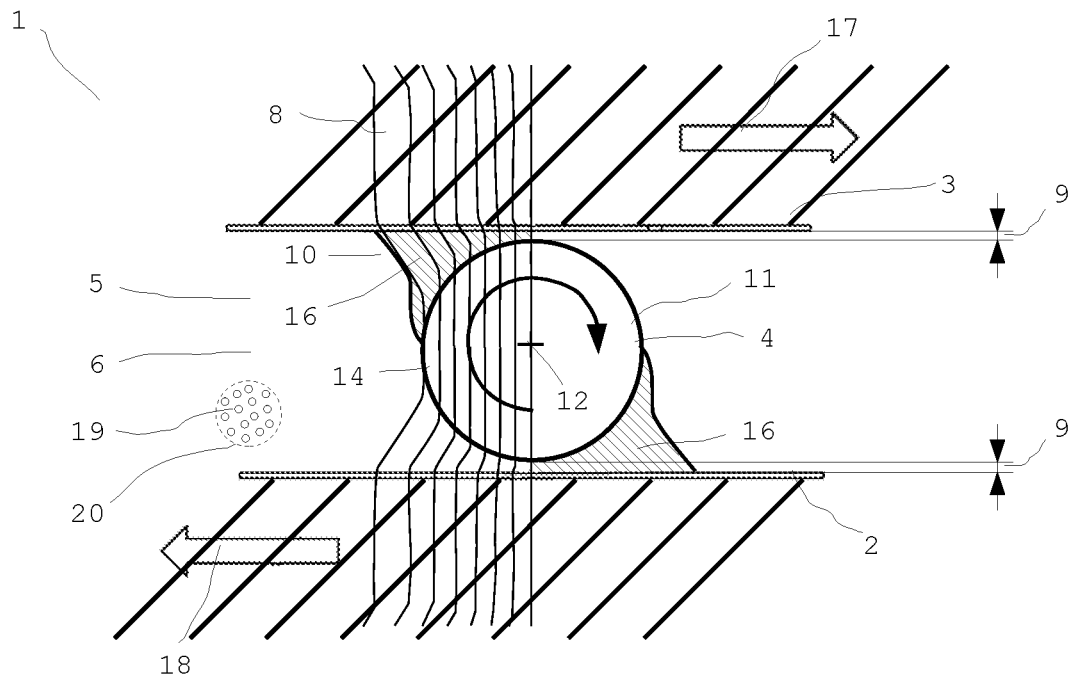
FIG. 16 a very schematic view of a magnetorheological transmission device in cross section.

FIG. 16 shows a very schematic cross-sectional view of a magnetorheological transmission device 1 for influencing the force transmission between two components 2 and 3. A rotating body 16 is provided as a separate part 4 between the two components 2 and 3 in FIG. 16. The rotating body 11 is embodied here as a ball 14. However, it is also possible to embody rotating bodies 11 as cylinders or ellipsoids, rollers, or other rotatable rotating bodies. Rotating bodies, which are not actually rotationally symmetrical, for example, a gear wheel 34 or rotating bodies 11 having a specific surface structure can also be used as rotating bodies. The rotating bodies 11 are not used for the mounting in relation to one another, but rather for transmitting torque.

A channel 5, which is filled here with a medium 6, is provided between the components 2 and 3 of the magnetorheological transmission device 1. The medium is a magnetorheological fluid 20 here, which comprises an oil as the carrier liquid, for example, in which ferromagnetic particles 19 are present. Glycol, grease, and viscous materials can also be used as the carrier medium, without being restricted thereto. The carrier medium can also be gaseous or the carrier medium can be omitted (vacuum). In this case, only particles which can be influenced by the magnetic field are poured into the channel.

The ferromagnetic particles 19 are preferably carbonyl iron powder, wherein the size distribution of the particles depends on the specific usage. A distribution of particle size between 1 and 10 μm is concretely preferable, wherein larger particles of 20, 30, 40, and 50 μm are also possible. Depending on the application, the particle size can also become significantly larger and even advance into the millimeter range (particle beads). The particles can also have a special coating/sheath (titanium coating, ceramic sheath, carbon sheath, etc.), so that they can better withstand the high pressure loads occurring depending on the application. The MR particles can be produced not only from carbonyl iron powder (pure iron), but rather also from special iron (harder steel), for example, for this application.

The rotating body 11 is set into rotation around its rotational axis 12 by the relative movement 17 of the two components 2 and 3 and practically runs on the surface of the component 3. The rotating body 11 simultaneously runs on the surface of the other component 2, so that a relative velocity 18 is present there.

Strictly speaking, the rotating body 11 has no direct contact with the surface of the component 2 and/or 3 and therefore does not roll directly thereon. The free distance 9 from the rotating body 11 to one of the surfaces of the component 2 or 3 is, for example, 140 μm. In a specific design with particle sizes between 1 μm and 10 μm, the free distance is in particular between 75 μm and 300 μm and particularly preferably between 100 μm and 200 μm.

The free distance is in particular at least 10 times the diameter of a typical mean particle diameter. The free distance is preferably at least 10 times the size of a largest typical particle. Due to the lack of direct contact, a very low base friction/force/torque results during the relative movement of the components 2 and 3 in relation to one another.

If a magnetic field is applied to the magnetorheological transmission device 1, the field lines form depending on the distance between the rotating bodies 11 and the components 2, 3. The rotating body consists of a ferromagnetic material made of ST 37 here, for example. The steel type ST 37 has a magnetic permeability pr of approximately 2000. The field lines pass through the rotating body and concentrate in the rotating body. A high flux density in the channel 5 prevails on the rotating body at the radial entry and exit surfaces of the field lines here. The inhomogeneous and strong field there results in local and strong crosslinking of the magnetically polarizable particles 19. The effect is strongly increased by the rotational movement of the rotating body 11 in the direction toward the forming wedge in the magnetorheological fluid and the possible brake or clutch torque is greatly increased, far beyond the amount which can normally be generated in the magnetorheological fluid. Rotating body 11 and component 2, 3 preferably consist at least partially of ferromagnetic material, because of which the magnetic flux density is higher the smaller the distance between rotating body 11 and component 2, 3. A substantially wedge-shaped region 16 thus forms in the medium, in which the gradient of the magnetic field increases strongly toward the acute angle at the contact point/the region of the smallest distance.

In spite of the distance between rotating body 11 and component 2, 3, the rotating body 11 can be set into a rotational movement by the relative velocity of the surfaces in relation to one another. The rotational movement is possible without and also with an active magnetic field 8.

If the magnetorheological transmission device 1 is subjected to a magnetic field 8 of a magnetic field generating unit 7 (not shown here in FIG. 1), the individual particles 19 of the magnetorheological fluid 20 chain together along the field lines of the magnetic field 8. It is to be noted that the vectors shown in FIG. 1 only show the region of the field lines which is relevant for the influence of the MRF 20 in a roughly schematic form. The field lines enter into the channel 5 substantially normally to the surfaces of the ferromagnetic parts and above all do not have to run linearly in the acute-angled region 10.

At the same time, some material is also set into rotation by the magnetorheological fluid 20 on the periphery of the rotating body 11, so that an acute-angled region 10 forms between the component 3 and the rotating body 11. On the other side, an identical acute-angled region 10 arises between the rotating body 11 and the component 2. The acute-angled regions 10 can have a wedge shape 16 in the case of cylindrical rotating bodies 11, for example. Because of the wedge shape 16, the further rotation of the rotating body 11 is obstructed, so that the effect of the magnetic field on the magnetorheological fluid is amplified, since a stronger cohesion of the medium 6 in the region results due to the active magnetic field within the acute-angled region 10. The effect of the magnetorheological fluid in the accumulated cluster is thus amplified (the chain formation in the fluid and therefore the cohesion or the viscosity), which makes the further rotation or movement of the rotating body 11 more difficult.

Substantially larger forces or torques can be transmitted by the wedge shape 16 than would be possible using a comparable construction which only utilizes the shear movement without wedge effect.

The forces which are transmittable directly by the applied magnetic field only represent a small part of the forces transmittable by the device. The wedge formation and therefore the mechanical force amplification may be controlled by the magnetic field. The mechanical amplification of the magnetorheological effect can go so far that a force transmission is possible even after an applied magnetic field is turned off, if the particles have been wedged.

It has been shown that a substantially greater effect of a magnetic field 8 of a specific strength is achieved by the wedge effect of the acute-angled regions 10. The effect can be amplified multiple times. In a concrete case, an influence of the relative velocity of two components 2 and 3 to one another which was approximately 10 times as strong as in the prior art was observed in MRF clutches. The possible amplification depends on different factors. It can optionally be amplified further by a greater surface roughness of the rotating bodies 11. It is also possible that externally protruding projections, which can result in still stronger wedge formation, are provided on the outer surface of the rotating bodies 11.

The wedge action or the wedge effect is distributed flatly on the rotating body 11 and the components 2 or 3.

Figure 17:
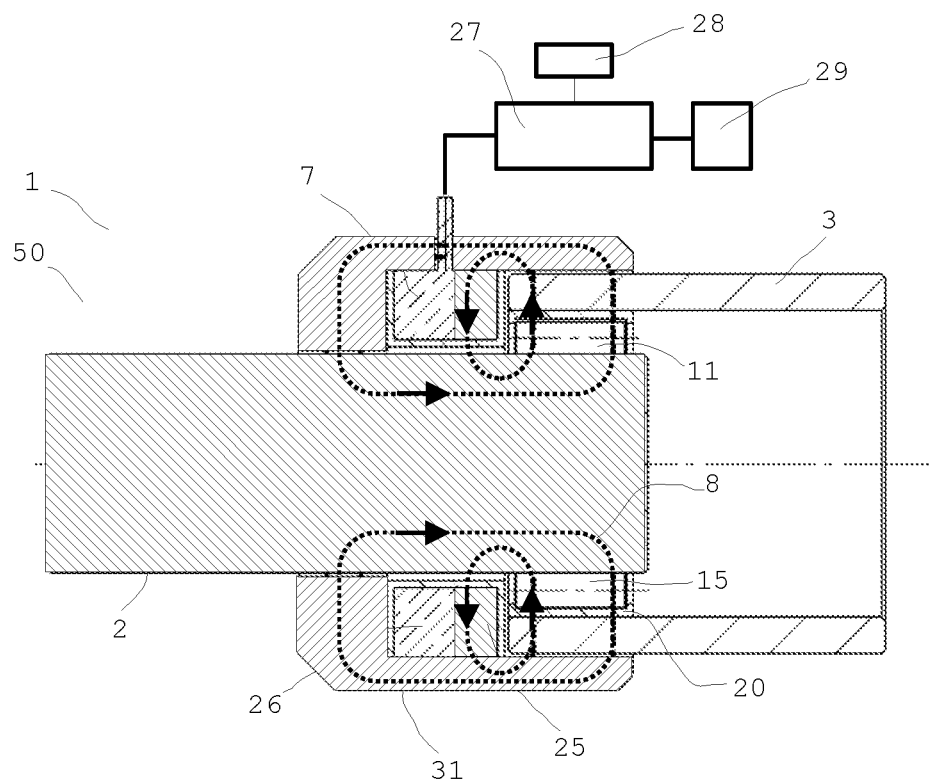
FIG. 17 a magnetorheological transmission device configured as a clutch.

FIG. 17 shows a clutch 50 having a magnetorheological transmission device 1, wherein the components 2 and 3 are embodied as rotating parts. The magnetic field generating unit 7, which comprises a coil 26 and a permanent magnet 25 here, is provided on a stationary component 31. The coil 26 is connected to a control and/or regulating unit 27. This device 27 may be provided by, or may supplement, the control device 703. A permanent magnetic field 8 can be applied using the permanent magnet 25, wherein the magnetic field active in the channel can be modulated by activating the electrical coil 26. The active magnetic field can thus be decreased or amplified.

In this exemplary embodiment, it is preferable for the coil 26 to be configured to deliver strong magnetic pulses, by means of which the permanent magnet 25 is permanently variable. Through short-term pulses in the range of 0.1 to 1000 ms, the magnetization of the permanent magnet 25 can be intentionally varied between zero and its remanence. Following the pulse, the magnetic field strength of the permanent magnet 25 is maintained unchanged for a practically arbitrarily long time. Through suitable modulation of the pulses, the active field strength of the permanent magnet 25 can thus be set arbitrarily frequently, so that a specific field strength can be generated even without continuous power supply.

In order to also be able to vary the strength of the magnetic field of the permanent magnet 25 without continuous power connection, an energy store 28 can be provided, which is embodied as a capacitor and keeps the power ready for at least one pulse, for example. For the targeted regulation of the field strength of the permanent magnet 25, at least one sensor 29 can be provided, which measures the active magnetic field strength, for example. It is also possible that the sensor detects further data, such as the torque, the speed, the relative velocity, the rotational angle of the two components 2 and 3 in relation to one another, or the prevailing temperature or the like. The sensor 29 may be provided by, or may supplement, the sensor means 734. If necessary, corresponding steps can be initiated, for example, if the permissible temperature of the magnetorheological transmission device 1 is exceeded.

The use of a mechanical setting device is also conceivable, in the case of which the field strength in the channel can be changed by moving the magnet, pole shoes, or shielding plates, for example. This mechanical setting can also be used in combination with a Bowden cable and/or an electrical adjustment, for example, if the permanent magnet sets a base force as the operating point and a controller can change the force around this operating point by means of the coil.

Figure 18:
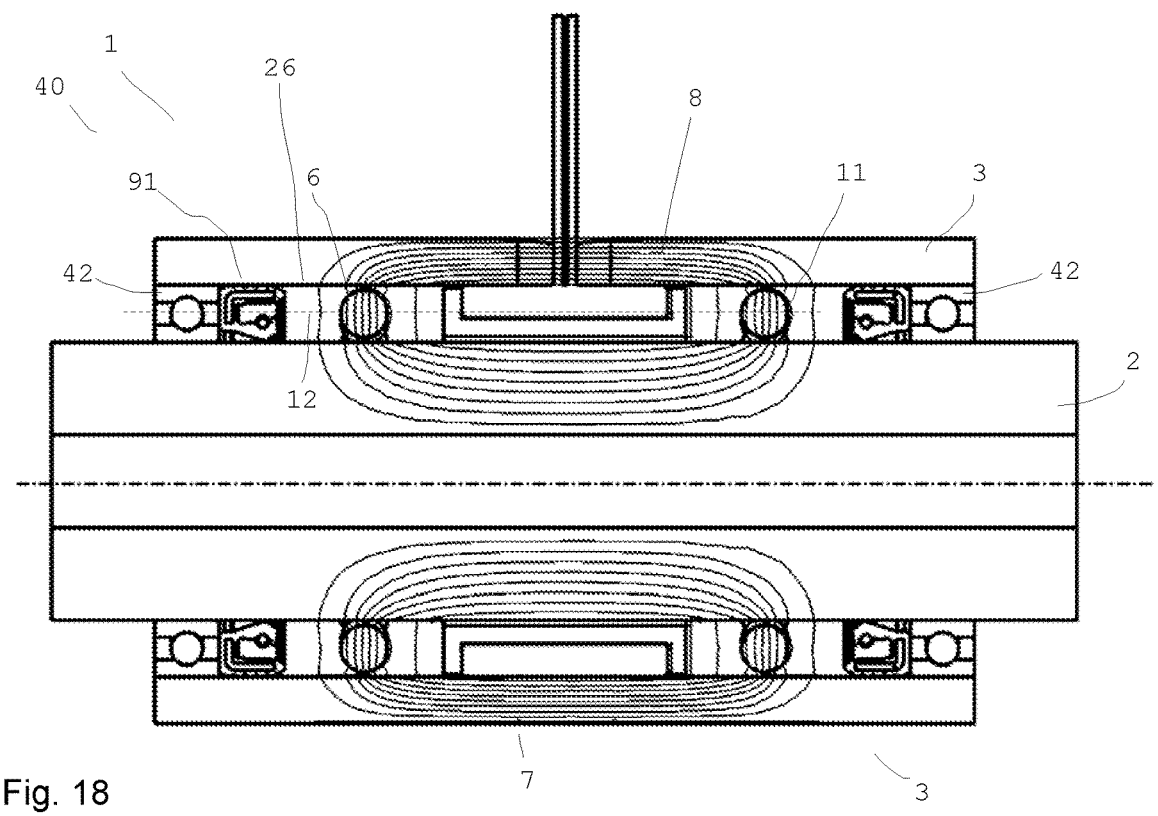
FIG. 18 a magnetorheological transmission device configured as a brake.

FIG. 18 shows a magnetorheological transmission device 1, which is configured as a brake 40. The magnetorheological transmission device 1 has a component 2 embodied as a shaft, whose rotational movement relative to the stationary component 3 can be influenced. Bearings 42 for the rotatable mounting of the components 2, 3 are provided between the stationary component 3 and the rotatable component 2. The rotating bodies 11 between the components 2 and 3 are embodied here as balls 14 and are enclosed by the medium 6 or the magnetorheological fluid 20, respectively. Seals 91 are provided between the rotating bodies 11 and the bearings 42 to protect the bearing 42 and to prevent the escape of magnetorheological fluid.

A magnetic field generating unit 7 embodied as a coil, for example, is used for the targeted control of a magnetic field 8, which also extends through the rotating bodies 11 and is aligned there substantially transversely and here even perpendicularly to the relative movement of the two components 2 and 3 in relation to one another. When the magnetic field 8 is turned on, the rotational movement of the rotating bodies 11 causes chaining together of the particles 19 in the magnetorheological fluid 20, whereby the acute-angled regions 10, which substantially obstruct a further rotation of the component 2 relative to the component 3, arise on each individual rotating body 11. The effect of the magnetorheological fluid is thus substantially amplified.

The MRF wedge housing can be pushed over an (existing) drive shaft, this drive shaft is then braked depending on the active magnetic field 8, wherein the MRF wedge results between the shaft surface and the rotating bodies 11. A very simple construction therefore results. Normal brakes or clutches typically require a plate or other flanged parts for this purpose and have a fixed shaft position when viewed axially. In the case of an MRF wedge housing 1 as presently described, the shaft can be axially displaced without this affecting the wedge effect. A separate bearing ring does not have to be affixed to the component 2 used as the shaft.

Figure 19:
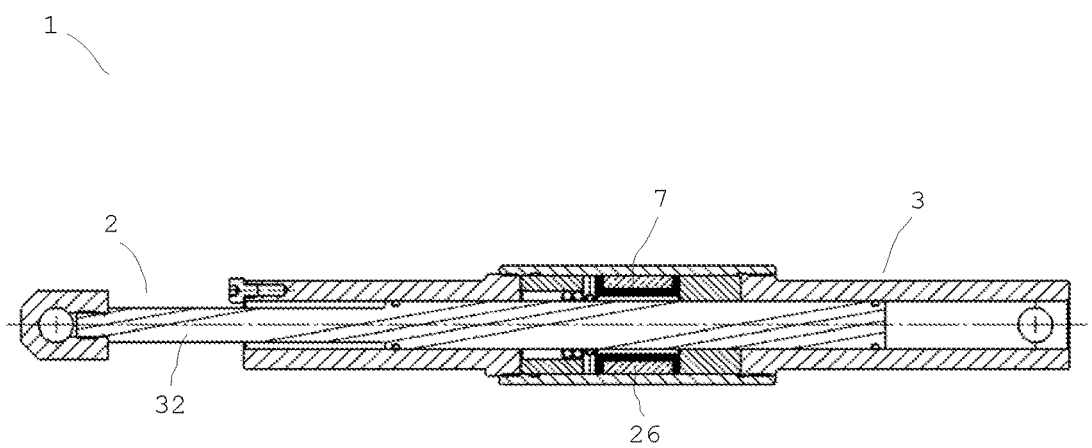
FIG. 19 a magnetorheological transmission device for influencing linear movements.

FIG. 19 shows a magnetorheological transmission device 1 for influencing the linear movements of two components 2 and 3 relative to one another. The magnetorheological transmission device 1 comprises a rod 32, which dips into the component 3 and is provided so it is displaceable therein relative to the component 3. The magnetorheological transmission device 1 according to FIG. 4 can be designed so that in addition to a longitudinal movement, a rotational movement of the two components 2 and 3 in relation to one another can also be permitted and can be influenced by a magnetic field.

Figure 20:
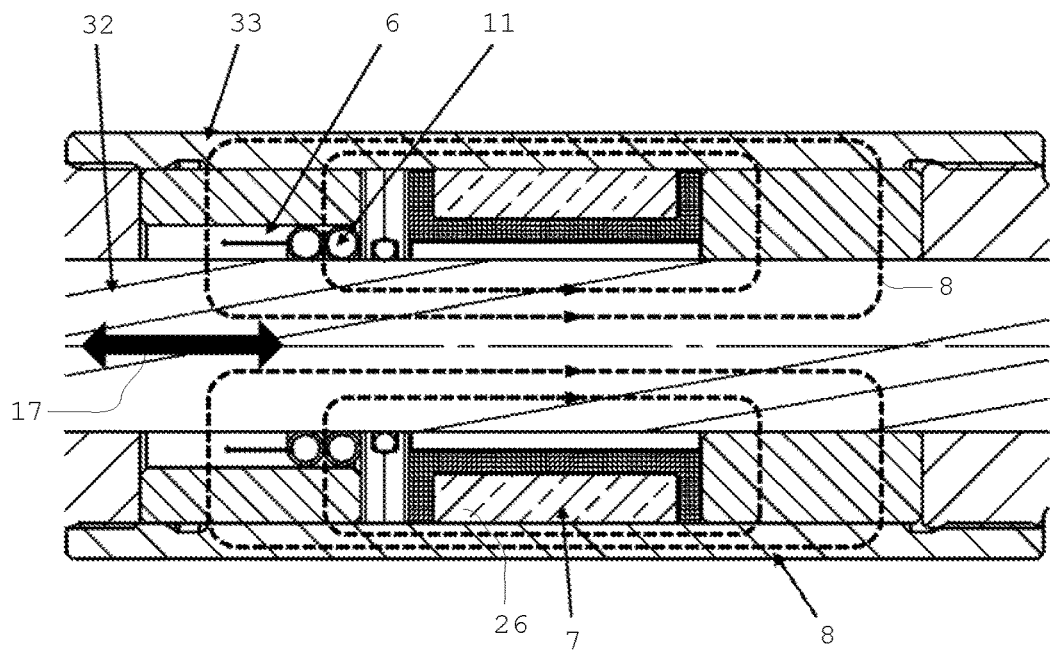
FIG. 20 an enlarged cross section of the device according to FIG. 19.

FIG. 20 shows an enlarged cross section of the central region of the magnetorheological transmission device 1 according to FIG. 4. The electrical coil 26 is clearly recognizable as a magnetic field generating unit 7, in order to generate a targeted magnetic field 8.

Balls are radially arranged between the rod 32 and the component 3 as rotating bodies 11, which are provided so they are movable in the axial direction relative to the rod 32 or the component 3 and move in relation to one another in the event of a relative movement of the component 2 and 3 and in particular can be set into a rotational movement. During such a rotational movement, the acute-angled regions 10 result, which in the event of activation of the magnetic field 8 result in chaining together of the particles 19 of the magnetorheological fluid 20 as the medium 6 and therefore decelerate or make more difficult or even block the relative movement of the rod 32 to the component 3. Such a magnetorheological transmission device 1 can also be used as a vibration damper or shock absorber or the like.

Figure 21:
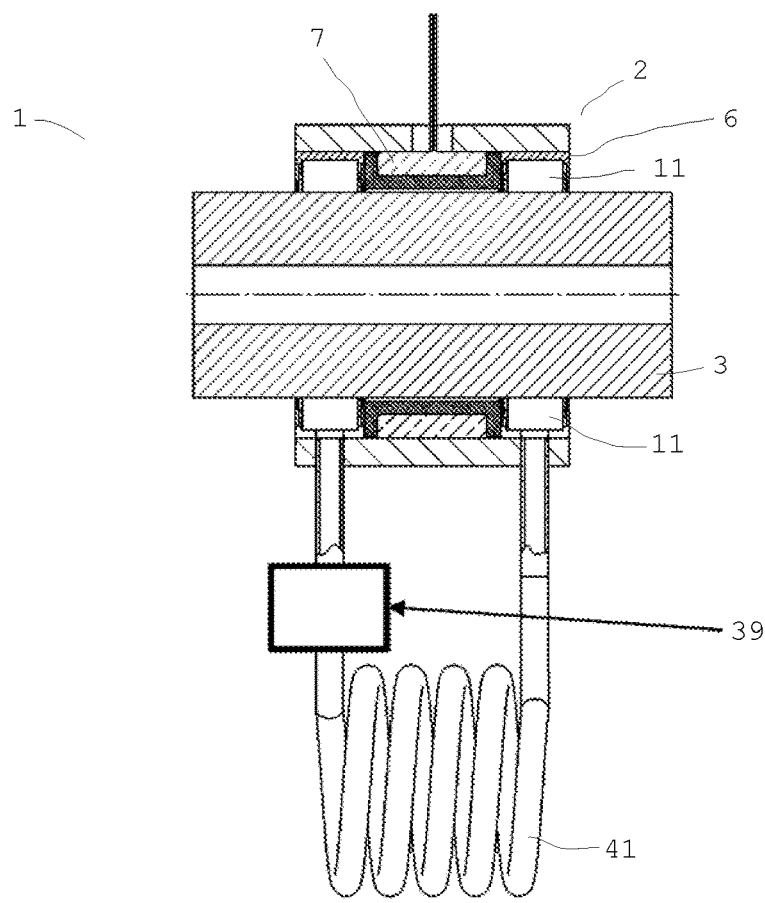
FIG. 21 a magnetorheological transmission device with a cooling unit.

FIG. 21 shows a magnetorheological transmission device 1 with a stationary component 2 and a rotatable component 3 embodied as a shaft, in which cylindrical rotating bodies are arranged as the rotating bodies 11 between the component 2 and the component 3 and are enclosed by a medium 6, which reacts to a magnetic field 8 of a magnetic field generating unit 7.

For example, if the magnetorheological transmission device 1 in FIG. 21 is used as a brake, the braking energy is dissipated in the medium 6. Frequent and/or strong braking can supply a large amount of energy to the medium, which can result in significant heating of the medium or fluid 6 and the rotating bodies 11. In order to dissipate the resulting heat energy, a cooling unit 41 can be provided, which can be force-activated via a pump 39, for example. The pump 39 can also be integrated in the bearing as a separate part, which utilizes the relative movement. At least a part of the rotating body and/or the components is advantageously designed so that a relative movement moves at least a part of the medium in the cooling circuit.

A further advantageous effect of a force-activated cooling unit can be continuous mixing of the liquid and the provision of sufficient MRF, wherein the cooling unit can be used as a storage container for the MRF liquid.

Figure 22:
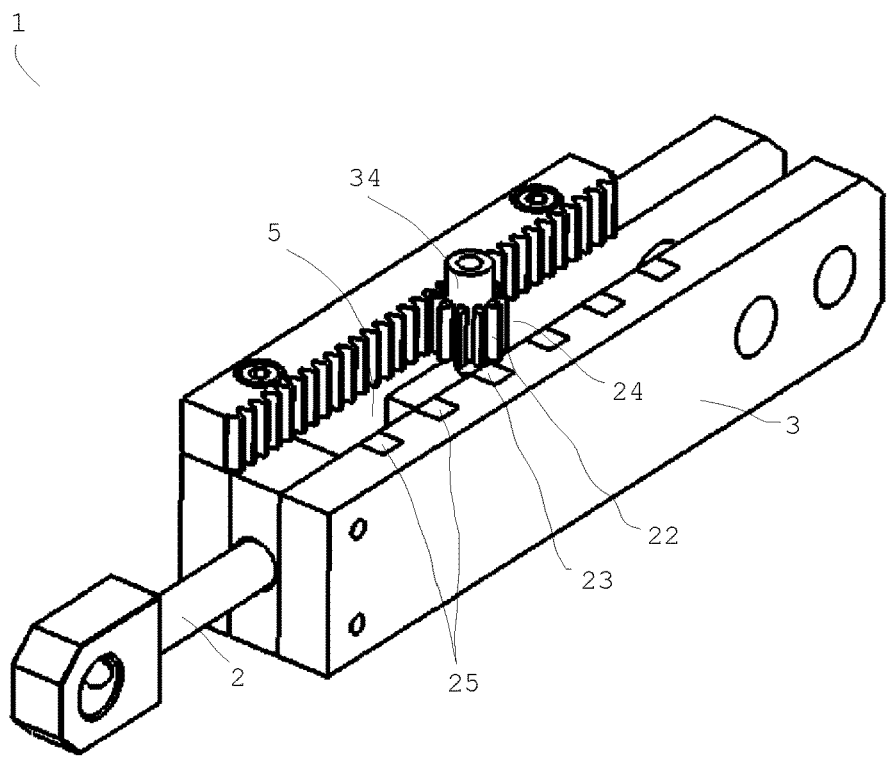
FIG. 22 another magnetorheological transmission device for influencing linear movements.
Figure 23:
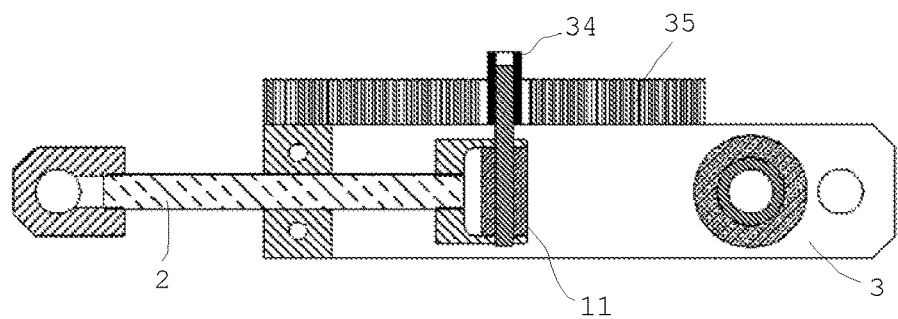
FIG. 23 a cross section from FIG. 22.

FIG. 23 shows a cross section of the magnetorheological transmission device 1 from FIG. 22. The component 2 has a rotatably accommodated rotating body 11, which is provided with a gear wheel 34. The gear wheel 34 meshes with a toothed rack 35 of the component 3. If the component 2 is moved relative to the component 3, it results in a rotational movement of the rotating body 11, since the gear wheel 34 of the rotating body 11 meshes with the toothed rack 34 of the component 3. If the rotating body 11 is enclosed by a medium 6, which can be influenced by a magnetic field 8, through application of an external magnetic field, a magnetorheological fluid 20 can react to the magnetic field, for example. An acute-angled region 10 having a wedge shape 16 thus respectively forms between the plates of the component 3 and the rotating body 11, which makes a further relative movement of the components 2 and 3 in relation to one another more difficult.

The gear wheel 34 and the toothed rack 35 can be dimensioned depending on the application so that the rotational velocity corresponds to the relative velocity of the components 2 and 3 in relation to one another or is increased or decreased or is strongly increased or strongly decreased, respectively.

The component 3 can also comprise only one plate, only one acute-angled region 10 having a wedge shape 16 then results.

Figure 24:
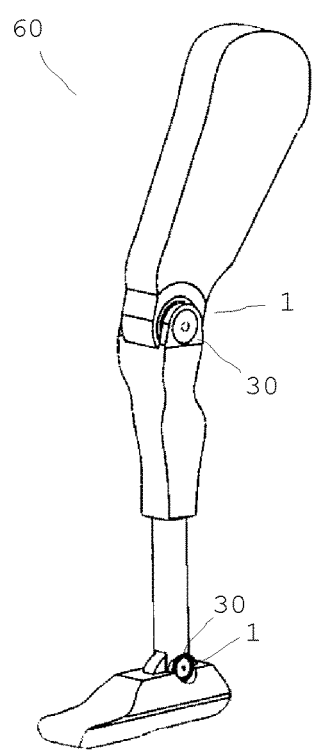
FIG. 24 a prosthesis with magnetorheological transmission devices.

FIG. 24 shows a prosthesis 60, in which magnetorheological transmission devices 1 are used respectively in the knee joint and the foot joint. By activating the corresponding magnetic fields 8, a rotational movement can be damped or blocked, whereby remaining in one position is made easier and a more natural movement sequence is made possible.

Figure 25:
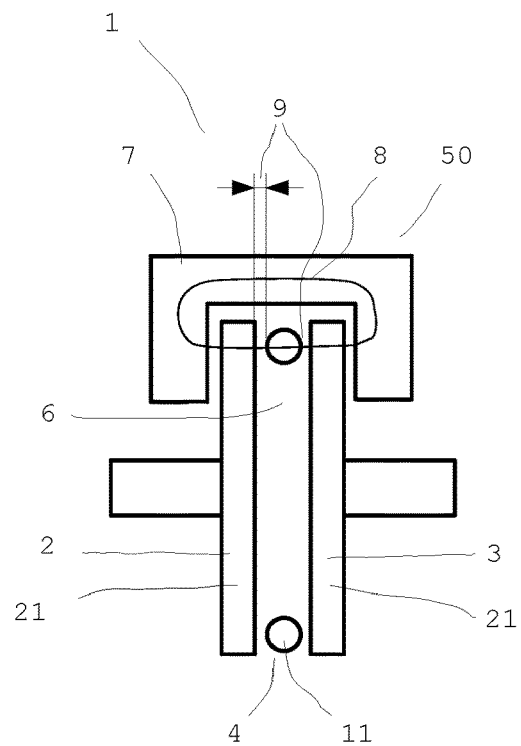
FIG. 25 a very schematic view of a clutch.

FIG. 25 shows a very schematic illustration of a cross section through a clutch 50. Two clutch plates 21 are provided, which are arranged at a slight distance in relation to one another. A medium 6, which is embodied as a magnetorheological fluid 20, for example, is provided between the clutch plates. Furthermore, rotating bodies 11, which are embodied here as rotating bodies 11 in the form of balls 14, are provided between the clutch plates 21. In the event of a relative movement of the clutch plates 21 in relation to one another, the rotating bodies 11 are set into rotational movement. In the event of activation of a magnetic field 8 by a magnetic field generating unit 7, this results in the formation of active acute-angled regions 10, which substantially inhibit a further relative movement of the clutch plates 21 in relation to one another.

Figure 26:
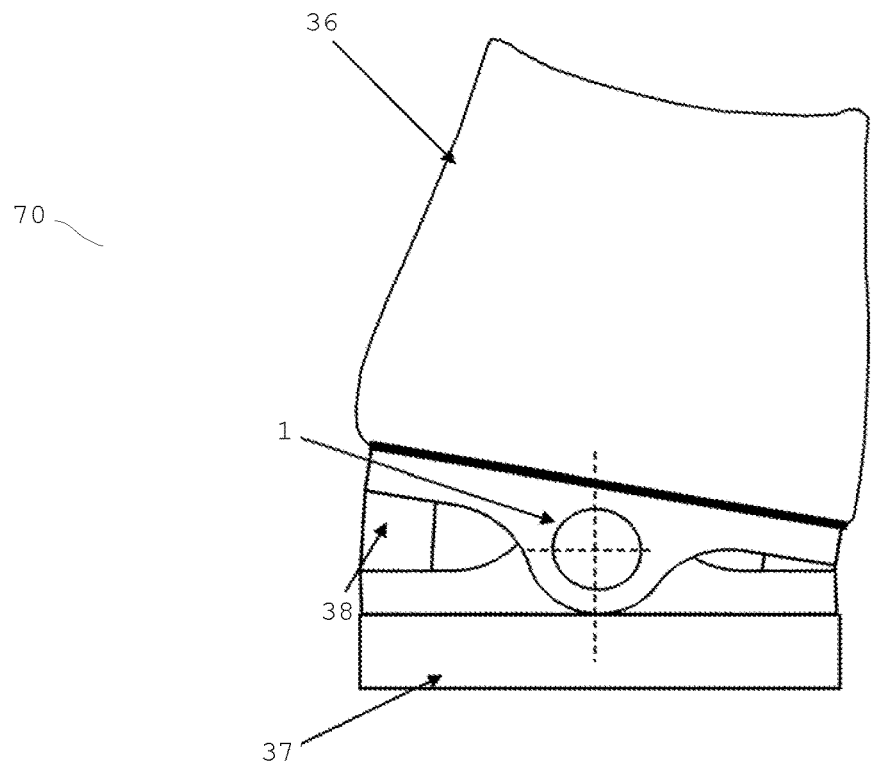
FIG. 26 a shoe with a magnetorheological transmission device.

FIG. 26 shows a further exemplary embodiment of a magnetorheological transmission device 1, which is embodied here as a shoe 70 and is only schematically shown. The shoe 70 has an upper part 36 and a sole 37, which are connected to one another via a pivot joint having a magnetorheological transmission device 1. In order to predefine a base position, a spring unit or a foam 38 is provided, which preloads the shoe 70 in its base position. Hyperpronation or supination can be flexibly compensated for by such a shoe, in that specific angles of inclination are permitted or obstructed. Electronics, sensors, power storage unit, etc. are not shown here for better comprehensibility of the illustration. These elements can preferably be integrated in the sole 37.

Since the force on the two components can be adapted in the millisecond range so that the upper part 36 assumes an arbitrary inclination in relation to the sole 37, such a shoe 70 can be used to continuously compensate for incorrect positions of the human foot. A greater support for the inner foot region can thus result through an incline of the running shoe sole, which is advantageous in the event of hyperpronation, for example. Depending on the running speed, underlying surface, and muscle state, which is also decisively influenced by fatigue, the foot space shape adapts to the new conditions, so that the runner having such a shoe 70 assumes a good position in the running shoe. It is also conceivable that in the event of greater requested adjustment distances, the adjustment procedure is divided into multiple steps. A damping material can optionally also be integrated in the shoe. Sensors can detect the actual state and perform adaptations by means of control and/or regulating electronics. It is also possible to arrange an actuator at the end of the running shoe and not only under the running shoe or under the heel, respectively. An adjustment knob or rotary knob can practically then be arranged at the end of the running shoe.

Figure 27:
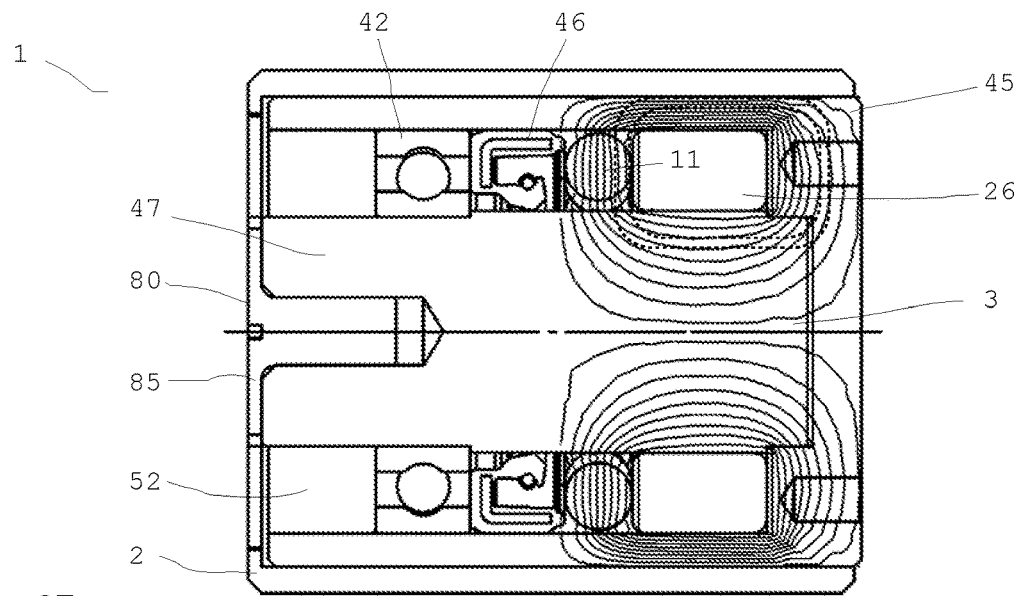
FIG. 27 a rotary knob with a magnetorheological transmission device.

FIG. 27 shows an operating knob or rotary knob 80 having a magnetorheological transmission device 1 in a schematic cross section. The housing 45 as the component 2 can be fixedly attached to a device, for example. The shaft 47 as the component 3 is connected to the rotating part 85. Both components 2 and 3 are mounted so they are rotatable in relation to one another via bearings 42. A thin gap as the free distance 9 is located between the rotating body 11 and the housing 45 and also between the rotating body 11 and the shaft 47. The space enclosing the rotating bodies 11 and optionally nearly the entire inner space can be filled with a magnetorheological fluid as the medium 6. A sealing ring 46 acts as the seal in relation to the bearing 42, which is thus protected from the particles in the magnetorheological fluid.

In the event of activation of the coil 26, a magnetic field 8 is generated, which passes through the rotating bodies 11 and otherwise runs substantially inside the housing 45 and the shaft 47 here, as shown by the field lines drawn as examples. If the magnetic field of the coil 26 is activated, a corresponding resistance is generated in the medium 6 or the MR fluid, so that a corresponding resistance is perceptible during rotation of the rotating part 85. A time-pulsed or pulsating operation is also possible, for example, due to which a pulsing resistance and therefore a pattern is perceptible during the rotation.

The respective current angular position can be detected via a rotary encoder 52. Arbitrary haptic signals can thus be output depending on the activation according to the position, rotational angle, angular velocity, etc. The rotary encoder 52 can also be supplemented with a torque sensor.

Figure 27B:
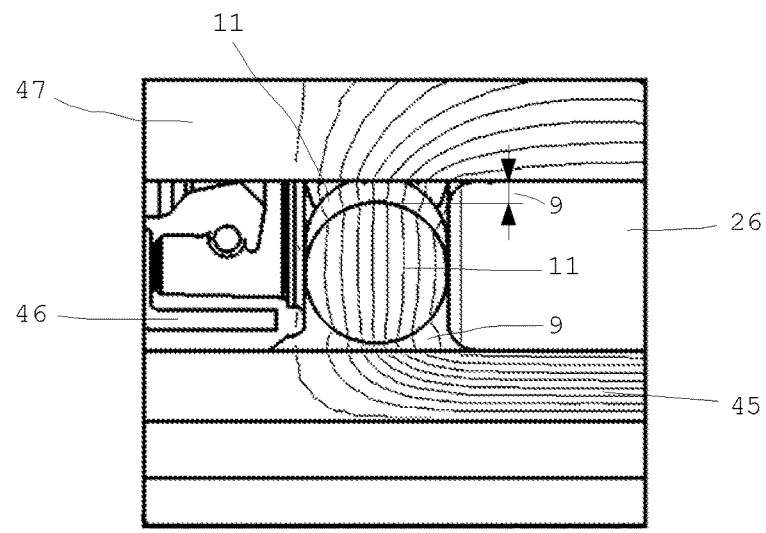
FIG. 27b is a schematic enlarged detail from FIG. 27.

FIG. 27b shows a schematic enlarged detail from FIG. 27, in which one rotating body 11 is entirely visible and one rotating body 11 arranged behind it is only partially visible, since it is partially concealed by the front rotating body 11 and is slightly concealed by the shaft 47. The gap or free distance 9 above and below the rotating body 11 is clearly recognizable. The free distances can be equal on the radial inside and radial outside, but do not have to be. The free distance 9 corresponds in bearing terminology to the running profile. In the case of a bearing, twice the running profile corresponds to the bearing clearance.

FIG. 27b also shows that separate running surfaces are not provided on the shaft 47 and also in the housing 45 as the components 2, 3. The transmission of a clutch or brake torque occurs via the rotating bodies and the amplifying wedge effect of the MRF.

Figure 28:
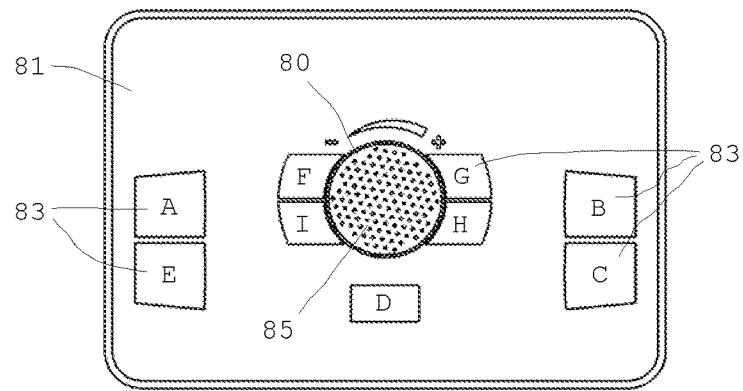
FIG. 28 the rotary knob from FIG. 27 with a display.

FIG. 28 shows a rotary knob 80, which is arranged on a display screen or on a display 81. Further operating elements or buttons 83 can also be provided on the display 81. The display 81 can also be implemented so it is touch sensitive as a touchscreen and can display knobs or buttons 83, for example. For example, it is possible that the buttons 83 are shown depending on the program and/or selection or are activated to make individual operation easier for the user.

Two-dimensional haptic knobs or rotary knobs 80 can also be produced with an additional MRF shear mode.

An MRF haptic knob can be embodied very compactly for actuating units in SLR cameras and other photographic apparatuses, as well as in games consoles and other handheld computers. Such compact MRF coupling units are well suitable for cameras and other outdoor applications because of the small space requirement and the low power consumption in the range of milliwatts or less. The pattern is settable depending on the situation.

Three-dimensional movement elements with variable haptics and robust and precise mounting are fundamentally difficult to produce and are therefore not cost-effective. The combination, for example, of an arrangement of the rotating bodies which is capable of pendulum movements with a magnetorheological fluid is very cost-effectively producible, in contrast.

A four-dimensional rotary knob, which can be displaced in three directions and can additionally also be rotated, for example, can also be provided.

The combination of a 3-D knob with a longitudinal adjustment of an MRF wedge thus results in a 4-D actuating element. All four movement directions can be influenced or varied using a field generating unit.

The use of such haptic knobs is also possible on touch-sensitive displays such as touch display screens in mobile telephones, PDAs, smart phones, portable and stationary computers, and display screens, games consoles, tablet PCs, laptops, etc. For this purpose, at least one haptic element in the form of a rotary knob is provided therein, for example.

Such a haptic element 1 can also be embodied as foldable/pivotable or displaceable and can be displaced from an idle position on the edge into a position over the display screen, for example. As soon as the haptic element is over the display screen, the display on the display screen can change, i.e., a menu appears under or around the knob.

Instead of a kinematic and parallelogram-like pivot mechanism, for example, an elastic/deformable element can also be used, which can consist of a flexible and semirigid arm made of coiled metal tubing in the form of a gooseneck, for example. One advantage is that the user does not always have to grasp the display screen, which reduces the soiling. In addition, the adjustment and the zooming, for example, go more rapidly: Grasping in the display screen with one finger and moving the rotating regulator with other fingers can trigger a zoom procedure, for example. This is also true for the volume, writing with uppercase and lowercase letters, or the selection of special buttons or a second level during typing.

The user can thus also press with one finger on a separate menu bar, in order to search for the type of the desired actuation. He then performs the desired action using the rotating regulator. The pattern of the rotating regulator then adapts automatically, thus, for example, "on"-"off" or a volume regulation with a pattern possibly having a dynamic stop. If the display screen is rotated during the actuation (touch display screen) (for example, as in the case of mobile telephones or handheld computers −90° from portrait format to landscape format), the pattern adapts automatically, i.e., it also rotates. For example, if the setting range were from six o'clock to 12 o'clock when it is held by the edge, this would change from 12 o'clock to six o'clock upon rotation by 90° clockwise without adaptation. This is also true if the display screen is installed in the knob itself. Such a haptic element can be haptic in all or individual directions (only rotate, rotate and press; joystick, etc.). The haptics adjust themselves depending on the selected action.

One advantage can also result upon the selection of a list such as a telephone book list, for example, since such entries are often too small for "targeting" for large fingers.

Advantages also result in the dark or for people with spectacles who are not currently wearing them. Feedback is received via the haptic rotating regulator and the user knows what he is doing when it is currently dark, for example.

Figure 28B:
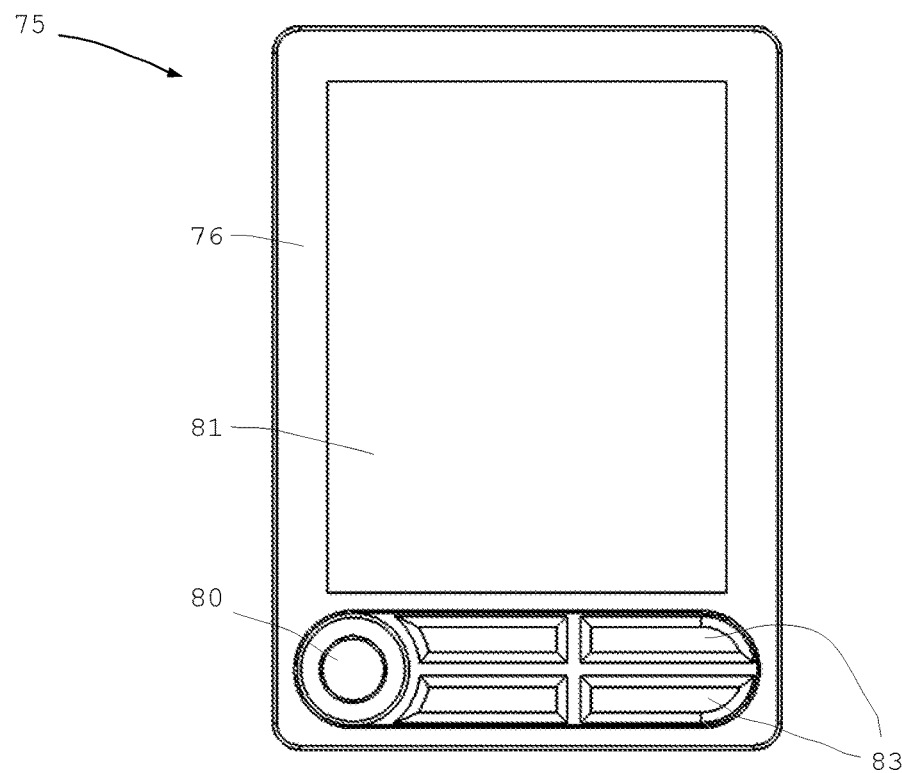
FIGS. 28b and 28c show a portable computer, in a plan view and a perspective view, respectively, with a rotary operating knob mounted adjacent a display screen.

In FIG. 28b, a plan view of a portable computer 75 with a housing 76 is shown. A display 81 and at least one operating knob 80 are provided on the housing 76. The screen or the display 81 is of a touch-sensitive embodiment and reacts for example to touching with a finger and/or operating with a pen. In particular, the portable computer 75 and the display 81 are designed to be controlled by gestures. The portable computer 75 can be operated by appropriate actions of touching with a finger and/or using swiping gestures. Programs can be started and operated and can also be ended again.

Figure 28C:
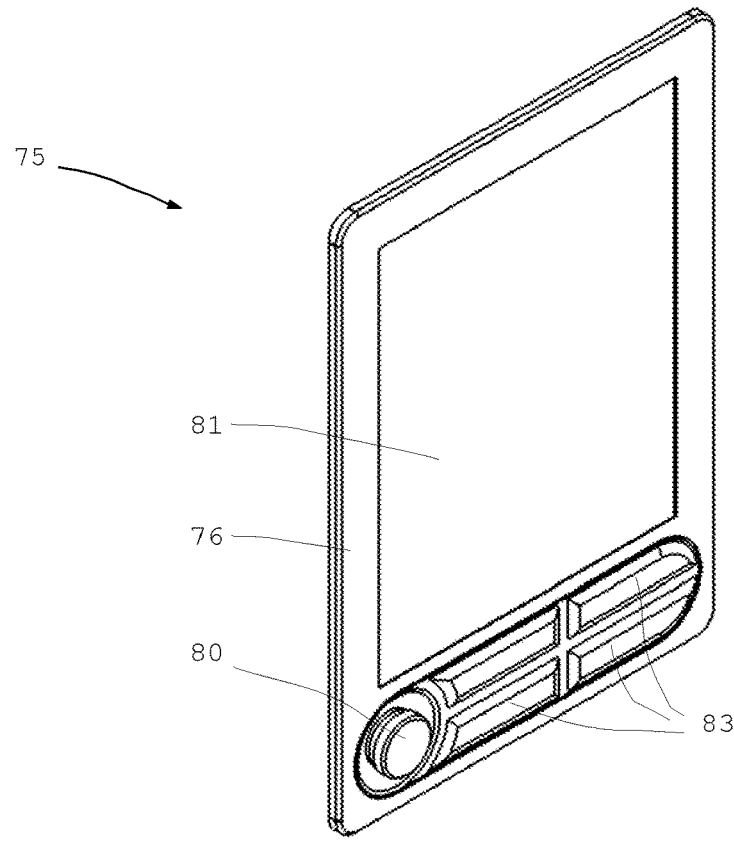

FIG. 28c shows a perspective view of the portable computer 75 according to FIG. 28b. The operating knob 80 protrudes out a little here, so that the rotatable operating knob 80 can be conveniently gripped and turned. In addition, a button 83 or a number of (mechanical) operating buttons may be provided, such as for example separate buttons for "back" or "home" or "menu" and so on.

It is possible and preferable to use an operating knob 80 that is mechanically and/or electrically constructed in the way shown in one of FIG. 27, 27b or 28. The haptic knob or the operating knob 80 is preferably rotatable by more than 360° and in the switched-off state is in particular continuously rotatable. The haptic operating knob 80 may be advantageously used for operating the portable computer 75. Similarly, a stationary computer or a stationary display device and/or operating device with such an operating knob 80 may be used.

The haptic knob or the operating knob 80 may also be embodied as foldable or pivotable or displaceable. It may for example be displaced from the idle position into a position over the display screen. As soon as the haptic knob or the operating knob 80 is over the display screen, the display on the display screen changes and, for example, a menu may appear in the proximity of the knob.

Figure 29:
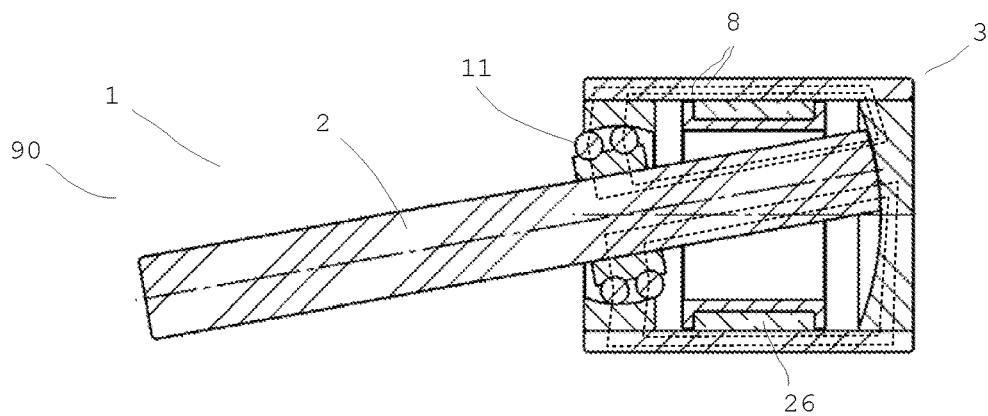
FIG. 29 a joystick with a magnetorheological transmission device.

FIG. 29 shows such a 3-D knob as a joystick 90, which is provided to be pivotable in various directions. A haptic pattern can be implemented by sensor-controlled or time-controlled activation of the coil 26. Magnetic field lines 8 are shown as examples. Very low forces occur in this case, whereby the MRF particles are not damaged by high surface pressures.

Figure 30:
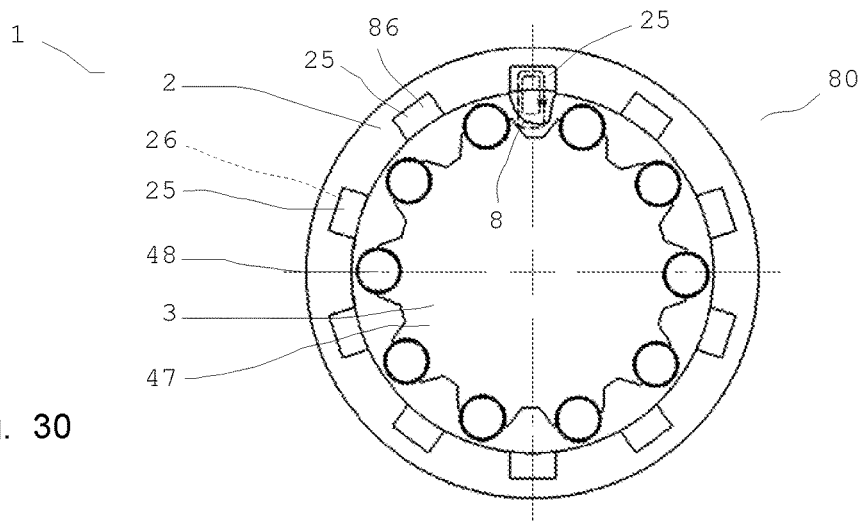
FIG. 30 a further rotary knob in a schematic front view.

FIG. 30 shows a schematic view of a rotary knob 80 as a magnetorheological transmission device 1, which has an outer component 2 and an inner component 3. An MRF is located in a gap 86 between the two components 2 and 3. Protrusions 49, which act as radial projections, protrude from the component 3 embodied as the shaft 47. In addition, permanent magnets 25 are provided at predetermined angular intervals as magnetic field generating units or magnet units or projections on the component 2. The magnetic fields of the permanent magnets 25 result in a local cluster formation in the medium 6. The effect is thus amplified, so that substantial torques can be absorbed. The arrangement of the magnet units 87 results in a perceptible pattern during the rotation of the rotary knob 80. In FIG. 30, the protrusions are partially formed by separate rotating bodies 11, which are arranged in corresponding recesses 88 of the protrusions 49, and can preferably rotate therein.

Figure 31:
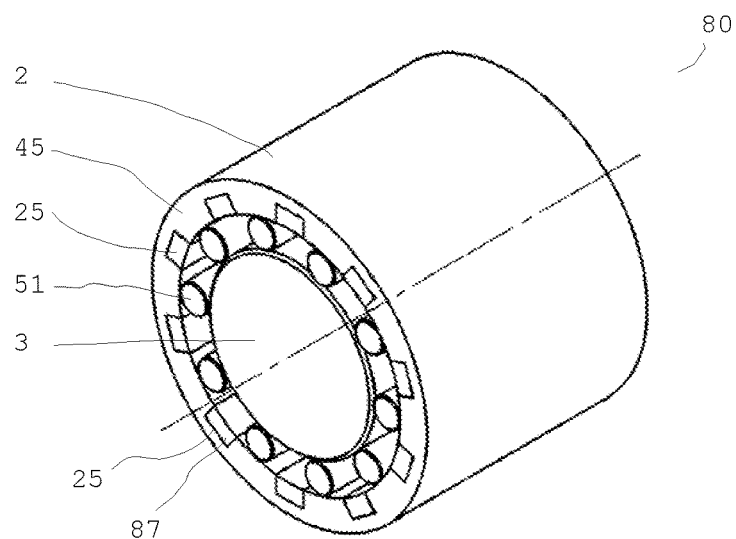
FIG. 31 a different rotary knob in a schematic perspective view.

FIG. 31 shows a rotary knob 80, in which rotating bodies 11 or rolling bodies 51 are provided between the inner component 3 and the outer component 2.

It is possible that the magnetic field goes radially through the gap and/or the rotating bodies 51. It is also possible that the magnetic field goes axially through the gap and/or the rotating bodies 51, for example, axially in on one side and back out on the other side. Furthermore, a combination of the above-mentioned alternatives is also possible.

In concrete embodiments, the cage can also be provided with a friction-increasing layer or can be manufactured from a special material, whereby the torque difference between "turned on" and "turned off" increases. Instead of a rotational mode, a linear mode of operation can also be possible. Ball recirculation bushes or linear bearings with cage or linear ball bearings can also be used to achieve sustainable support.

The overall construction is producible very simply and cost-effectively, since such rotating bodies are mass-produced articles.

In all cases, eddy current effects can be taken into consideration in the case of rapidly rotating rotating bodies.

It is possible to produce one or both components at least partially and/or individual ones or all of the rotating bodies 11 or 51 from a magnetorheological MR plastic or magnetorheological elastomeric material, which changes its shape depending on the field strength and thus clamps the rotating bodies. Such a system can manage completely without a seal.

One embodiment has MRF bound in plastic such as foam or a sponge. A solid lubricant, thus, e.g., lithium, graphite, or MoS2 or the like could be mixed with carbonyl iron powder as the MR powder.

Conventional roller bearings or plain bearings can be used for mounting components 2, 3, which are rotatable in relation to one another. In specific cases, for example, at very low loads, separate bearings can also be omitted.

Figure 32:
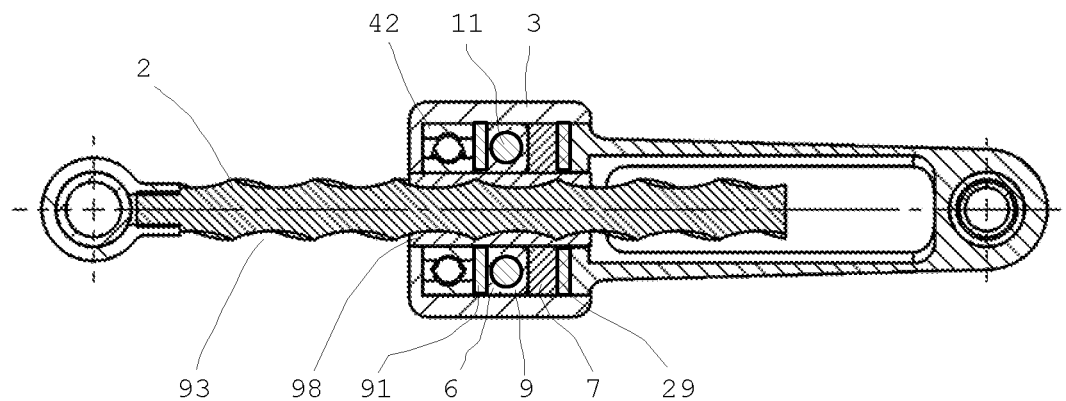
FIG. 32 a further magnetorheological transmission device in a sectional view.

FIG. 32 shows an embodiment of a magnetorheological transmission device 1, in which a linear movement such as a stroke or the like via a spindle, for example, a ball spindle or a simple spindle, is converted into a rotational movement. The one component 2 is embodied as a threaded spindle 93 and is moved linearly. A spindle nut 98 is seated thereon. A linear movement is converted into a rotational movement. Bearings 42 can be provided for the mounting, which are then sealed via a seal 91.

The rotating bodies 11 are arranged in a gap 5, which is filled with MRF. The gap can be subjected to a magnetic field of the magnetic field generating unit 7, whereby the relative movement of the components 2 and 3 is damped and the stroke movement is in turn influenced. Use is possible in different applications, for example, in sporting devices or washing machines as a damper.

Optionally, the magnetorheological transmission device 1 as the MRF brake can also be expanded with a rotary encoder 29. The detection of a rotational movement is more cost-effective and simpler to implement than the detection of a longitudinal movement. This is also true for the sealing. In addition to or instead of the rotary encoder 29, a torque sensor can also be used.

In all embodiments, one or at least one permanent magnet can be provided, which is adjustable by motor or by hand. The use of a displaceable shield is also possible. In all cases, mechanical setting of the brake action and therefore the wedge effect is possible. This can be used, for example, to compensate for physical variables such as temperature, pressure, speed, or the like. The actuation can be performed directly or via a Bowden cable, for example. The adjustment can be continuous.

Figure 33:
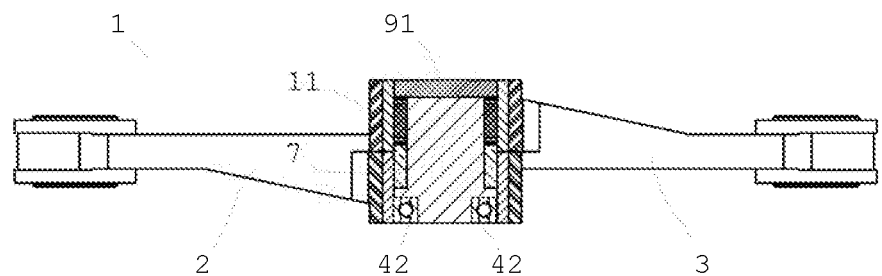
FIG. 33 a toggle lever as a magnetorheological transmission device in a sectional view.
Figure 34:
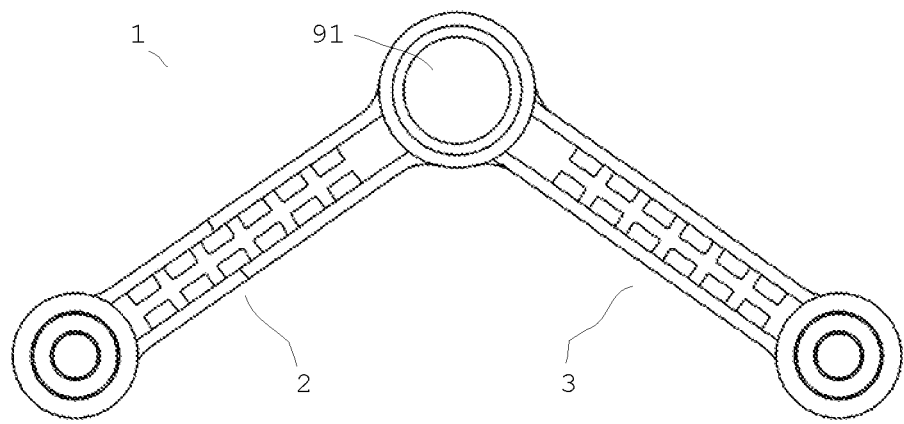
FIG. 34 the toggle lever from FIG. 33 in a side view.

FIGS. 33 and 34 show an MRF transmission device 1 in a toggle lever in two different views.

The toggle lever has two arms, which form the components 2 and 3, which are arranged so they are rotatable in relation to one another here. Bearings 42 can be provided for the load-bearing support. A magnetic field generating unit 7 is used to generate a magnetic field in the gap, in which an MRF and rotating bodies 11 are provided. A very high brake or clutch torque can optionally be built up by the free distance 9, which is sufficiently large, but not excessively large. A seal 91 forms the seal to the outside. The MRF transmission device 1 can also be supplemented with a rotary encoder and/or a torque sensor and/or other sensors.

Such magnetorheological transmission devices can be used for fittings in furniture. For example, as a linear unit for drawer guides, etc. Sufficient guiding is performed by the rotating bodies, while the pullout force is simultaneously variable.

In general, magnetorheological transmission devices 1 with wedge effect can be used as a variable and settable brake in kitchens and in other furniture. The pivoting, for example, the opening of doors or flaps in furniture can be restricted to specific ranges, while rapid opening is possible.

The setting can be performed via pivotable permanent magnets or electrically or via a lever or rotating lever, for example.

Figure 35:
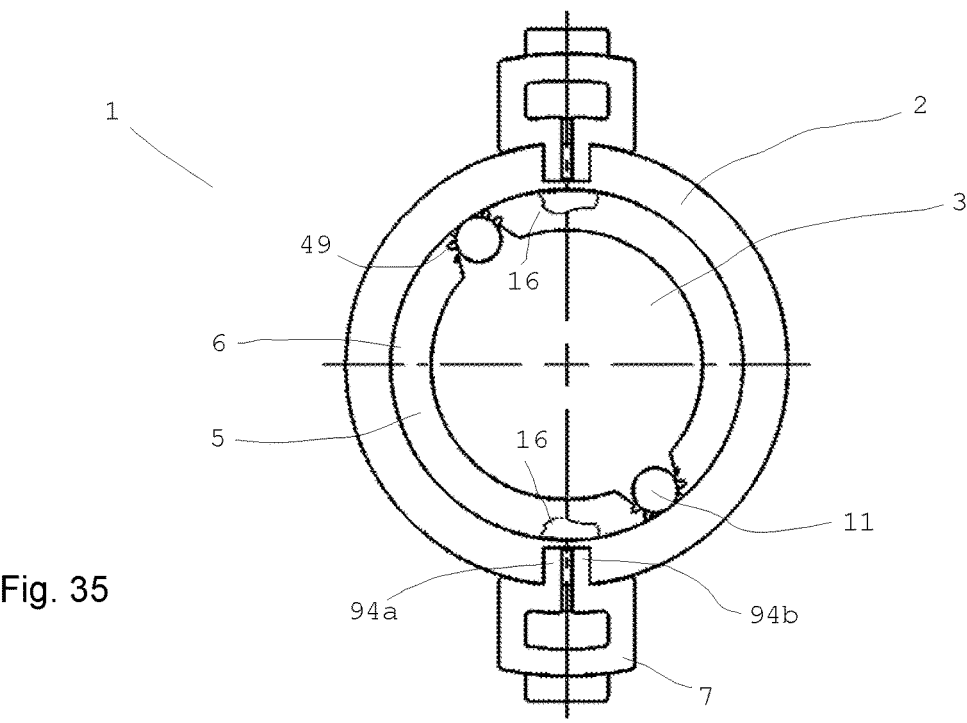
FIG. 35 still another magnetorheological transmission device in a front view.
Figure 36:
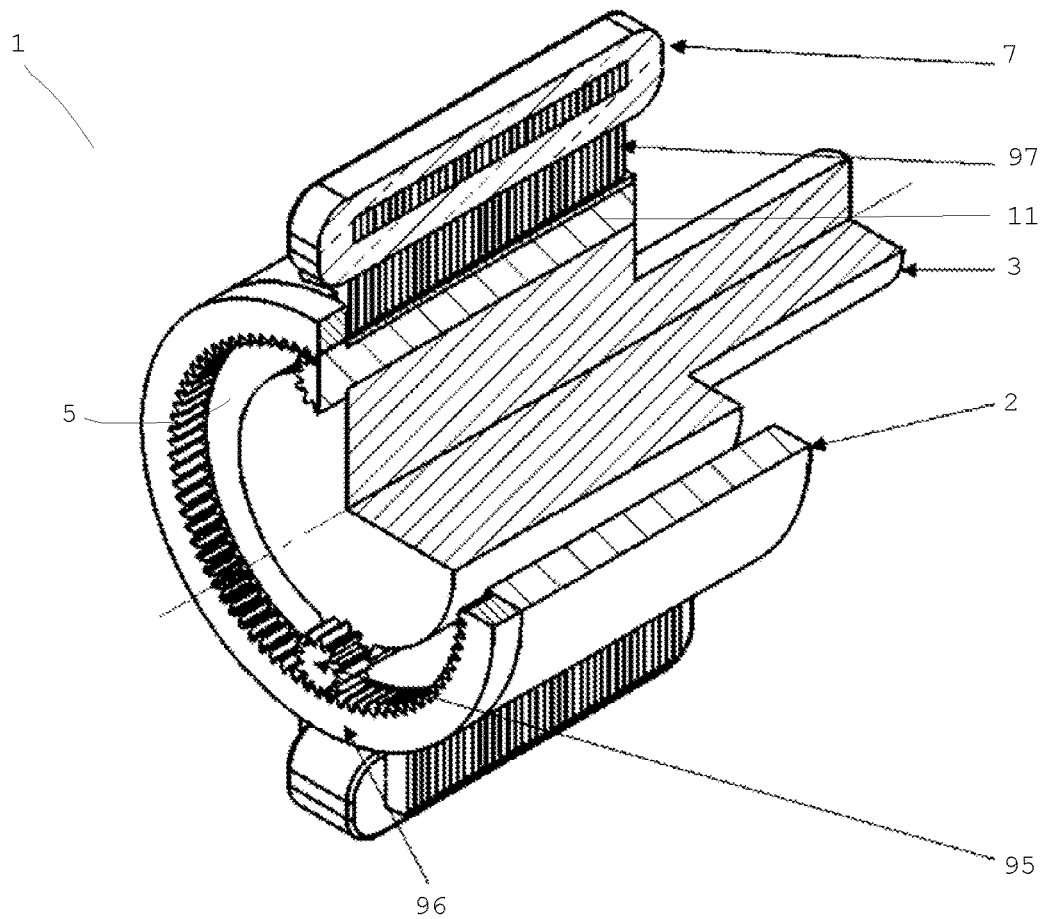
FIG. 36 the magnetorheological transmission device in a sectional view.

FIG. 35 shows an MRF transmission device 1 in a very schematic front view, and FIG. 36 shows the transmission device 1 from FIG. 35 in a very schematic partial cross section.

An inner shaft 3 here is arranged so it is rotatable in an outer hollow shaft as the component 2. The outer hollow shaft 2 can be embodied as stationary. Two electromagnets each having a plate packet 97 are arranged on the sleeve 2 here as magnetic field generating units 7. Three or more electromagnets can also be provided. It is also possible that only one magnet is provided. Permanent magnets can be at least partially used instead of electromagnets.

A gap 5, which is filled with an MRF, is provided between the components 2 and 3. In the gap as the channel 5, two rotating bodies 11 are arranged here, which are embodied here as substantially cylindrical rotating bodies. At one end, the cylindrical rotating bodies 11 can be provided with pinions 95, which are force-guided in gear teeth 96, so that a continuous rotational movement of the rotating bodies 11 is ensured. The region of the gear teeth 96 can be substantially free of field and MRF. The coupling predominantly occurs here via the wedge forming in the gap 5. The transmission device can be implemented with various gear teeth or transmission ratios, or also without them, for the forced rotation of the rotating bodies 11.

The magnetic field generating units 7 shown in FIG. 35 each have a north pole 94a and a south pole 94b, which border the channel 5 with the MRF located therein at a small distance from one another. The magnetic field lines run through the two poles 94a and 94b into the ring gap as the channel 5 and form clusters of solidifying MRF therein when the field is applied. The rotating bodies, which are embodied as cylindrical in the region of the ring gap, run on the MRF structures during the forced rotational movement. The wedge effect then resulting and the acute-angled region at the rotating bodies result in a very strong braking torque.

Figure 37:
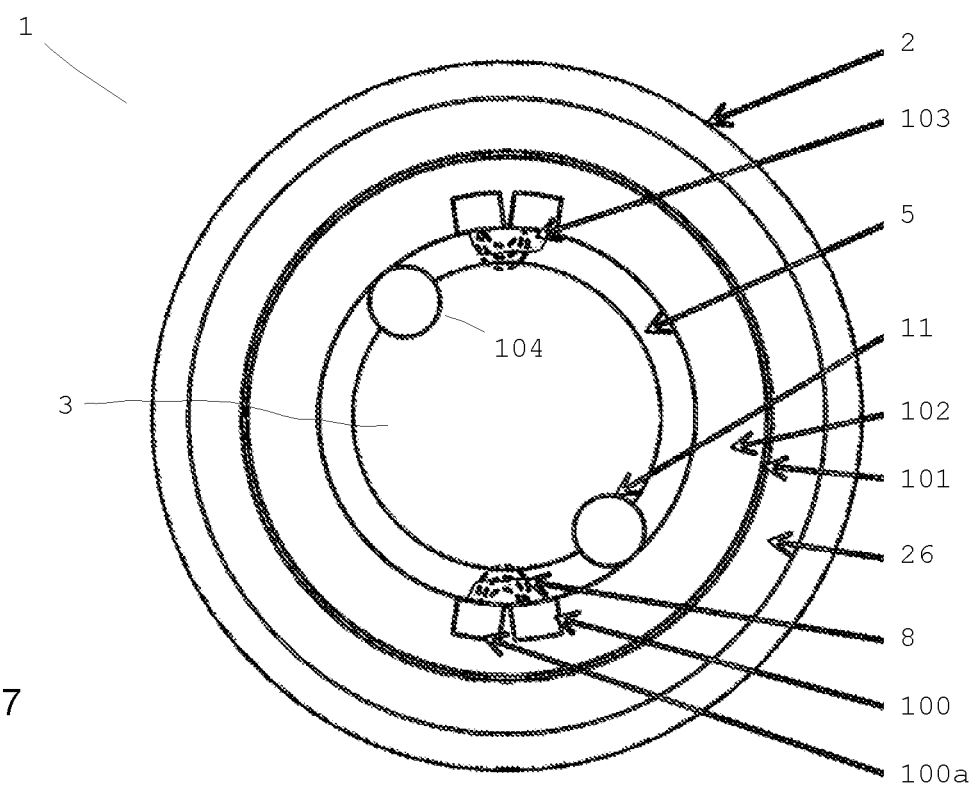
FIG. 37 still another magnetorheological transmission device in a sectional view.
Figure 38:
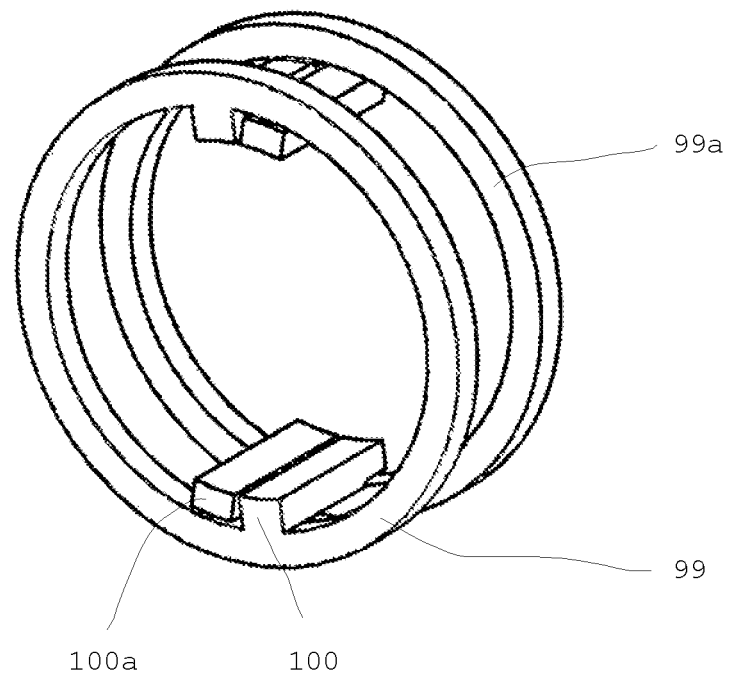
FIG. 38 the pole plates of the magnetorheological transmission device from FIG. 37.

Such a magnetorheological transmission device 1 as a wedge clutch according to FIG. 35 can also have a coil fastened in a nonrotating housing, which optionally generates a magnetic field, in an alteration according to FIG. 37. The magnetic field is conducted via pole plates 99 and 99a and is closed via fingers 100 and 100a, which are fastened axially on the pole plates 99 and 99a. The pole plates 99, 99a are shown in FIG. 38 in a detail view. The MRF is solidified to form clusters 103 in the MRF channel 5 or gap between the fingers 100 and 100a of the pole plates 99 and 99a. The pole plates 99 and 99a rotate with the drive shaft 2. If the solidified MRF regions 103 meet the rotating bodies 11 arranged in the semicircular recesses 104, which rotating bodies are fastened on the output shaft 3, these rotating bodies are briefly entrained by the magnetic field.

The coils can be provided as stationary by transmitting the field 8 radially from the outside via the air gap 101 into the pole plates 99 and 99a. Transmitting the power supply via slip rings is not necessary. The magnetic flux is introduced via the pole plates 99 and 99a and their pole fingers 100 and 100a into the channel 5, where the field lines close and result in the formation of the clusters 103, which interact in a wedge shape with the rotating bodies 11.

The pole plates 99 and 99a are held in a ring, which comprises plastic here, and which is separated via an air gap 101 from the externally rotating component 2 or shaft.

All components are preferably ferromagnetic, except for the part, which is embodied in particular as a plastic part, between the pole plates 99 and 99a and the drive shaft and output shaft 2 and 3.

The two "finger pairs" (MRF clusters) can optionally be activated individually and independently of one another.

In all cases, it is also possible to install magnetorheological transmission devices 1 with wedge effect in a wheel hub of a vehicle, for example, a bicycle, in order to brake, for example. The required electrical power can be acquired as current directly from the installed dynamo, which is connected parallel thereto in particular. Power reclamation can occur via the dynamo. In the event of (full) braking, the magnetorheological transmission device 1 can be used as an MRF brake. The system is coordinated. Since such an MRF brake functions solely electrically and reacts rapidly, the use is well possible. Corresponding running surfaces for the rotating bodies are provided. A majority could thus be braked via a wheel hub dynamo. For the actuation on the handlebars, only a power cable in conjunction with a potentiometer, for example, is required or the transmission is performed wirelessly.

The use as a brake in fitness devices or as a clutch or brake on rowing machines is also possible. The principle can also be taken as a wedge clutch for engaging assemblies and in particular secondary assemblies in the case of motor vehicles. If necessary, two MRF clusters can be provided relatively close to one another, so that the system does not open immediately in the event of a rotational direction change.

In the event of overload, such a clutch opens automatically. No slip rings are optionally required for the power transmission. It can occur via remanence, for example.

If in such an MRF wedge clutch the rotating body 11 still jumps over the MRF wedge or MRF cluster during the first engagement attempt, the leading part is thus accelerated and the engagement procedure is made easier during the second attempt. The use as a free wheel is also possible, by rapidly detecting the rotational direction and turning off the field if another rotational direction is recognized.

The use in a clutch in milling machines is also possible, wherein, for example, disengagement occurs if the emergency shutdown switch is pressed during the running of the machine. It is also possible to suddenly disconnect the clutch in the event of overload. Normal (MRF) clutches do not reduce the torque suddenly.

In all cases and designs, the wedge and/or the magnetic field can also be generated on the inner ring and not only on the outer ring.

The rotating bodies 11 and cages can be embodied as entirely or partially ferromagnetic and paramagnetic or diamagnetic. A completely spherical embodiment and an embodiment in which all parts consist of the same material are also possible. It is also possible that some rotating bodies are ferromagnetic and consist of steel, for example, while others consist of plastic. The use of rotating bodies and balls with different diameters is also possible.

The presently described magnetorheological transmission device 1 can preferably also be used for speed recognition and in particular speed regulation.

The torque can be set depending on the speed via pulse width modulation (PWM). Large axial and radial forces can be generated via an inclined spreading mandrel. The particles can be round, rod-shaped, or have any other shape.

It is also possible to use magnetorheological elastomeric materials. For example, at least one surface can also be a magnetorheological elastomeric material. Fundamentally, a component can be provided with a magnetorheological elastomeric material. It is also possible to coat at least one rotating body 11 and/or at least one of the components 2, 3 with a magnetorheological elastomeric material.

The magnetorheological transmission device 1 can also be embodied as a valve, wherein one rotating body 11 or multiple rotating bodies 11 block the channel.

A magnetorheological transmission device can also be provided for the use of a magnetorheological fluid, which is a product of BASF, in particular the product "Basonetic".

The rheological liquid can consist of greatly varying ingredients, which can be, individually or in combination: iron, carbon steel, NdFeB (neodymium), Alnico, samarium, cobalt, silicon, carbon fibers, stainless steel, polymers, soda lime glass, soda glass, ceramic, and nonmagnetic metals and the like. Dimorphic magnetorheological fluids with nanotubes and/or nanowires are also possible.

The carrier liquid can consist in particular of the following ingredients or a combination thereof: oils and preferably synthetic or non-synthetic oils, hydraulic oil, glycol, water, greases, and the like.

The following is a summary list of reference numerals and the corresponding structure used in the above description of the exemplary embodiments of the invention:

| | |
|---|---|
| 1 | device |
| 2,3 | component |
| 4 | separate part |
| 5 | channel |
| 6 | medium |
| 7 | magnetic field generating unit |
| 8 | field |
| 9 | free distance |
| 10 | acute-angled region |
| 11 | rotating body |
| 12 | rotation axis |
| 13 | rotating body |

-continued

| | |
|---|---|
| 14 | ball |
| 15 | cylinder |
| 16 | wedge shape |
| 17 | direction of the relative movement |
| 18 | direction of the relative movement |
| 19 | magnetic particles |
| 20 | fluid |
| 21 | plate |
| 22 | outer side |
| 23 | projection |
| 24 | gear teeth |
| 25 | permanent magnet |
| 26 | coil |
| 27 | control unit |
| 28 | energy store |
| 29 | sensor |
| 30 | bearing |
| 31 | stationary component |
| 32 | rod |
| 33 | outer tube |
| 34 | gear wheel |
| 35 | toothed rack |
| 36 | upper part of shoe |
| 37 | sole |
| 38 | foam |
| 39 | pump |
| 40 | brake |
| 41 | cooling unit |
| 42 | bearing |
| 45 | housing |
| 46 | sealing ring |
| 47 | shaft |
| 49 | protrusion |
| 50 | clutch |
| 51 | rolling body |
| 52 | rotary encoder |
| 60 | prosthesis |
| 70 | shoe |
| 75 | computer |
| 76 | housing |
| 80 | operating knob |
| 81 | display |
| 82 | touchscreen |
| 83 | button |
| 84 | loudspeaker |
| 85 | rotating part |
| 86 | gap |
| 87 | magnet unit |
| 88 | recess |
| 90 | joystick |
| 91 | seal |
| 92 | running profile |
| 93 | threaded spindle |
| 94a | north pole |
| 94b | south pole |
| 95 | pinion |
| 96 | gear teeth |
| 97 | plate packet |
| 98 | spindle nut |
| 99 | pole plate |
| 99a | pole plate |
| 100 | finger |
| 100a | finger |
| 101 | air gap |
| 102 | plastic ring |
| 103 | cluster |
| 104 | receptacle |
| 700 | input device |
| 701 | operating device |
| 702 | brake device |
| 703 | control device |
| 704 | supporting structure |
| 705 | operating lever |
| 706 | pivot axis |
| 707 | resetting unit |
| 708 | transmission stage |
| 710 | input receiving unit |
| 711 | joystick |
| 713 | sequence |
| 714 | joint |
| 716 | pivot axis |
| 717 | neutral position |
| 718 | belt drive |
| 720 | input system |
| 721 | switch |
| 723 | ripple |
| 728 | rotation axis |
| 733 | slide gate mechanism |
| 734 | sensor means |
| 743 | length |
| 753 | distance |

The invention claimed is:

1. An input device, comprising:
an operating device, said operating device including a supporting structure and an operating lever supported on said supporting structure for pivoting around at least one pivot axis;
a magnetorheological brake device; and
a controller for activating the brake device
a sensor unit for detecting a pivot angle of said operating lever;
wherein said brake device is coupled with said pivot axis, for controlled damping of a pivoting motion of said operating lever by way of said controller; and
wherein said brake device is a magnetorheological transmission equipped with at least two components that are coupled to one another and wherein a coupling intensity can be influenced, wherein at least one channel is formed for influencing the coupling intensity, the channel containing a magnetorheological medium with magnetically polarizable particles, which can be influenced by a magnetic field; and
wherein at least one magnetic field generating unit is provided for generating a magnetic field in the channel in order to influence the magnetorheological medium in the channel using the magnetic field;
wherein one of said components is an outer component enclosing the other component being an inner component, in that at least one of said two components is mounted via at least one separate bearing, and in that a distance between said outer component and said inner component is at least ten times as great as a typical mean diameter of the magnetically polarizable particles in said magnetorheological medium, and the magnetic field of said magnetic field generating unit can be applied at least partially to the channel, in order to selectively chain together the particles or release a chaining of the particles.

2. The input device according to claim 1, further comprising a resetting unit configured, following actuation, to automatically pivot said operating lever back to a nominal neutral position, and wherein said controller is configured to selectively damp a resetting motion carried out by said resetting unit, by way of said brake device.

3. The input device according to claim 2, wherein said resetting unit is configured to automatically fix the operating lever in a current actuating position, and for this purpose to perform, by way of said brake device, controlled setting of a deceleration torque, which corresponds to, or is higher than, a resetting torque of said resetting unit in the current actuating position.

4. The input device according to claim 2, wherein the controller is configured, when at least one defined pivoting angle is reached, to increase a deceleration torque by way of said brake device through at least one specific pivoting angle range, and to fix said operating lever, following overcoming the pivoting angle range in at least one target position outside of the neutral position, and for the purpose to set, by way of said brake device, a controlled deceleration torque, which corresponds to, or is higher than, a resetting torque of said resetting unit in the target position.

5. The input device according to claim 1, wherein said operating lever is accommodated on said supporting structure for pivoting around at least two pivot axes, and wherein at least one brake device is coupled with at least one pivot axis each, and wherein said controller is configured, given a pivoting motion of said operating lever, to separately damp each of said pivot axes.

6. The input device according to claim 1, wherein said controller is configured to actuate said brake device depending on a control command of an input receiving unit coupled with said input device, and/or a control command from said input device.

7. The input device according to claim 6, wherein said controller is configured to convert the control command to at least one haptic signal perceptible on said operating lever, being a defined sequence of deceleration torques, to enable a user to receive a haptic feedback due to an input made and/or during an input.

8. The input device according to claim 1, wherein said controller is configured to selectively block a pivoting motion of said operating lever in at least one direction and to enable the pivoting motion in an opposite direction.

9. The input device according to claim 1, wherein said controller is configured to simulate a slide gate mechanism, by a combination of a plurality of detent positions and at least one neutral position and a plurality of blockings of said operating lever in dependence on the pivoting angle.

10. The input device according to claim 9, wherein multiple slide gate mechanisms suitable to be simulated are stored in said controller, and wherein said controller is configured to select and simulate a given slide gate mechanism in dependence on a user input and/or a control command of an input receiving unit.

11. The input device according to claim 1, further comprising a transmission stage coupling said brake device with said pivot axis, said transmission stage having a gear ratio between 2:1 and 5:1.

12. The input device according to claim 11, wherein said transmission stage comprises at least one belt drive coupling said pivot axis with a rotation axis of said brake device.

13. The input device according to claim 1, which comprises at least one magnetically conducting part that is at least partially flowed through by the magnetic field of said magnetic field generating device, said magnetically conducting part being disposed in a channel formed between the outer component and the inner component.

14. The input device according to claim 1, wherein said magnetically conducting part in the channel is a rotating body and is embodied as a separate part between said inner and outer components.

15. A method for operating an input device, the method comprising:
pivoting an operating lever of the input device, at least in part manually, about at least one pivot axis, to effect an input into an input receiving unit that is functionally connected with the input device;
selectively damping and enabling at least one pivoting motion of the operating lever by at least one magnetorheological brake device coupled with the pivot axis;
wherein the magnetorheological brake device has an outer component and an inner component having at least one channel therebetween containing a magnetorheological medium with magnetically polarizable particles, and wherein a distance between the outer component and the inner component is at least ten times as great as a typical mean diameter of the magnetically polarizable particles in the magnetorheological medium; and
causing a controller to selectively drive the brake device depending on a pivoting angle of the operating lever and/or a time and/or of at least one operating state of the input receiving unit, to perform controlled modification of the damping;
generating a magnetic field with a field generating unit to influence the magnetorheological medium in the channel, by subjecting the magnetorheological medium in the channel to the magnetic field in order to selectively chain together the particles for damping the pivoting motion of the operating lever or to release a chaining of the particles for enabling the pivoting motion of the operating lever.

16. The method according to claim 15, wherein the operating state of the input receiving unit relates to at least one parameter selected from the group consisting of: power status, speed, acceleration, position in space, ambience, ground traveled, work performed, selected user profile, selected operating mode, activities of an assistance system, activities of an operating assistance system, software-simulated situation, and input conditions for operating a program.

17. The method according to claim 15, which comprises selectively increasingly damping or blocking a pivotability of the operating lever, in the case of an operating state showing disturbances above a threshold value and/or endangerment, and/or if an assistance system actively intervenes in using the input receiving unit.

18. The method according to claim 15, wherein an operating state, showing a parameter above a threshold value and/or danger above a threshold value, and/or involving intervention by an assistance system by means of a controlled sequence of different deceleration torques, is signaled by haptics during a pivoting motion of the operating lever.

19. The method according to claim 15, which comprises blocking a pivoting motion of the operating lever more intensely, variably but controlled, depending on a real operational situation and/or depending on a software-simulated situation.

* * * * *